(12) United States Patent
Fu et al.

(10) Patent No.: US 12,171,741 B2
(45) Date of Patent: Dec. 24, 2024

(54) 2,3-DIHYDROBENZO[B]THIOPHENE DERIVATIVES AS HYPOXIA INDUCIBLE FACTOR-2(ALPHA) INHIBITORS

(71) Applicant: NiKang Therapeutics, Inc., Wilmington, DE (US)

(72) Inventors: Jiping Fu, Danville, CA (US); Yan Lou, Pleasanton, CA (US); Yigang He, Newark, DE (US)

(73) Assignee: NiKang Therapeutics, Inc., Wilmington, DE (US)

(*) Notice: Subject to any disclaimer, the term of this patent is extended or adjusted under 35 U.S.C. 154(b) by 775 days.

(21) Appl. No.: 17/275,644

(22) PCT Filed: Sep. 10, 2019

(86) PCT No.: PCT/US2019/050432
§ 371 (c)(1),
(2) Date: Mar. 11, 2021

(87) PCT Pub. No.: WO2020/055883
PCT Pub. Date: Mar. 19, 2020

(65) Prior Publication Data
US 2022/0054451 A1    Feb. 24, 2022

Related U.S. Application Data

(60) Provisional application No. 62/729,902, filed on Sep. 11, 2018.

(51) Int. Cl.
| | | |
|---|---|---|
| A61K 31/381 | (2006.01) | |
| A61K 31/4365 | (2006.01) | |
| A61K 31/4436 | (2006.01) | |
| A61K 45/06 | (2006.01) | |
| A61P 35/00 | (2006.01) | |
| C07D 333/62 | (2006.01) | |
| C07D 333/64 | (2006.01) | |
| C07D 409/12 | (2006.01) | |
| C07D 495/04 | (2006.01) | |

(52) U.S. Cl.
CPC ........ A61K 31/381 (2013.01); A61K 31/4365 (2013.01); A61K 31/4436 (2013.01); A61K 45/06 (2013.01); A61P 35/00 (2018.01); C07D 333/62 (2013.01); C07D 333/64 (2013.01); C07D 409/12 (2013.01); C07D 495/04 (2013.01)

(58) Field of Classification Search
CPC ............. A61K 31/381; A61K 31/4365; A61K 31/4436; A61K 45/06; A61P 35/00; C07D 333/62; C07D 333/64; C07D 409/12; C07D 495/04
See application file for complete search history.

(56) References Cited

U.S. PATENT DOCUMENTS

| | | |
|---|---|---|
| 6,133,279 A | 10/2000 | Cynshi et al. |
| 9,908,845 B2 | 3/2018 | Dixon et al. |
| 10,098,878 B2 | 10/2018 | Bruick et al. |
| 10,155,726 B2 | 12/2018 | Wehn et al. |
| 2016/0362390 A1 | 12/2016 | When et al. |
| 2018/0148413 A1 | 5/2018 | When et al. |
| 2019/0048421 A1 | 2/2019 | Kim et al. |
| 2019/0282535 A1 | 9/2019 | Josey et al. |
| 2020/0361855 A1 | 11/2020 | Fu et al. |

FOREIGN PATENT DOCUMENTS

| | | | |
|---|---|---|---|
| WO | WO 2006/094292 A2 | 9/2006 | |
| WO | WO 2013/026797 A1 | 2/2013 | |
| WO | WO 2015/035223 A1 | 3/2015 | |
| WO | WO 2015/095048 A1 | 6/2015 | |
| WO | WO 2016/144825 A1 | 9/2016 | |
| WO | WO 2016/145045 A1 | 9/2016 | |
| WO | WO-2017053192 A1 * | 3/2017 | ............. A61P 35/00 |
| WO | WO 2018/031680 A1 | 2/2018 | |
| WO | WO 2019/191227 A1 | 10/2019 | |
| WO | WO 2020/055883 A1 | 3/2020 | |
| WO | WO 2020/081695 A1 | 4/2020 | |
| WO | WO 2020/214853 A1 | 10/2020 | |
| WO | WO 2021/016280 A1 | 1/2021 | |

OTHER PUBLICATIONS

Xie, C., et al. Nature Medicine. vol. 23, pp. 1298-1308. (Year: 2017).*
Fallah, J., et al. Current Oncology Reports (2019) 21: 6. (Year: 2019).*
Ban, H. S., et al. Expert Opinion on Therapeutic Patents. 31:5, 387-397. (Year: 2021).*
International search report and written opinion of PCT/US2019/050432 dated Jan. 13, 2020; 10 pages.
PUBCHEM-CID: 640626 Create Date: Jan. 25, 2006, pp. 1-8; p. 2, structure.
PUBCHEM-SID: 129771694 Deposit Date: Dec. 4, 2011, pp. 1-4; p. 2, structure.
PUBCHEM-CID: 91188833 Create Date: Mar. 17, 2015, pp. 1-6; p. 2, structure.
Wehn et al., "Design and Activity of Specific Hypoxia-Inducible Factor 2# (HIF-2#) Inhibitors for the Treatment of Clear Cell Renal Cell Carcinoma: Discovery of Clinical Candidate (S)-3-((2,2-difluoro-1-hydroxy-7- (methylsulfonyl)-2,3-dihydro-1H-inden-4-yl)oxy)-5-fluorobenzonitrile (PT2385)", J. Med. Chem., DOI: 10.1021/acs.jmedchem.8b01196 Publication Date (Web): Oct. 5, 2018.

(Continued)

Primary Examiner — Eric Olson
Assistant Examiner — Samuel L Galster
(74) Attorney, Agent, or Firm — Squire Patton Boggs (US) LLP

(57) ABSTRACT

The present disclosure provides certain 2,3-dihydrobenzo[b]thiophene compounds that are Hypoxia Inducible Factor 2α (HIF-2α) inhibitors and are therefore useful for the treatment of diseases treatable by inhibition of HIF-2α. Also provided are pharmaceutical compositions containing such compounds and processes for preparing such compounds.

23 Claims, No Drawings

(56) References Cited

OTHER PUBLICATIONS

Xu et al., "3-[(1S,2S,3R)-2,3-Difluoro-1-hydroxy-7-methylsulfonyl-indan-4-yl]oxy-5-fluoro-benzonitrile (PT2977), a Hypoxia-Inducible Factor 2# (HIF-2#) Inhibitor for the Treatment of Clear Cell Renal Cell Carcinoma", J. Med. Chem., DOI: 10.1021/acs.jmedchem.9b00719, Publication Date (Web): Jun. 24, 2019.

* cited by examiner

2,3-DIHYDROBENZO[B]THIOPHENE DERIVATIVES AS HYPOXIA INDUCIBLE FACTOR-2(ALPHA) INHIBITORS

CROSS REFERENCE TO RELATED APPLICATIONS

This application is a national phase entry of PCT Application No. PCT/US2019/050432, filed Sep. 10, 2019 which claims the benefit of U.S. Provisional Application No. 62/729,902, filed Sep. 11, 2018, the contents of both of which are incorporated herein by reference in their entireties.

FIELD OF THE DISCLOSURE

The present disclosure provides certain 2,3-dihydrobenzo[b]thiophene compounds that are Hypoxia Inducible Factor 2α (HIF-2α) inhibitors and are therefore useful for the treatment of diseases treatable by inhibition of HIF-2α. Also provided are pharmaceutical compositions containing such compounds and processes for preparing such compounds.

BACKGROUND

Hypoxia is as an important regulator of both physiological and pathological processes, including various types of cancer, liver disease such as nonalcoholic steatohepatitis (NASH), inflammatory disease such as inflammatory bowl disease (IBD), pulmonary diseases such as pulmonary arterial hypertension (PAH), and iron load disorders.

Hypoxia is well-known to drive cancer progression and is strongly associated with poor patient prognosis, resistance to chemotherapy and radiation treatment. With the progress over the past several decades in elucidating molecular mechanisms that enable cellular adaptation to chronic oxygen deprivation, there is a strong interest in developing drugs that can effectively block the hypoxic response pathway in tumors. Among signaling modules, involved in the hypoxic response, that have been explored as therapeutic targets for treating cancer, HIF-α proteins continue to draw interest as they offer the possibility to broadly inhibit downstream hypoxia effects within both tumor and tumor microenvironment. Thus, directly targeting HIF-α proteins offers an exciting opportunity to attack tumors on multiple fronts (see Keith, et al. Nature Rev. Cancer 12: 9-22, 2012).

Hypoxia-Inducible Factors (HIF-1α and HIF-2α) are key transcription factors in the hypoxia pathway, and therefore serve as attractive targets for therapeutic intervention. The half-life of HIF-α proteins is tightly regulated by the oxidative status within the cell. Under normoxic conditions, HIF-specific prolyl-hydroxylases (PHD) hydroxylate specific proline residues on the HIF proteins, which are then recognized by the tumor suppressor von Rippel-Lindau (VHL). The binding of VHL further recruits E3 ubiquition-ligase complex that targets HIF-α proteins for proteasome mediated degradation. Under hypoxic conditions, when PHDs are inhibited as they require oxygen to be functional, HIF-α proteins accumulate and enter the nucleus to activately drive gene expression. In addition, genetic mutations of the VHL gene which result in loss of VHL function lead to constitutively active HIF-α proteins independent of oxygen levels. Upon activation, these transcription factors stimulate the expression of genes that collectively regulate anaerobic metabolism, angiogenesis, cell proliferation, cell survival, extracellular matrix remodeling, pH homeostasis, amino acid and nucleotide metabolism, and genomic instability.

Both HIF-1α and HIF-2a dimerize with HIF-10 (also named as ARNT: aryl hydrocarbon receptor nuclear translocator) and the dimer subsequently binds to hypoxia response elements (HRE) on target genes. The expression of HIF-10 is independent of oxygen levels or VHL status, thus, transcriptional activity of the complex is primarily controlled by the availability of HIF-α proteins. HIF-1α and HIF-2a differ in their tissue distribution, sensitivity to hypoxia, timing of activation and target gene specificity (Hu, et al. Mol. Cell Biol. 23: 9361-9374, 2003 and Keith, et al. Nature Rev. Cancer 12: 9-22, 2012). Whereas HIF-1α mRNA is ubiquitously expressed, the expression of HIF-2a mRNA is found predominantly in kidney fibroblasts, hepatocytes and intestinal lumen epithelial cells. Neither HIF-α is detected in normal tissue with the exception of HIF-2α, which is expressed in macrophages (see Talks, et al. Am. J. Pathol. 157: 411-421, 2000). In response to hypoxia, HIF-1α exhibits a transient, acute transcriptional response. In contrast, HIF-2α presentes a more prolonged transcriptional effect. Furthermore, HIF-2α has greater transcriptional activity than HIF-1 α under moderately hypoxic conditions like those encountered in end capillaries (see Holmquist-Menge/bier, et al. Cancer Cell 10: 413-423, 2006). Although some hypoxia-regulated genes are regulated by both HIF-1α and HIF-2α, certain genes are only responsive to a specific HIF-α protein. For example, lactate dehydrogenase A (LDHA), phosphoglycerate kinase (PGK) and pyruvate dehydrogenase kinase 1 (PDK1) are mostly controlled by HIF-1α, while Oct-4 and erythropoietin (EPO) are exclusively regulated by HIF-2α.

In general, the relative contributions of HIF-α proteins on gene transcription are both cell type specific, and disease specific. In fact, there are reports supporting the HIF-α proteins playing conflicting roles in tumorigenesis. One example is the regulation of HIF-α on MYC, which is an important transcription factor and frequently overexpressed in human cancers. It has been shown that HIF-2α activation increases MYC transcription activity, while HIF-1α inhibits MYC activity. As a result, in MYC driven tumors, HIF-2α inhibition decreased proliferation whereas HIF-1αinhibition increased growth (see Gordan, et al. Cancer Cell 11: 335-347, 2007 and Koshiji et al. EMBO J. 23: 1949-1956, 2004). Therefore, identification of small molecules that specifically inhibit HIF-2α activity is desirable. In addition, HIF-2α is demonstrated to be a key driver of Clear Cell Renal Cell Carcinoma (ccRCC) with VHL deficiency and several other pseudohypoxic tumors (glioblastoma, neuroblastoma etc.). Thus, a specific HIF-2α inhibitor will offer therapeutic benefits with limited toxicity than a pan-HIF a inhibitor.

In addition to a direct role in regulating growth-promoting genes in tumor cells (e.g. ccRCC), HIF-2α also mediates the immunesuppressive effect of hypoxia on the tumor microenviroment. Expression of HIF-2α has been detected in cells of the myeloid lineage, and accumulcation of HIF-2α protein has been readily detected in various human cancers (see Talks K L, et al. Am J Pathol. 2000; 157(2):411-421). Overexpression of HIF-2α in tumor-associated macrophages (TAMs) is associated with high-grade human tumors and is specifically correlated with poor prognosis. Mechanistically, HIF-2α promotes the polarization of macrophages to the immunosuppressive M2 phenotype and enhances migration and invasion of tumor-associated macrophages (see Imtiyaz H Z et al. J Clin Invest. 2010; 120(8):2699-2714). Furthermore, HIF-2α can indirectly promote additional immunosuppressive pathways (e.g. adenosine and arginase etc.) by modulating the expression of key signaling regulators such as adenosine A2B/A2A receptors and arginase. These data suggest that HIF-2α may be a potential therapeutic target for treating a broader range of inflammatory disorders and cancer, as a single agent or in combination with other therapeutic agents e.g., immunotherapies.

Because of the key roles of HIF-α proteins in regulating physiological response to the change of oxygen levels, they have been causally associated with many hypoxia-related pathological processes in addition to cancer. Inflammatory bowel disease (IBD) is a chronic relapsing inflammatory disease of the intestine. Normally, the intestines maintain a dynamic and rapid fluctuation in cellular oxygen tension, with the tips of the epithelial villi being hypoxic and the base of the epithelial villi better oxygenated. A dysregulated epithelial oxygen tension plays a critical role in intestinal inflammation and resolution in IBD (see Shah Y. M., Molecular and Cellular Pediatrics, 2016 December; 3(1):1). Even though HIF-1α and HIF-2α can bind to the same canonical HREs, multiple studies have demonstrated that HIF-1α and HIF-2α regulate distinct subset of genes, leading to contrasting effect in symptoms of IBD. HIF-1α in intestinal epithelial cells is widely recognized as a major protective factor in IBD (see Karhausen J, et al. J Clin Invest. 2004; 114(8):1098-1106; Furuta G T, et al. J Exp Med. 2001; 193(9):1027-1034). However, HIF-2α activation contributes to IBD through multiple mechanisms, including directly regulating a number of pro-inflammatory cytokines such as tumor necrosis factor-α to drive inflammation, and indirectly disrupting intestine barrier integrity through increasing the turnover of tight junction protein occluding (see Xue X, et al. Gastroenterology. 2013; 145 (4):831-841; Glover L E, et al. Proc Natl Acad Sci USA. 2013; 110(49):19820-19825). Therefore, in IBD, a specific HIF-2α inhibitor holds the promise of suppressing chronic activation of HIF-2α to revert the pro-inflammatory response and increase the intestinal barrier integrity.

With the growing epidemic of obesity and metabolic syndrome, NASH is becoming a common chronic liver disease, and limited therapeutic options are available. A recent study has demonstrated a positive correlation between intestinal HIF-2α signaling with body-mass index and hepatic toxicity, with further animal model study supporting the causality of this correlation (see Xie C, et al. Nat Med. 2017 November; 23(11):1298-1308.). Thus, targeting intestinal HIF-2α represents a novel therapeutic strategy for NASH.

PAH is a life-threatening disease with very poor prognosis. Progressive pulmonary vascular remodeling, characterized by concentric pulmonary arterial wall thickening and obliterative intimal lesions, is one of the major causes for the elevation of pulmonary vascular resistance (PVR) and pulmonary arterial pressure (PAP) in patients with PAH (see Aggarwal S, et al. Compr Physiol. 2013 July;3(3):1011-34). Recently, HIF-2α is found to contribute to the process of hypoxic pulmonary vascular remodeling, reduced plasticity of the vascular bed, and ultimately, debilitating PAH (see Andrew S., et al. Proc Natl Acad Sci USA. 2016 Aug. 2; 113(31): 8801-8806, Tang H, et al. Am J Physiol Lung Cell Mol Physiol. 2018 Feb. 1; 314(2):L256-L275.). These studies have offered new insight into the role of pulmonary endothelial HIF-2α in regulating the pulmonary vascular response to hypoxia, and more importantly, offer a much-needed intervention therapeutics strategy by targeting HIF-2α.

Iron is an essential nutrient that is required for oxygen delivery and serves as a cofactor in many key enzymatic and redox reactions. HIF-2α regulates the expression of key genes that contribute to iron absorption, which, when disrupted, leads to iron load disorders. For example, an elegant study with mice lacking HIF-2α in the intestinal epithelium showed HIF-2α knockout results in a significant decrease in the duodenal levels of Dmt, Dcytb and FPN mRNAs, all important genes in iron transport and absorption. More importantly, these effects were not compensated by HIF-1α (see Mastrogiannaki M, et al. J Clin Invest. 2009; 119(5): 1159-1166). Thus, a specific small molecule targeting HIF-2 α holds a great potential of improving iron homeostasis in patients with iron disorders. Therefore, identification of small molecules that inhibit HIF-2α activity is desirable. The present disclosure fulfills this and related needs.

SUMMARY

In a first aspect, provided is a compound of Formula (I):

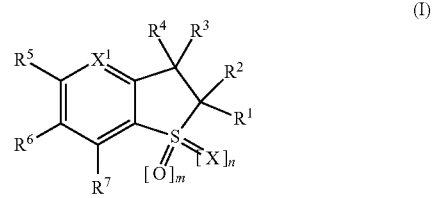

wherein:
m is 0 or 1;
n is 0 or 1, provided that at least one of m and n is 1;
X is O or $NR^8$ where $R^8$ is hydrogen, alkyl, cycloalkyl, cyano, haloalkyl, hydroxyalkyl, alkoxyalkyl, aminoalkyl, alkylcarbonyl, heteroaryl, or heterocyclyl;
$R^1$ is hydrogen, alkyl, or halo;
$R^2$ is hydrogen, alkyl, cycloalkyl, halo, haloalkyl, hydroxyalkyl, alkoxyalkyl, or aminoalkyl; or
$R^1$ and $R^2$ together with the carbon to which they are attached form oxo, cycloalkylene, or 4 to 6 membered heterocyclylene;
$R^3$ is hydrogen, alkyl, halo, haloalkyl, hydroxy, amino, monosubstituted amino, disubstituted amino, or alkoxy;
$R^4$ is hydrogen, deuterium, alkyl, or halo; or
$R^3$ and $R^4$ together with the carbon to which they are attached form oxo, cycloalkylene, or 4 to 6 membered heterocyclylene;
$R^5$ is hydrogen, alkyl, alkoxy, cyano, halo, haloalkyl, or haloalkoxy;
$R^6$ is hydrogen, alkyl, alkoxy, halo, haloalkyl, haloalkoxy, or -L-$R^{10}$ where L is a bond, S, O or NH, and where $R^{10}$ is cycloalkyl, bicyclic cycloalkyl, cycloalkylalkyl, aryl, aralkyl, heterocyclyl, spirocycloalkyl, spiroheterocyclylalkyl, heterocyclylalkyl, heteroaryl, or heteroaralkyl wherein aryl and heteroaryl, each by itself or as part of aralkyl or heteroaralkyl, and heterocyclyl are substituted with $R^a$, $R^b$, and/or R independently selected from hydrogen, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl;

$X^1$ is N, $CR^{11}$, or $C-L^1R^{12}$ where $L^1$ is NH, O, or S, $R^{11}$ is hydrogen, alkyl, alkenyl, alkynyl, alkoxy, cyano, halo, haloalkyl, haloalkoxy, hydroxyalkyl, alkoxyalkyl, or aminoalkyl, and $R^{12}$ is cycloalkyl, cycloalkylalkyl, bicyclic cycloalkyl, aryl, aralkyl, heterocyclyl, spiro-heterocyclyl, heterocyclylalkyl, heteroaryl, or heteroaralkyl wherein aryl and heteroaryl, each by itself or as part of aralkyl or heteroaralkyl, and heterocyclyl are substituted with $R^d$, R, and/or R independently selected from hydrogen, $C_{1-6}$ alkyl, haloalkyl, haloalkyloxy, alkoxy, hydroxy, halo, cyano, hydroxyalkyl, alkoxyalkyl, aminoalkyl, alkenyl, alkynyl, and alkylidienyl, optionally substituted aryl, optionally substituted heteroaryl, and optionally substituted heterocyclyl; provided that when $X^1$ is $CR^{11}$ then $R^6$ is other than H; and when $X^1$ is $C-L^LR^{12}$ then $R^6$ is other than $-L-R^{10}$; and $R^7$ is hydrogen, alkyl, cycloalkyl, alkoxy, cyano, halo, haloalkyl, haloalkoxy, alkylsulfoxide, alkylsulfonyl, $-SO_2NR^{13}R^{14}$ (where $R^{13}$ and $R^{14}$ are independently hydrogen or alkyl), $-S(O)R^{14}(=NHR^{15})$ (where $R^{14}$ is alkyl or haloalkyl and $R^{15}$ is hydrogen or cyano), or heteroaryl optionally substituted with $R^g$, $R^h$, and/or $R^i$ independently selected from hydrogen, alkyl, haloalkyl, haloalkoxy, alkoxy, hydroxy, halo, and cyano; or a pharmaceutically acceptable salt thereof.

In a second aspect, this disclosure is directed to a pharmaceutical composition comprising a compound of the present disclosure (or any of the embodiments thereof described herein), or a pharmaceutically acceptable salt thereof, and a pharmaceutically acceptable excipient.

In a third aspect, this disclosure is directed to a method of treating a disease treatable by inhibition of HIF2α in a patient which method comprises administering to the patient, preferably a patient in need of such treatment, a therapeutically effective amount of a compound of the present disclosure (or any of the embodiments thereof described herein), or comprises administering to the patient, preferably a patient in need thereof, a pharmaceutical composition comprising a therapeutically effective amount of a compound of the present disclosure (or any of the embodiments thereof described herein) and a pharmaceutically acceptable excipient. In one embodiment the disease is cancer such as renal cancer, glioblastoma (see PNAS 2017, 114, E6137-E6146), renal cell carcinoma, pheochromocytomas and paragangliomas (see European Journal of Cancer 2017, 86, 1-4). In another embodiment, non-cancer diseases that could benefit from Hif-2α inhibition include VHL (von Hippel-Lindau) disease (see Oncotarget, 2015, 6, 23036-23037), PAH (pulmonary artery hypertension) (see Mol. Cell. Biol. 2016, 36, 1584-1594), reflux esophagitis (see Current Opinion in Pharmacology 2017, 37: 93-99), hepatic steatosis (see Nature Medicine 2017, 23, 1298-1308), inflammatory disease such as inflammatory bowel disease (see Nature Reviews gastroenterology & Hepatology 2017, 14, 596), and autoimmune disease such as Graft-versus-Host-Disease (see Blood, 2015, 126, 1865).

In a fourth aspect, the disclosure is directed to a compound of the present disclosure, (or any embodiments thereof described herein) or a pharmaceutically acceptable salt thereof for use as a medicament. In one embodiment, the compound of the present disclosure (and any embodiments thereof described herein) or a pharmaceutically acceptable salt thereof is useful for the treatment of one or more of diseases disclosed in the third aspect above.

In a fifth aspect provided is the use of a compound of the present disclosure or a pharmaceutically acceptable salt thereof (and any embodiments thereof disclosed herein) in the manufacture of a medicament for treating a disease in a patient in which the activity of HIF2α contributes to the pathology and/or symptoms of the disease. In one embodiment the disease is one or more of diseases disclosed in the third aspect above.

In a sixth aspect provided is a method of inhibiting HIF2α which method comprises contacting HIF2α with a compound of the present disclosure (or any of the embodiments thereof described herein) or a pharmaceutically acceptable salt thereof; or contacting HIF2α with a pharmaceutical composition comprising a compound of the present disclosure (or any of the embodiments thereof described herein) or a pharmaceutically acceptable salt thereof, and a pharmaceutically acceptable excipient.

In any of the aforementioned aspects and embodiments contained therein involving the treatment of cancer, are further embodiments comprising administering the compound of the present disclosure, or a pharmaceutically acceptable salt thereof (or any embodiments thereof disclosed herein) in combination with at least one additional anticancer agent such as an EGFR inhibitor such as gefitinib, erlotinib, afatinib, icotinib, neratnib, rociletinib, cetuximab, panitumumab, zalutumumab, nimotuzumab, and matuzumab. In another embodiment, the compound of the present disclosure (and any embodiments thereof described herein) or a pharmaceutically acceptable salt thereof is administered in combination with a HER2/neu inhibitor including lapatinib, trastuzumab, and pertuzumab. In another embodiment, the compound of the present disclosure (and any embodiments thereof described herein) or a pharmaceutically acceptable salt thereof is administered in combination with a PI3k/mTOR inhibitor including idelalisib, buparlisib, BYL719, and LY3023414. In another embodiment, the compound of the present disclosure (and any embodiments thereof described herein) or a pharmaceutically acceptable salt thereof is administered in combination with a VEGF inhibitors such as bevacizumab, and/or a multi-tyrosine kinase inhibitors such as sorafenib, sunitinib, pazopanib, and cabozantinib. In another embodiment, the compound of the present disclosure (and any embodiments thereof described herein) or a pharmaceutically acceptable salt thereof is administered in combination with an immunotherapeutic agents such as PD-1 and PD-L1 inhibitors, CTLA4 inhibitors, IDO inhibitors, TDO inhibitors, A2A agonists, A2B agonists, STING agonists, RIG-1 agonists, Tyro/Axl/Mer inhibitors, glutaminase inhibitors, arginase inhibitors, CD73 inhibitors, CD39 inhibitors, TGF-β inhibitors, IL-2, interferon, PI3K-γ inhibitors, CSF-1R inhibitors, GITR agonists, OX40 agonists, TIM-3 antagonists, LAG-3 antagonists, CAR-T therapies, and therapeutic vaccines. When combination therapy is used, the agents can be administered simultaneously or sequentially.

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like. It will be recognized by a person skilled in the art that the term "alkyl" may include "alkylene" groups.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkenyl" means a linear monovalent hydrocarbon radical of two to six carbon atoms or a branched monovalent hydrocarbon radical of three to six carbon atoms containing a double bond, e.g., propenyl, butenyl, and the like.

"Alkyldienyl" is alkenyl as defined above that is attached via the terminal divalent carbon. For example, in the compound below:

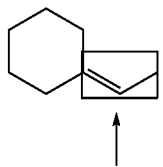

the alkyldienyl group is enclosed by the box which is indicated by the arrow.

"Alkynyl" means a linear monovalent hydrocarbon radical of two to six carbon atoms or a branched monovalent hydrocarbon radical of three to six carbon atoms containing a triple bond, e.g., propynyl, butynyl, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Alkylsulfoxide" means a —S(O)R radical where R is alkyl as defined above, e.g., methylsulfoxide, ethylsulfoxide, and the like.

"Amino" means a —NH$_2$.

"Alkylamino" means a —NHR radical where R is alkyl as defined above, e.g., methylamino, ethylamino, propylamino, or 2-propylamino, and the like.

"Aminoalkyl" means a linear monovalent hydrocarbon radical of one to six carbon atoms or a branched monovalent hydrocarbon radical of three to six carbons substituted with one or two —NR'R" where R' and R" are independently hydrogen, alkyl, haloalkyl, hydroxyalkyl, alkoxyalkyl, or alkylcarbonyl, each as defined herein, e.g., aminomethyl, aminoethyl, methylaminomethyl, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, such as one or two alkoxy groups, as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Alkylcarbonyl" means a —C(O)R radical where R is alkyl as defined herein, e.g., methylcarbonyl, ethylcarbonyl, and the like.

"Aryl" means a monovalent monocyclic or bicyclic aromatic hydrocarbon radical of 6 to 10 ring atoms e.g., phenyl and naphthyl.

"Aralkyl" means a -(alkylene)-R radical where R is aryl as defined above, e.g., benzyl, phenethyl, and the like.

"Bicyclic cycloalkyl" means a fused bicyclic saturated monovalent hydrocarbon radical of three to ten carbon atoms optionally substituted with one or two substituents independently selected from alkyl, halo, alkoxy, hydroxy, and cyano. Examples include, but are not limited to, decalin, octahydro-1H-indene, and the like.

"Cycloalkyl" means a monocyclic saturated monovalent hydrocarbon radical of three to ten carbon atoms optionally substituted with one or two substituents independently selected from alkyl, halo, alkoxy, hydroxy, and cyano. Examples include, but are not limited to, cyclopropyl, cyclobutyl, cyclopentyl, or cyclohexyl, and the like. Cycloalkyl may include cycloalkylene as defined herein.

"Cycloalkylalkyl" means a -(alkylene)-R radical where R is cycloalkyl as defined above, e.g., cyclopropylmethyl, cyclohexylmethyl, and the like.

"Cycloalkylene" means a divalent cycloalkyl, as defined above, unless stated otherwise.

"Carboxy" means —C(O)OH.

"Dialkylamino" means a —NRR' radical where R and R' are alkyl as defined above, e.g., dimethylamino, methylethylamino, and the like.

"Disubstituted amino" means a —NRR' radical where R and R' are independently alkyl, haloalkyl, hydroxyalkyl, alkoxyalkyl, or alkylcarbonyl, each as defined herein, e.g., dimethylamino, ethylmethylamino, bis-hydroxyethylamino, bis-methoxyethylamino, diethylaminoethylamino, and the like.

"Halo" means fluoro, chloro, bromo, or iodo, preferably fluoro or chloro.

"Haloalkyl" means alkyl radical as defined above, which is substituted with one or more halogen atoms, e.g., one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with one or more fluoro only, it can be referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic group of 4 to 8 ring atoms in which one or two ring atoms are heteroatom selected from N, O, and S(O)$_n$, where n is an integer from 0 to 2, the remaining ring atoms being C. Additionally, one or two ring carbon atoms in the heterocyclyl ring can optionally be replaced by a —C(O)— group. More specifically the term heterocyclyl includes, but is not limited to, pyrrolidinyl, piperidinyl, homopiperidinyl, 2-oxopyrrolidinyl, 2-oxopiperidinyl, morpholinyl, piperazinyl, tetrahydro-pyranyl, thiomorpholinyl, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

"Heterocyclylalkyl" or "heterocycloalkyl" means a -(alkylene)-R radical where R is heterocyclyl ring as defined above e.g., tetraydrofuranylmethyl, piperazinylmethyl, morpholinylethyl, and the like.

"Heterocyclylene" means a divalent heterocyclyl, as defined above, unless stated otherwise.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, and S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. When the heteroaryl ring contains 5- or 6 ring atoms it is also referred to herein as 5- or 6-membered heteroaryl.

"Heteroarylene" means a divalent heteroaryl radical.

"Heteroaralkyl" means a -(alkylene)-R radical where R is heteroaryl as defined above, e.g., pyridinylmethyl, and the like. When the heteroaryl ring in heteroaralkyl contains 5- or 6 ring atoms it is also referred to herein as 5- or 6-membered heteroaralkyl.

"Monosubstituted amino" means a —NHR radical where R is alkyl, haloalkyl, hydroxyalkyl, alkoxyalkyl, or alkylcarbonyl, each as defined herein, e.g., methylamino, ethylamino, hydroxyethylamino, methoxyethylamino, aminoethylamino, and the like.

"Optionally substituted aryl" means aryl that is optionally substituted with one, two, or three substituents independently selected from alkyl, hydroxyl, cycloalkyl, carboxy, alkoxycarbonyl, hydroxy, alkoxy, alkylthio, alkylsulfonyl, amino, alkylamino, dialkylamino, halo, haloalkyl, haloalkoxy, and cyano.

"Optionally substituted heteroaryl" means heteroaryl as defined above that is optionally substituted with one, two, or three substituents independently selected from alkyl, alkylthio, alkylsulfonyl, hydroxyl, cycloalkyl, carboxy, alkoxycarbonyl, hydroxy, alkoxy, halo, haloalkyl, haloalkoxy, amino, alkylamino, dialkylamino, and cyano.

"Optionally substituted heterocyclyl" means heterocyclyl as defined above that is optionally substituted with one, two, or three substituents independently selected from alkyl, alkylthio, alkylsulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano.

The term "oxo," as used herein, alone or in combination, refers to =(O).

"Spirocycloalkyl" means a saturated bicyclic ring having 6 to 10 ring carbon atoms wherein the rings are connected through only one atom, the connecting atom is also called the spiroatom, most often a quaternary carbon ("spiro carbon"). The spirocycloalkyl ring is optionally substituted with one or two substituents independently selected from alkyl, halo, alkoxy, hydroxy, and cyano. Representative examples include, but are not limited to, spiro[3.3]heptane, spiro[3.4]octane, spiro[3.5]nonane, spiro[4.4]nonane (1:2:1:1), and the like.

"Spiroheterocyclyl" means a saturated bicyclic ring having 6 to 10 ring atoms in which one, two, or three ring atoms are heteroatom selected from N, O, and $S(O)_n$, where n is an integer from 0 to 2, the remaining ring atoms being C provided at least one ring atom is a heteroatom and the rings are connected through only one atom, the connecting atom is also called the spiroatom, most often a quaternary carbon ("spiro carbon"). The spiroheterocyclyl ring is optionally substituted with one, two, or three substituents independently selected from alkyl, alkylthio, alkylsulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano. Representative examples include, but are not limited to, 2,6-diazaspiro[3.3]heptane, 2,6-diazaspiro[3.4]octane, 2-azaspiro[3.4]octane, 2-azaspiro[3.5]nonane, 2,7-diazaspiro[4.4]nonane, and the like.

"Spiroheterocyclylalkyl" means an -(alkylene)-R radical where R is spiroheterocyclyl as defined above.

When needed, any definition herein may be used in combination with any other definition to describe a composite structural group. By convention, the trailing element of any such definition is that which attaches to the parent moiety. For example, the composite group alkoxyalkyl means that an alkoxy group attached to the parent molecule through an alkyl group.

The present disclosure also includes protected derivatives of compounds of the present disclosure (I). For example, when compounds of the present disclosure contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, 5$^{th}$ Ed., John Wiley & Sons, Inc. (2014), the disclosure of which is incorporated herein by reference in its entirety. The protected derivatives of compounds of the present disclosure can be prepared by methods well known in the art.

The present disclosure also includes polymorphic forms and deuterated forms of the compound of the present disclosure and/or a pharmaceutically acceptable salt thereof.

The term "prodrug" refers to a compound that is made more active in vivo. Certain compounds disclosed herein may also exist as prodrugs, as described, for example, in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the active compound. Prodrugs are often useful because, in some situations, they may be easier to administer than the compound, or parent drug. They may, for instance, be bioavailable by oral administration whereas the parent drug is not. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound. In some embodiments, compounds described herein may be an active compound or active entity of a prodrug compound.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, P A, 1985, which is incorporated herein by reference in its entirety.

The compounds of the present disclosure may have asymmetric centers. Compounds of the present disclosure containing an asymmetrically substituted atom may be isolated in optically active or racemic forms. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. All chiral forms, diastereomeric forms, all mixtures of chiral and/or diastereomeric forms, and racemic forms are within the scope of this disclosure, unless a specific stereochemistry or isomeric form is specifically indicated. It will also be understood by a person of ordinary skill in the art that when a compound is denoted as (R) stereoisomer, it may contain the corresponding (S) stereoisomer as an impurity and vice versa.

In some embodiments, the impurity is present in an amount of ≤ about 15%, ≤ about 10%, ≤ about 5%, ≤ about 2%, or ≤ about 1%.

Certain compounds of the present disclosure can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, and heterocyclyl are substituted, they include all the positional isomers albeit only a few examples are set forth. Furthermore, all hydrates of a compound of the present disclosure are within the scope of this disclosure.

The compounds of the present disclosure may also contain unnatural amounts of isotopes at one or more of the atoms that constitute such compounds and that differ only in the presence of one or more isotopically enriched atoms. Unnatural amounts of an isotope may be defined as ranging from the amount found in nature to an amount 100% of the atom in question. Exemplary isotopes that can be incorporated into compounds of the present invention, such as a compound of Formula (I) (and any embodiment thereof disclosed herein including specific compounds) include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds disclosed herein, including in Table 1 below one or more hydrogen atoms are replaced by $^{2}H$ or $^{3}H$, or one or more carbon atoms are replaced by $^{13}C$—or $^{14}C$-enriched carbon. Positron emitting isotopes such as $^{15}O$, $^{13}N$, $^{11}C$, and $^{5}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass ±10%, preferably ±5%, the recited value and the range is included.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a disease or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease;
(2) inhibiting the disease, i.e., arresting or reducing the development of the disease or its clinical symptoms; or
(3) relieving the disease, i.e., causing regression of the disease or its clinical symptoms.

A "therapeutically effective amount" means the amount of a compound of the present disclosure and/or a pharmaceutically acceptable salt thereof that, when administered to a patient for treating a disease, is sufficient to affect such treatment for the disease. The "therapeutically effective amount" will vary depending on the compound, the disease and its severity and the age, weight, etc., of the mammal to be treated.

The terms "inhibiting" and "reducing," or any variation of these terms in relation of HIF-2a, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of HIF-2α activity compared to normal.

EMBODIMENTS

In further embodiments 1-38 below, the present disclosure includes:
1. In embodiment 1, provided is a compound of Formula (I):

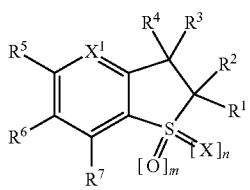

(I)

or a pharmaceutically acceptable salt thereof, where m. n, X, $X^1$, $R^1$, $R^2$, $R^3$, $R^4$, $R^5$, $R^6$, and $R^7$ are as described in the Summary above.

2. In embodiment 2, the compound of embodiment 1 or a pharmaceutically acceptable salt thereof has the structure of formula (II):

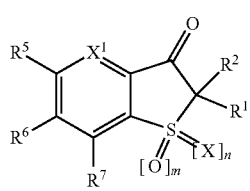

(II)

3. In embodiment 3, the compound of embodiment 1 or a pharmaceutically acceptable salt thereof has the structure of formula (III):

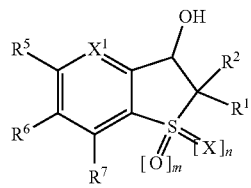

(III)

4. In embodiment 4, the compound of embodiment 1 or a pharmaceutically acceptable salt thereof has the structure of formula (IV):

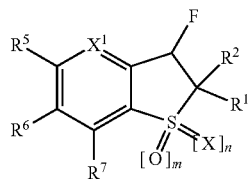

(IV)

5. In embodiment 5, the compound of embodiment 1 or a pharmaceutically acceptable salt thereof has the structure of formula (V):

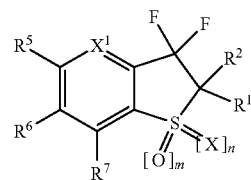

(V)

6. In embodiment 6, the compound of embodiment 1 or a pharmaceutically acceptable salt thereof has the structure of formula (IIa):

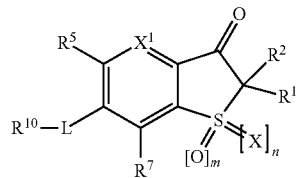

(IIa)

7. In embodiment 7, the compound of embodiment 1 or a pharmaceutically acceptable salt thereof has the structure of formula (IIIa):

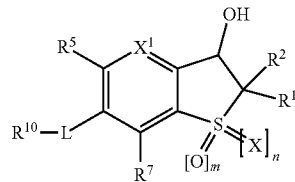

(IIIa)

8. In embodiment 8, the compound of embodiment 1 or a pharmaceutically acceptable salt thereof has the structure of formula (IVa):

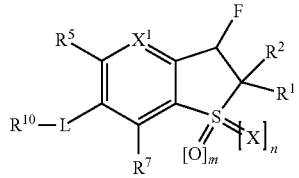

(IVa)

9. In embodiment 9, the compound of embodiment 1 or a pharmaceutically acceptable salt thereof has the structure of formula (Va):

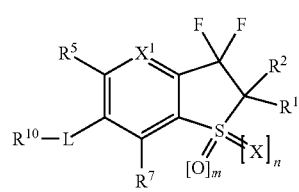

(Va)

10. In embodiment 10, the compound of embodiment 1 or a pharmaceutically acceptable salt thereof has the structure of formula (IIb) or (IIc):

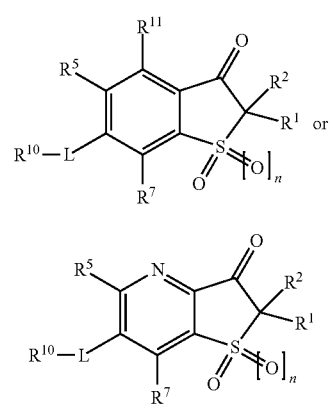

(IIb)

(IIc)

In a first subembodiment of embodiment 10, the compound of formula (IIb) or (IIc) or a pharmaceutically acceptable salt thereof is wherein n is 0. In a second subembodiment of embodiment 10, the compound of formula (IIb) or (IIc) or a pharmaceutically acceptable salt thereof is wherein n is 1. In a third subembodiment, the compound of embodiment 10 and of first and second subembodiments of embodiment 10, or a pharmaceutically acceptable salt thereof is of formula (IIb). In a fourth subembodiment, the compound of embodiment 10 and of first and second subembodiments of embodiment 10, or a pharmaceutically acceptable salt thereof is of formula (IIc).

11. In embodiment 11, the compound of embodiment 1 or a pharmaceutically acceptable salt thereof has the structure of formula (IIIb) or (IIIc):

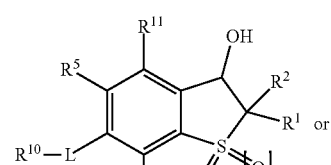

(IIIb)

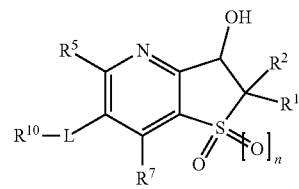

(IIIc)

In a first subembodiment of embodiment 11, the compound of formula (IIIb) or (IIc) or a pharmaceutically acceptable salt thereof is wherein n is 0. In a second subembodiment of embodiment 11, the compound of formula (IIIb) or (IIIc) or a pharmaceutically acceptable salt thereof is wherein n is 1. In a third subembodiment, the compound of embodiment 11 and of first and second subembodiments of embodiment 11, or a pharmaceutically acceptable salt thereof is of formula (IIIb). In a fourth subembodiment, the compound of embodiment 11 and of first and second subembodiments of embodiment 11, or a pharmaceutically acceptable salt thereof is of formula (IIIc).

12. In embodiment 12, the compound of embodiment 1 or a pharmaceutically acceptable salt thereof has the structure of formula (IVb) or (IVc):

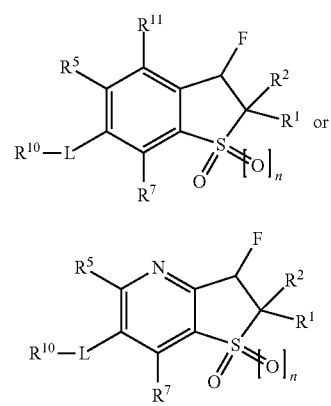

(IVb)

(IVc)

In a first subembodiment of embodiment 12, the compound of formula (IVb) or (IVc) or a pharmaceutically acceptable salt thereof is wherein n is 0. In a second subembodiment of embodiment 12, the compound of formula (IVb) or (IVc) or a pharmaceutically acceptable salt thereof is wherein n is 1. In a third subembodiment, the compound of embodiment 12 and of first and second subembodiments of embodiment 12, or a pharmaceutically acceptable salt thereof is of formula (IVb). In a fourth subembodiment, the compound of embodiment 12 and of first and second subembodiments of embodiment 12, or a pharmaceutically acceptable salt thereof is a compound of formula (IVc).

13. In embodiment 13, the compound of embodiment 1 or a pharmaceutically acceptable salt thereof has the structure of formula (Vb) or (Vc):

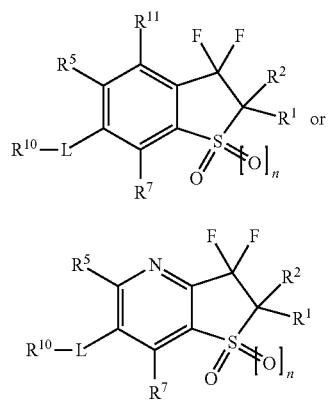

(Vb)

(Vc)

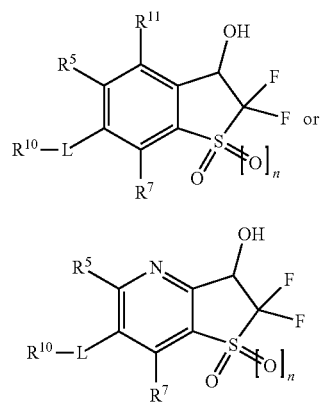

(VIIb)

(VIIc)

In a first subembodiment of embodiment 13, the compound of formula (Vb) or (Vc) or a pharmaceutically acceptable salt thereof is wherein n is 0. In a second subembodiment of embodiment 13, the compound of formula (Vb) or (Vc) or a pharmaceutically acceptable salt thereof is wherein n is 1. In a third subembodiment, the compound of embodiment 13 and of first and second subembodiments of embodiment 13, or a pharmaceutically acceptable salt thereof is of formula (Vb). In a fourth subembodiment, the compound of embodiment 13 and of first and second subembodiments of embodiment 13, or a pharmaceutically acceptable salt thereof is of formula (Vc).

14. In embodiment 14, the compound of embodiment 1 or a pharmaceutically acceptable salt thereof has the structure of formula (VIb) or (VIc):

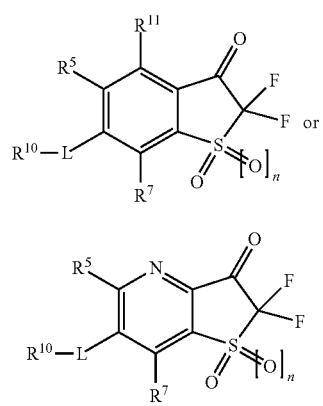

(VIb)

(VIc)

In a first subembodiment of embodiment 14, the compound of formula (VIb) or (VIc) or a pharmaceutically acceptable salt thereof is wherein n is 0. In a second subembodiment of embodiment 14, the compound of formula (VIb) or (VIc) or a pharmaceutically acceptable salt thereof is wherein n is 1. In a third subembodiment, the compound of embodiment 14 and of first and second subembodiments of embodiment 14, or a pharmaceutically acceptable salt thereof is a compound of formula (VIb). In a fourth subembodiment, the compound of embodiment 14 and of first and second subembodiments of embodiment 14, or a pharmaceutically acceptable salt thereof is of formula (VIc).

15. In embodiment 15, the compound of embodiment 1 or a pharmaceutically acceptable salt thereof has the structure of formula (VIIb) or (VIIc):

In a first subembodiment of embodiment 15, the compound of formula (VIIb) or (VIIc) or a pharmaceutically acceptable salt thereof is wherein n is 0. In a second subembodiment of embodiment 15, the compound of formula (VIIb) or (VIIc) or a pharmaceutically acceptable salt thereof is wherein n is 1. In a third subembodiment, the compound of embodiment 15 and of first and second subembodiments of embodiment 15, or a pharmaceutically acceptable salt thereof is of formula (VIIb). In a fourth subembodiment, the compound of embodiment 15 and of first and second subembodiments of embodiment 15, or a pharmaceutically acceptable salt thereof is of formula (VIIc).

16. In embodiment 16, the compound of embodiment 1 or a pharmaceutically acceptable salt thereof has the structure of formula (VIIIb) or (VIIIc):

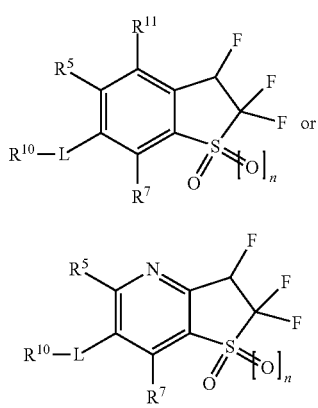

(VIIIb)

(VIIIc)

In a first subembodiment of embodiment 16, the compound of formula (VIIIb) or (VIIIc) or a pharmaceutically acceptable salt thereof is wherein n is 0. In a second subembodiment of embodiment 16, the compound of formula (VIIIb) or (VIIIc) or a pharmaceutically acceptable salt thereof is wherein n is 1. In a third subembodiment, the compound of embodiment 16 and of first and second subembodiments of embodiment 16, or a pharmaceutically acceptable salt thereof is of formula (VIIIb). In a fourth subembodiment, the compound of embodiment 16 and of first and second subembodiments of embodiment 16, or a pharmaceutically acceptable salt thereof is of formula (VIIIc).

17. In embodiment 17, the compound of embodiment 1 or a pharmaceutically acceptable salt thereof has the structure of formula (IXb) or (IXc):

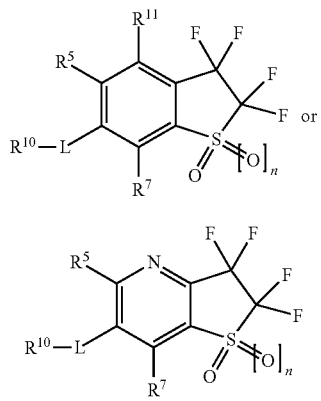

In a first subembodiment of embodiment 17, the compound of formula (IXb) or (IXc) or a pharmaceutically acceptable salt thereof is wherein n is 0. In a second subembodiment of embodiment 17, the compound of formula (IXb) or (IXc) or a pharmaceutically acceptable salt thereof is wherein n is 1. In a third subembodiment, the compound of embodiment 17 and of first and second subembodiments of embodiment 17, or a pharmaceutically acceptable salt thereof is of formula (IXb). In a fourth subembodiment, the compound of embodiment 17 and of first and second subembodiments of embodiment 17, or a pharmaceutically acceptable salt thereof is of formula (IXc).

18. In embodiment 18, the compound of any one of embodiments 1 to 5 or a pharmaceutically acceptable salt thereof is wherein m is 1.

19. In embodiment 19, the compound of any one of embodiments 1 to 5 or a pharmaceutically acceptable salt thereof is wherein m is 1 and n is 0.

20. In embodiment 20, the compound of any one of embodiments 1 to 5 or a pharmaceutically acceptable salt thereof is wherein m is 1 and n is 1 and X is O.

21. In embodiment 21, the compound of any one of embodiments 1 to 5 or a pharmaceutically acceptable salt thereof is wherein m is 1 and n is 1 and X is NR. In a subembodiment of embodiment 21, $R^8$ is H or CN.

22. In embodiment 22, the compound of any one of embodiments 6 to 9 or a pharmaceutically acceptable salt thereof is wherein m is 0 and n is 1 and X is $NR^8$. In a subembodiment of embodiment 22, $R^8$ is H or CN 23. In embodiment 23, the compound of any one of embodiments 1 to 13 and 18-22 or a pharmaceutically acceptable salt thereof is wherein $R^1$ is alkyl or halo and $R^2$ is hydrogen, alkyl, halo, or haloalkyl. In a first subembodiment of embodiment 23, $R^1$ is methyl, ethyl, or fluoro and $R^2$ is hydrogen, methyl, ethyl, fluoro, difluoromethyl or trifluoromethyl. In a second subembodiment of embodiment 23, $R^1$ is fluoro and $R^2$ is hydrogen or fluoro. In a third subembodiment of embodiment 23, $R^1$ is methyl or ethyl and $R^2$ is hydrogen or fluoro.

24. In embodiment 24, the compound of any one of embodiments 1 to 13 and 18-22 or a pharmaceutically acceptable salt thereof is wherein $R^1$ and $R^2$ together with the carbon atom to which they are attached form cycloalkylene or 4 to 6-membered heterocyclylene. In a first subembodiment of embodiment 24, $R^1$ and $R^2$ together with the carbon to which they are attached from cyclopropylene, cyclobutylene, or cyclopentylene. In a second subembodiment of embodiment 24, $R^1$ and $R^2$ together with the carbon atom to which they are attached from oxetan-3-ylene.

25. In embodiment 25, the compound of any one of embodiments 1 and 18-24 or a pharmaceutically acceptable salt thereof is wherein $R^3$ is hydrogen, alkyl, halo, hydroxy, amino, monosubstituted amino, disubstituted amino, or alkoxy and $R^4$ is hydrogen, deuterium, alkyl, or halo. In a first subembodiment of embodiment 25, $R^3$ is methyl, ethyl, fluoro, or hydroxy and $R^4$ is hydrogen, methyl, deuterium ethyl, fluoro, difluoromethyl or trifluoromethyl. In a second subembodiment of embodiment 25, $R^3$ is fluoro and $R^4$ is hydrogen or fluoro. In a third subembodiment of embodiment 25, $R^3$ and $R^4$ are fluoro. In a fourth subembodiment of embodiment 25, $R^3$ is hydrogen and $R^4$ is hydroxy.

26. In embodiment 26, the compound of any one of embodiments 1 and 18-24 or a pharmaceutically acceptable salt thereof is wherein $R^3$ and $R^4$ together with the carbon to which they are attached form oxo.

27. In embodiment 27, the compound of any one of embodiments 1 and 18-24 or a pharmaceutically acceptable salt thereof is wherein $R^3$ and $R^4$ together with the carbon to which they are attached form cycloalkylene, preferably cyclopropylene, cyclobutylene, or cyclopentylene.

28. In embodiment 28, the compound of any one of embodiments 1 and 18-24 or a pharmaceutically acceptable salt thereof is wherein $R^3$ and $R^4$ together with the carbon to which they are attached form 4 to 6 membered heterocyclylene, preferably oxetan-3-ylene or pyran-3ylene.

29. In embodiment 29, the compound of any one of embodiments 1 to 5 and 18-28 or a pharmaceutically acceptable salt thereof is wherein $R^6$ is -L-$R^{10}$. In a first subembodiment of embodiment 29, $X^1$ is N. In a second subembodiment of embodiment 29, $X^1$ is $CR^{11}$.

30. In embodiment 30, the compound of any one of embodiments 1 to 5 and 18-28 or a pharmaceutically acceptable salt thereof is wherein $X^1$ is C-$L^1$-$R^{12}$. In a first subembodiment of embodiment 30, $L^1$ is O. In a second subembodiment of embodiment 30, $L^1$ is S. In a third subembodiment of embodiment 30, $L^1$ is NH.

31. In embodiment 31, the compound of any one of embodiments 6 to 17 and 29 or a pharmaceutically acceptable salt thereof is wherein L is O, S, or NH. In a first subembodiment of embodiment 31, L is O. In a second subembodiment of embodiment 31, L is S. In a third subembodiment of embodiment 31, L is NH.

32. In embodiment 32, the compound of any one of embodiments 1 to 31 or a pharmaceutically acceptable salt thereof is wherein $R^5$ is hydrogen, methyl, ethyl, methoxy, fluoro, cyano, trifluoromethyl, or trifluoromethoxy. In a first subembodiment of embodiment 32, $R^5$ is hydrogen.

33. In embodiment 33, the compound of any one of embodiments 1 to 32 or a pharmaceutically acceptable salt thereof is wherein $R^7$ is hydrogen, methyl, ethyl, methoxy, fluoro, bromo, cyano, cyclopropyl, trifluoromethyl, difluoromethyl, difluoromethoxy, trifluoromethoxy, or methylsulfonyl. In a first subembodiment of embodiment 33, $R^7$ is hydrogen, difluoromethyl, difluoromethoxy, trifluoromethyl, or trifluoromethoxy. In a first subembodiment of embodiment 33, $R^7$ is difluoromethyl.

34. In embodiment 34, the compound of any one of embodiments 1 to 33 or a pharmaceutically acceptable salt thereof is wherein $R^{11}$ is hydrogen, alkyl, halo, haloalkyl, cyano, hydroxyalkyl, alkoxyalkyl, or aminoalkyl. In a first subembodiment of embodiment 33, $R^{11}$ is hydrogen.

35. In embodiment 35, the compound of any one of embodiments 1 to 34 or a pharmaceutically acceptable salt thereof is wherein $R^{10}$ is phenyl substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl; and $R^{12}$ is phenyl substituted with $R^d$, $R^e$, and/or $R^f$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl. In a first subembodiment of embodiment 35, $R^a$, $R^b$, $R^c$, $R^d$, $R^e$, and $R^f$ are independently selected from hydrogen, alkyl, alkoxy, hydroxy, halo, haloalkyl, haloalkoxy, and cyano. In a second subembodiment of Embodiment 35, $R^a$, $R^b$, $R^c$, $R^d$, $R^e$, and $R^f$ are independently selected from hydrogen, methyl, methoxy, hydroxy, chloro, fluoro, cyano, difluoromethyl, trifluoromethyl, difluoromethoxy, and trifluoromethoxy. In a third subembodiment of Embodiment 35, $R^{10}$ and $R^{12}$ are independently 3-chloro-5-fluorophenyl, 3,5-difluorophenyl, 3-fluoro-5-methoxyphenyl, 3-cyano-5-fluorophenyl, 3-chloro-4-fluorophenyl, 3-cyanophenyl, 3-trifluoromethylphenyl, 3,4-dichlorophenyl, 3-chloro-2-methylphenyl, 3,5-dichlorophenyl, 3,5-dimethylphenyl, 2-chloro-6-methylphenyl, 2,6-difluorophenyl, 3,4,5-trifluorophenyl, 3,4-difluorophenyl, 4-fluoro-3-methylphenyl, 3-cyano-4-fluorophenyl, or 3-cyano-5-difluoromethylphenyl. In a fourth subembodiment of Embodiment 35, $R^{10}$ and $R^{12}$ are independently 3-cyano-5-fluorophenyl.

36. In embodiment 36, the compound or a pharmaceutically acceptable salt thereof of any one of embodiments 1 to 34 is wherein $R^{10}$ and $R^{12}$ are independently cycloalkyl or cycloalkylalkyl each optionally substituted with one or two substituents independently selected from alkyl, halo, alkoxy, cyano, and hydroxy. In a first subembodiment of embodiment 36, $R^{10}$ and $R^{12}$ are independently cyclopropylmethyl, cyclopropylethyl, cyclobutylmethyl, cyclobutylethyl, cyclopentylmethyl, cyclopentylethyl, or cyclohexylmethyl, each optionally substituted with one or two substituents independently selected from alkyl, halo, alkoxy, cyano, and hydroxy. In a second subembodiment of Embodiment 36, $R^{10}$ and $R^{12}$ are independently cyclopropylmethyl, cyclopropylethyl, cyclobutylmethyl, cyclobutylethyl, cyclopentylmethyl, cyclopentylethyl, or cyclohexylmethyl, each independently substituted with one or two substituents independently selected from hydrogen, methyl, methoxy, cyano, and fluoro, preferably $R^{10}$ and $R^{12}$ are independently cyclopropylmethyl,1-cyanocyclopropylmethyl, cyclobutylmethyl or 1-cyanocyclobutylmethyl. In a third subembodiment of embodiment 36, $R^{10}$ and $R^{12}$ are independently cyclopropyl, cyclobutyl, cyclopentyl, or cyclohexyl, each optionally substituted with one or two substituents independently selected from alkyl, halo, alkoxy, cyano, and hydroxy. In a fourth subembodiment of Embodiment 36, $R^{10}$ and $R^{12}$ are independently cyclopropyl, cyclobutyl, cyclopentyl, or cyclohexyl, each optionally substituted with one or two substituents independently selected from methyl, cyano, methoxy, and fluoro, preferably, $R^{10}$ and $R^{12}$ are independently cyclobutyl, 3,3-difluorocyclobutyl, or 3-cyano-3-methylcyclobutyl.

37. In embodiment 37, the compound or a pharmaceutically acceptable salt thereof of any one of embodiments 1 to 34 is wherein $R^{10}$ is heteroaryl substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl; and $R^{12}$ is heteroaryl substituted with $R^d$, $R^e$, and/or $R^f$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl. In a first subembodiment of embodiment 37, $R^{10}$ and $R^{12}$ are independently 5- or 6-membered heteroaryl e.g., pyridyl, pyridazinyl, pyrimidinyl, thienyl, furanyl, thiazolyl, oxazolyl, imidazolyl, or pyrazinyl substituted with $R^a$, $R^b$, and/or $R^c$ and $R^d$, $R^e$, and/or $R^f$ respectively, wherein $R^a$, $R^b$, $R^d$ and $R^e$ are independently selected from hydrogen, alkyl, alkoxy, hydroxy, halo, haloalkyl, haloalkoxy, and cyano and $R^c$ and $R^f$ are independently selected from hydrogen, alkyl, halo, haloalkyl, or haloalkoxy. In a second subembodiment of Embodiment 37, $R^{10}$ and $R^{12}$ are independently pyridin-3-yl, pyridin-2-yl, pyridazin-3-yl, pyridazin-4-yl, pyrimidin-5-yl, pyrimidin-2-yl, thien-2-yl, furan-2-yl, thiazol-5-yl, oxazol-5-yl, imidazol-5-yl, furan-3-yl thien-3-yl, thiazol-4-yl, pyridin-4-yl, oxazol-2-yl, imidazol-2-yl, pyridin-2-yl, pyrazin-2-yl or thiazol-2-yl, substituted with $R^a$, $R^b$, and/or $R^c$ and $R^d$, $R^e$, and/or $R^f$ respectively, wherein $R^a$, $R^b$, $R^d$ and $R^e$ are independently selected from hydrogen, methyl, methoxy, hydroxy, chloro, fluoro, difluoromethyl, trifluoromethyl, difluoromethoxy, and trifluoromethoxy and $R^c$ and $R^f$ are independently selected from hydrogen, methyl, cyano, chloro, fluoro, difluoromethyl, trifluoromethyl, difluoromethoxy, or trifluoromethoxy. In a third subembodiment of Embodiment 37, $R^{10}$ and $R^{12}$ are independently 5-cyanopyridin-3-yl, 5-chloropyridin-3-yl, or 5-fluoropyridin-3-yl.

38. In embodiment 38, the compound or a pharmaceutically acceptable salt thereof of any one of embodiments 1-23 is wherein $R^{10}$ and $R^{12}$ are independently bicyclic heteroaryl substituted with $R^a$, $R^b$, and/or $R^c$ and $R^d$, $R^e$, and/or $R^f$ respectively, wherein $R^a$, $R^b$, $R^d$ and $R^e$ are independently selected from hydrogen, alkyl, alkoxy, hydroxy, halo, haloalkyl, haloalkoxy, and cyano and $R^c$ and $R^f$ are independently selected from hydrogen, alkyl, halo, haloalkyl, haloalkoxy, hydroxyalkyl, alkoxyalkyl, and aminoalkyl.

39. In embodiment 39, the compound or a pharmaceutically acceptable salt thereof of any one of embodiments 1 to 34 is wherein $R^{10}$ and $R^{12}$ are independently heterocyclyl, wherein heterocyclyl is substituted with $R^a$, $R^b$, and/or $R^c$ and $R^d$, $R^e$, and/or $R^f$ respectively wherein $R^a$ and $R^b$ and $R^d$ and $R^e$ are independently selected from hydrogen, alkyl, alkoxy, hydroxy, halo, haloalkyl, haloalkoxy, and cyano and $R^c$ and $R^f$ are independently hydrogen, alkyl, halo, haloalkyl, haloalkoxy, hydroxyalkyl, alkoxyalkyl, or aminoalkyl. In a first subembodiment of embodiment 39, $R^{10}$ and $R^{12}$ are independently tetrahydrofuranyl, tetrahydrohydropyranyl, or oxetanyl independently substituted with $R^a$ and $R^b$ and $R^d$ and $R^e$ respectively wherein $R^a$, $R^b$, $R^d$ and $R^e$ are independently selected from hydrogen, methyl, and fluoro.

40. In embodiment 40, the compound or a pharmaceutically acceptable salt thereof of any one of embodiments 1 to 34 is wherein $R^{10}$ and $R^{12}$ are independently spiroheterocyclyl.

Representative compounds of the disclosure made are disclosed in Table 1 below:

TABLE 1

| Cpd. # | structure | Compound name |
| --- | --- | --- |
| 1 | 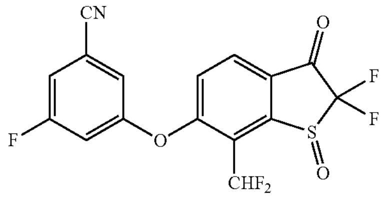 [SMILES: N#Cc1cc(F)cc(Oc2ccc3c(c2C(F)F)S(=O)C(F)(F)C3=O)c1] | 3-((7-difluoromethyl)-2,2-difluoro-1-oxido-3-oxo-2,3-dihydrobenzo[b]thiophen-6-y1)oxy)-5-flurorobenzonitrile |
| 2 | 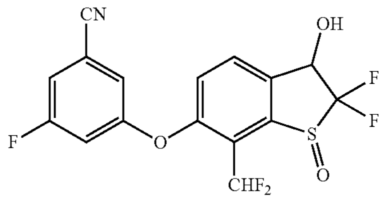 [SMILES: N#Cc1cc(F)cc(Oc2ccc3c(c2C(F)F)S(=O)C(F)(F)C3O)c1] | 3-((7-(difluoromethyl)-2,2-difluoro-3-hydroxy-1-oxido-2,3-dihydrobenzo[b]thiophen-6-yl)oxy)-5-fluorobenzonitrile |
| 3a | 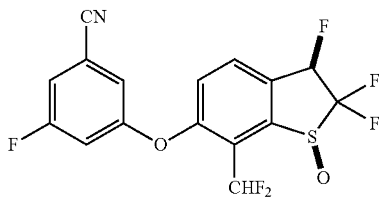 | a mixture of 3-(((1S,3R)-7-(difluoromethyl)-2,2,3-trifluoro-1-oxido-2,3-dihydrobenzo-[b]thiophen-6-yl)oxy)-5-fluorobenzonitrile and 3-(((1R,3S)-7-(difluoromethyl)-2,2,3-trifluoro-1-oxido-2,3-dihydrobenzo[b]thiophen-6-yl)oxy)-5-fluorobenzonitrile or |
| 3b | 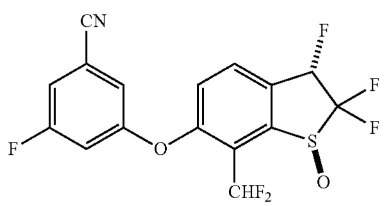 | a mixture of 3-(((1S,3S)-7-(difluoromethyl)-2,2,3-trifluoro-1-oxido-2,3-dihydrobenzo-[b]thiophen-6-yl)oxy)-5-fluorobenzonitrile and 3-(((1R,3R)-7-(difluoromethyl)-2,2,3-trifluoro-1-oxido-2,3-dihydrobenzo[b]thiophen-6-yl)oxy)-5-fluorobenzonitrile |
| 4 | 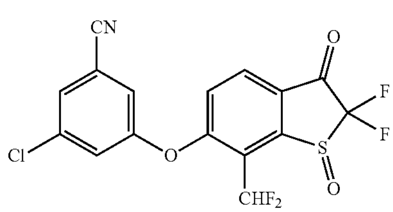 [SMILES: N#Cc1cc(Cl)cc(Oc2ccc3c(c2C(F)F)S(=O)C(F)(F)C3=O)c1] | 3-chloro-5-((7-(difluoromethyl)-2,2-difluoro-1-oxido-3-oxo-2,3-dihydrobenzo[b]thiophen 6-yl)oxy)benzonitrile |

TABLE 1-continued

| Cpd. # | structure | Compound name |
|---|---|---|
| 5 | 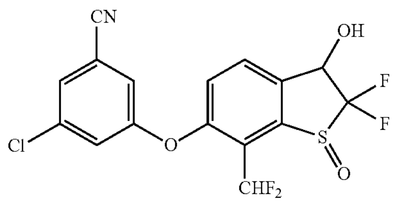 [SMILES: N#Cc1cc(Cl)cc(Oc2ccc3c(c2C(F)F)S(=O)C(F)(F)C3O)c1] | 3-chloro-5-((7-(difluoromethyl)-2,2-difluoro-3-hydroxy-1-oxido-2,3-dihydrobenzo[b]thiophen-6-yl)oxy)benzonitrile |
| 6a | 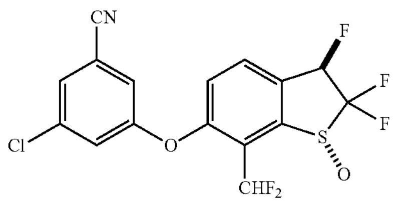 | 3-chloro-5-(((1R,3R)-7-(difluoromethyl)-2,2,3-trifluoro-1-oxido-2,3-dihydrobenzo[b]-thiophen-6-yl)oxy)benzonitrile; |
| 6b | 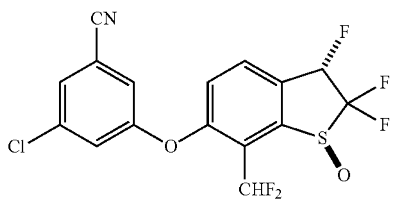 | 3-chloro-5-(((1S,3S)-7-(difluoromethyl)-2,2,3-trifluoro-1-oxido-2,3-dihydrobenzo[b]-thiophen-6-yl)oxy)benzonitrile |
| 6c | 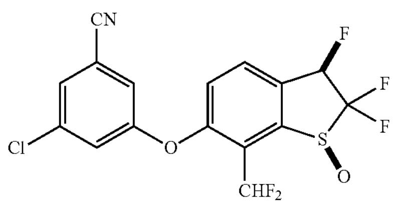 | 3-chloro-5-(((1S,3R)-7-(difluoromethyl)-2,2,3-trifluoro-1-oxido-2,3-dihydrobenzo[b]-thiophen-6-yl)oxy)benzonitrile |
| 6d | 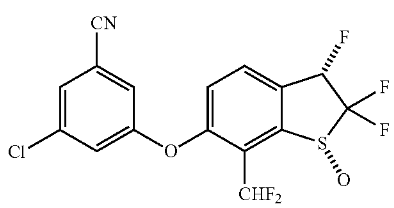 | 3-chloro-5-(((1R,3S)-7-(difluoromethyl)-2,2,3-trifluoro-1-oxido-2,3-dihydrobenzo[b]-thiophen-6-yl)oxy)benzonitrile |
| 7 | 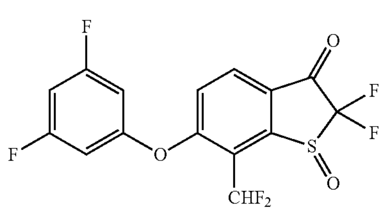 [SMILES: O=C1c2ccc(Oc3cc(F)cc(F)c3)c(C(F)F)c2S(=O)C1(F)F] | 7-(difluoromethyl)-6-(3,5-difluorophenoxy)-2,2-difluorobenzo[b]thiophen-3(2H)-one 1-oxide |
| 8 | 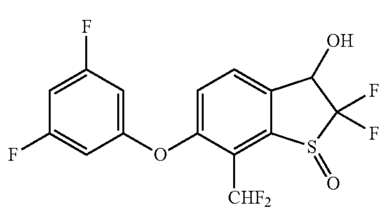 [SMILES: O=S1c2c(ccc(Oc3cc(F)cc(F)c3)c2C(F)F)C(O)C1(F)F] | 7-(difluoromethyl)-6-(3,5-difluorophenoxy)-2,2-difluoro-3-hydroxy-2,3-dihydrobenzo[b]thiophene 1-oxide |

TABLE 1-continued

| Cpd. # | structure | Compound name |
|---|---|---|
| 9a | 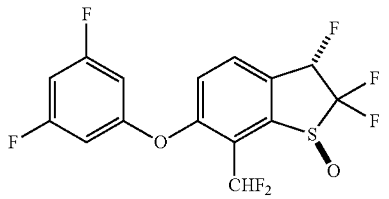 | (1S,3S)-7-(difluoromethyl)-6-(3,5-difluorophenoxy)-2,2,3-trifluoro-2,3-dihydrobenzo[b]-thiophene 1-oxide |
| 9b | 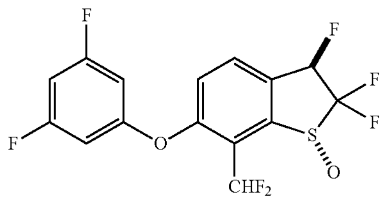 | (1R,3R)-7-(difluoromethyl)-6-(3,5-difluorophenoxy)-2,2,3-trifluoro-2,3-dihydrobenzo[b]-thiophene 1-oxide |
| 9c | 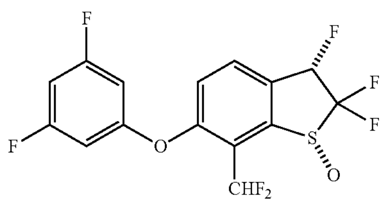 | (1R,3S)-7-(difluoromethyl)-6-(3,5-difluorophenoxy)-2,2,3-trifluoro-2,3-dihydrobenzo[b]-thiophene 1-oxide |
| 9d | 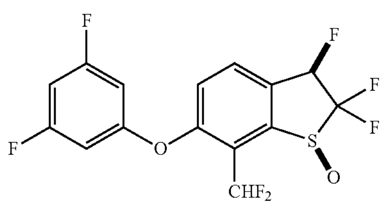 | (1S,3R)-7-(difluoromethyl)-6-(3,5-difluorophenoxy)-2,2,3-trifluoro-2,3-dihydrobenzo[b]-thiophene 1-oxide |
| 10 | 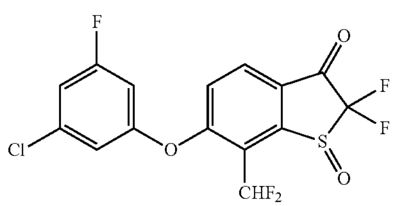 [SMILES: O=C1c2ccc(Oc3cc(F)cc(Cl)c3)c(C(F)F)c2S(=O)C1(F)F] | 6-(3-chloro-5-fluorophenoxy)-7-(difluoromethyl)-2,2-difluorobenzo[b]thiophen-3(2H)-one 1-oxide |
| 11 | 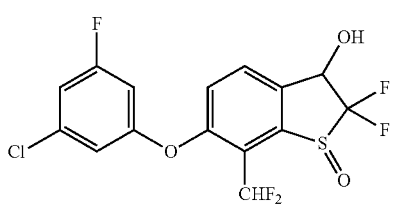 [SMILES: O=S1c2c(ccc(Oc3cc(F)cc(Cl)c3)c2C(F)F)C(O)C1(F)F] | 6-(3-chloro-5-fluorophenoxy)-7-(difluoromethyl)-2,2-difluoro-3-hydroxy-2,3-dihydrobenzo[b]thiophene 1-oxide |
| 12a | 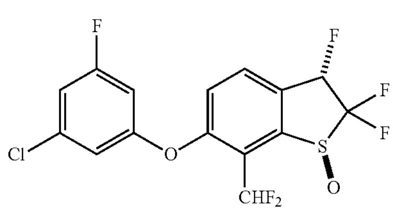 | (1S,3S)-6-(3-chloro-5-fluorophenoxy)-7-(difluoromethyl)-2,2,3-trifluoro-2,3-dihydrobenzo[b]thiophene 1-oxide |

TABLE 1-continued

| Cpd. # | structure | Compound name |
|---|---|---|
| 12b | 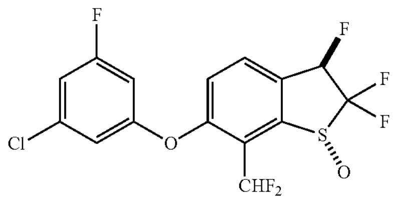 | (1R,3R)-6-(3-chloro-5-fluorophenoxy)-7-(difluoromethyl)-2,2,3-trifluoro-2,3-dihydrobenzo[b]thiophene 1-oxide |
| 12c | 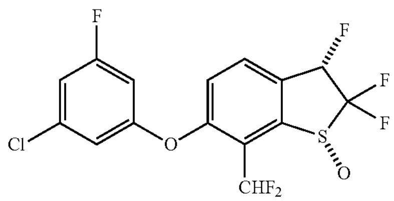 | (1R,3S)-6-(3-chloro-5-fluorophenoxy)-7-(difluoromethyl)-2,2,3-trifluoro-2,3-dihydrobenzo[b]thiophene 1-oxide |
| 12d | 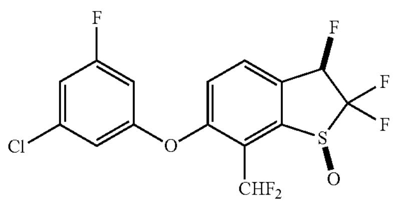 | (1S,3R)-6-(3-chloro-5-fluorophenoxy)-7-(difluoromethyl)-2,2,3-trifluoro-2,3-dihydrobenzo[b]thiophene 1-oxide |
| 13a | 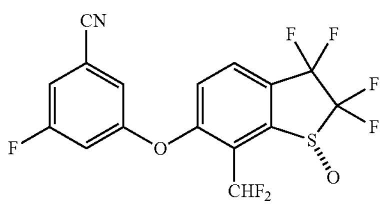 | (R)-3-((7-(difluoromethyl)-2,2,3,3-tetrafluoro-1-oxido-2,3-dihydrobenzo[b]thiophen-6-yl)oxy)-5-fluorobenzonitrile |
| 13b | 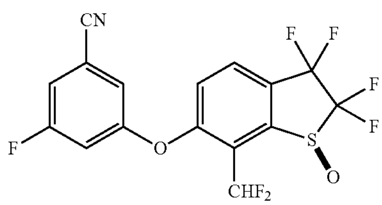 | (S)-3-((7-(difluoromethyl)-2,2,3,3-tetrafluoro-1-oxido-2,3-dihydrobenzo[b]thiophen-6-yl)oxy)-5-fluorobenzonitrile |
| 14 | 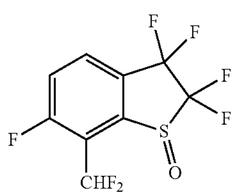 [SMILES: O=S1c2c(ccc(F)c2C(F)F)C(F)(F)C1(F)F] | 7-(difluoromethyl)-2,2,3,3,6-pentafluoro-2,3-dihydrobenzo[b]thiophene 1-oxide |
| 15 | 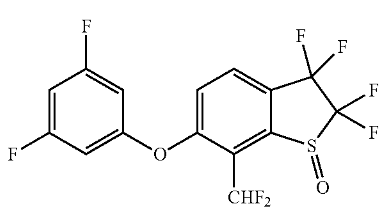 [SMILES: O=S1c2c(ccc(Oc3cc(F)cc(F)c3)c2C(F)F)C(F)(F)C1(F)F] | 7-(difluoromethyl)-6-(3,5-difluorophenoxy)-2,2,3,3-tetrafluoro-2,3-dihydrobenzo[b]-thiophene 1-oxide |

TABLE 1-continued

| Cpd. # | structure | Compound name |
|---|---|---|
| 16 | 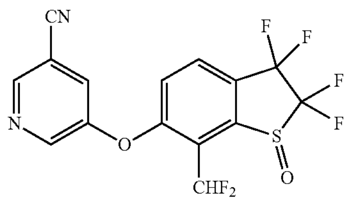 [SMILES: O=S1c2c(ccc(Oc3cncc(Cl)c3)c2C(F)F)C(F)(F)C1(F)F] | 5-((7-(difluoromethyl)-2,2,3,3-tetrafluoro-1-oxido-2,3-dihydrobenzo[b]thiophen-6-yl)oxy)nicotinonitrile |
| 17 | 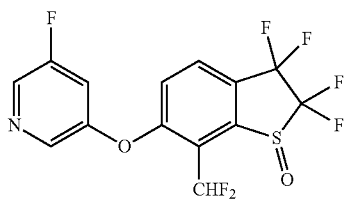 | 7-(difluoromethyl)-2,2,3,3-tetrafluoro-6-((5-fluoropyridin-3-yl)oxy)-2,3-dihydrobenzo-[b]thiophene 1-oxide |
| 18 | 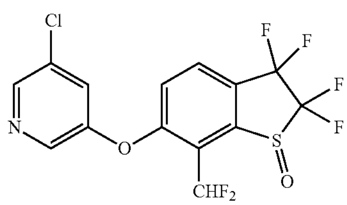 | 6-((5-chloropyridin-3-yl)oxy)-7-(difluoromethyl)-2,2,3,3-tetrafluoro-2,3-dihydrobenzo-[b]thiophene 1-oxide |
| 19 | 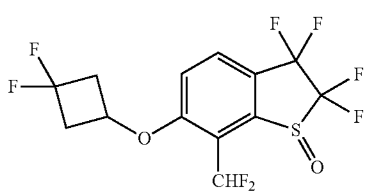 [SMILES: O=S1c2c(ccc(OC3CC(F)(F)C3)c2C(F)F)C(F)(F)C1(F)F] | 6-(3,3-difluorocyclobutoxy)-7-(difluoromethyl)-2,2,3,3-tetrafluoro-2,3-dihydrobenzo[b]-thiophene 1-oxide |
| 20 | 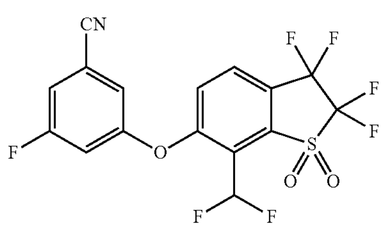 [SMILES: N#Cc1cc(F)cc(Oc2ccc3c(c2C(F)F)S(=O)(=O)C(F)(F)C3(F)F)c1] | 3-((7-(difluoromethyl)-2,2,3,3-tetrafluoro-1,1-dioxido-2,3-dihydrobenzo[b]thiophen-6-yl)oxy)-5-fluorobenzonitrile |
| 21 | 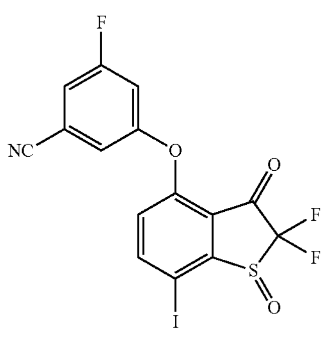 [SMILES: N#Cc1cc(F)cc(Oc2ccc(I)c3c2C(=O)C(F)(F)S3=O)c1] | 3-((2,2-difluoro-7-iodo-1-oxido-3-oxo-2,3-dihydrobenzo[b]thiophen-4-yl)oxy)-5-fluorobenzonitrile |

TABLE 1-continued

| Cpd. # | structure | Compound name |
|---|---|---|
| 22 | 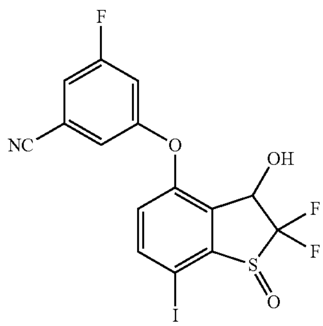 [SMILES: N#Cc1cc(F)cc(Oc2ccc(I)c3c2C(O)C(F)(F)S3=O)c1] | 3-((2,2-difluoro-3-hydroxy-7-iodo-1-oxido-2,3-dihydrobenzo[b]thiophen-4-yl)oxy)-5-fluorobenzonitrile |
| 23 | 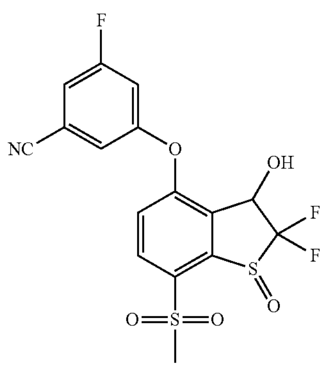 [SMILES: CS(=O)(=O)c1ccc(Oc2cc(F)cc(C#N)c2)c2c1S(=O)C(F)(F)C2O] | 3-((2,2-difluoro-3-hydroxy-7-(methylsulfonyl)-1-oxido-2,3-dihydrobenzo[b]thiophen-4-yl)oxy)-5-fluorobenzonitrile |
| 24a | and | a mixture of 3-fluoro-5-(((1S,3R)-2,2,3-trifluoro-7-(methylsulfonyl)-1-oxido-2,3-dihydrobenzo[b]thiophen-4-yl)oxy)benzonitrile and 3-fluoro-5-(((1R,3S)-2,2,3-trifluoro-7-(methylsulfonyl)-1-oxido-2,3-dihydrobenzo[b]thiophen-4-yl)oxy)benzonitrile | and

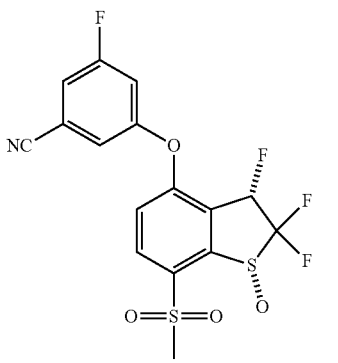

TABLE 1-continued

| Cpd. # | structure | Compound name |
|---|---|---|
| 24b | 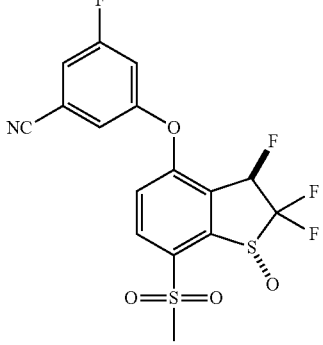 and 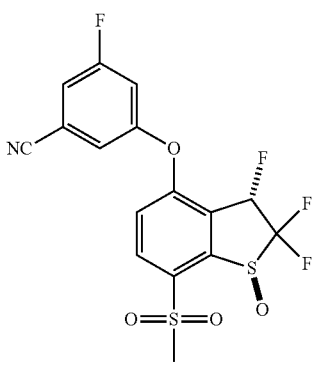 | a mixture of 3-fluoro-5-(((1R,3R)-2,2,3-trifluoro-7-(methylsulfonyl)-1-oxido-2,3-dihydrobenzo[b]thiophen-4-yl)oxy)benzonitrile and 3-fluoro-5-(((1S,3S)-2,2,3-trifluoro-7-(methylsulfonyl)-1-oxido-2,3-dihydrobenzo[b]thiophen-4-yl)oxy)benzonitrile |
| 25 | 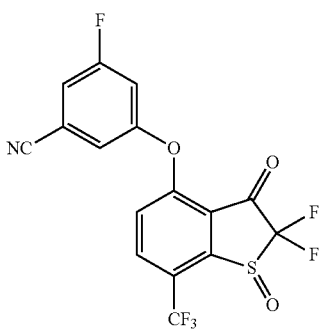 [SMILES: N#Cc1cc(F)cc(Oc2ccc(C(F)(F)F)c3c2C(=O)C(F)(F)S3=O)c1] | 3-((2,2-difluoro-1-oxido-3-oxo-7-(trifluoromethyl)-2,3-dihydrobenzo[b]thiophen-4-yl)oxy)-5-fluorobenzonitrile |
| 26 | 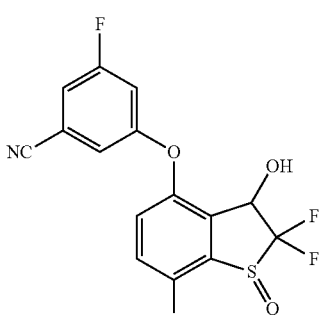 | 3-((2,2-difluoro-3-hydroxy-1-oxido-7-(trifluoromethyl)-2,3-dihydrobenzo[b]thiophen-4-yl)oxy)-5-fluorobenzonitrile |

TABLE 1-continued

| Cpd. # | structure | Compound name |
|---|---|---|
| 27a | 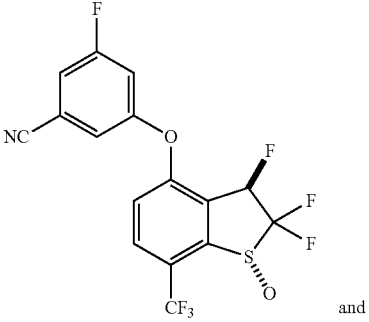 and 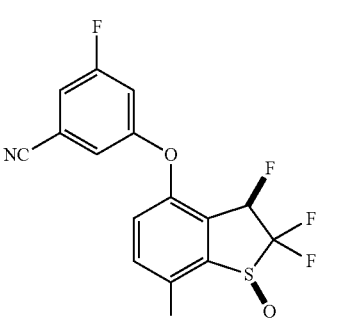 | a mixture of 3-fluoro-5-(((1R,3R)-2,2,3-trifluoro-1-oxido-7-(trifluoromethyl)-2,3-dihydrobenzo[b]thiophen-4-yl)oxy)benzonitrile and 3-fluoro-5-(((1S,3S)-2,2,3-trifluoro-1-oxido-7-(trifluoromethyl)-2,3-dihydrobenzo[b]thiophen-4-yl)oxy)benzonitrile |
| 27b | 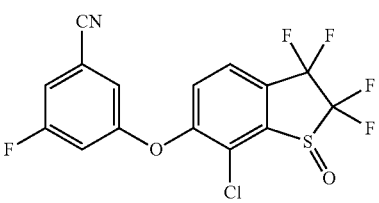 [SMILES: N#Cc1cc(F)cc(Oc2ccc3c(c2Cl)S(=O)C(F)(F)C3(F)F)c1] and | a mixture of 3-fluoro-5-(((1S,3R)-2,2,3-trifluoro-1-oxido-7-(trifluoromethyl)-2,3-dihydrobenzo[b]thiophen-4-yl)oxy)benzonitrile and 3-fluoro-5-(((1R,3S)-2,2,3-trifluoro-1-oxido-7-(trifluoromethyl)-2,3-dihydrobenzo[b]thiophen-4-yl)oxy)benzonitrile |
| 28 | 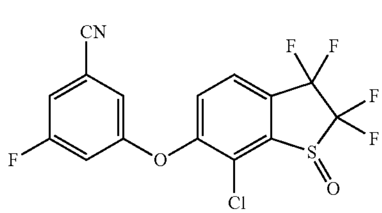 | 3-((7-chloro-2,2,3,3-tetrafluoro-1-oxido-2,3-dihydrobenzo[b]thiophen-6-yl)oxy)-5-fluorobenzonitrile |

TABLE 1-continued

| Cpd. # | structure | Compound name |
|---|---|---|
| 29 | | 3-((7-chloro-2,2,3,3-tetrafluoro-1,1-dioxido-2,3-dihydrobenzo[b]thiophen-6-yl)oxy)-5-fluorobenzonitrile |
| 29 | | 3-((7-chloro-2,2,3,3-tetrafluoro-1,1-dioxido-2,3-dihydrobenzo[b]thiophen-6-yl)oxy)-5-fluorobenzonitrile |
| 30 | 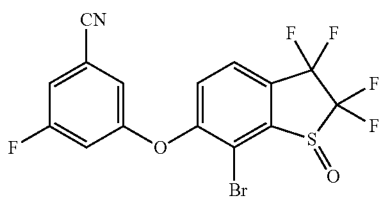 [SMILES: N#Cc1cc(F)cc(Oc2ccc3c(c2Br)S(=O)C(F)(F)C3(F)F)c1] | 3-((7-bromo-2,2,2,3-tetrafluoro-1-oxido-2,3-dihydrobenzo[b]thiophen-6-yl)oxy)-5-fluorobenzonitrile |
| 31 | 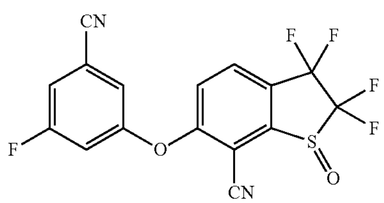 [SMILES: N#Cc1cc(F)cc(Oc2ccc3c(c2C#N)S(=O)C(F)(F)C3(F)F)c1] | 6-(3-cyano-5-fluorophenoxy)-2,2,3,3-tetrafluoro-2,3-dihydrobenzo[b]thiophene-7-carbonitrile 1-oxide |
| 32 | 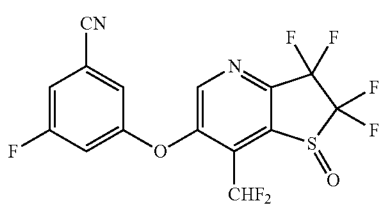 | 3-((7-(difluoromethyl)-2,2,3,3-tetrafluoro-1-oxido-2,3-dihydrothieno[3,2-b]pyridin-6-yl)oxy)-5-fluorobenzonitrile |
| 33 | 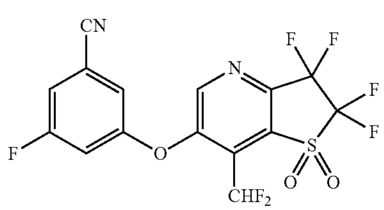 [SMILES: N#Cc1cc(F)cc(Oc2cnc3c(c2C(F)F)S(=O)(=O)C(F)(F)C3(F)F)c1] | 3-((7-(difluoromethyl)-2,2,3,3-tetrafluoro-1,1-dioxido-2,3-dihydrothieno[3,2-b]pyridin-6-yl)oxy)-5-fluorobenzonitrile |

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compounds of Formula (I) where $R^1$ and $R^2$ are independently hydrogen or halo, $X^1$ is $CR^{11}$ where $R^{11}$ is as defined in the Summary, $R^3$ is hydrogen, halo, or hydroxy, $R^4$ is hydrogenalkyl, or halo or $R^3$ and $R^4$ together with the carbon to which they are attached form oxo; $R^6$ is other than hydrogen; and $R^5$ and $R^7$ are as defined in the Summary can be prepared as illustrated and described in Scheme 1 below.

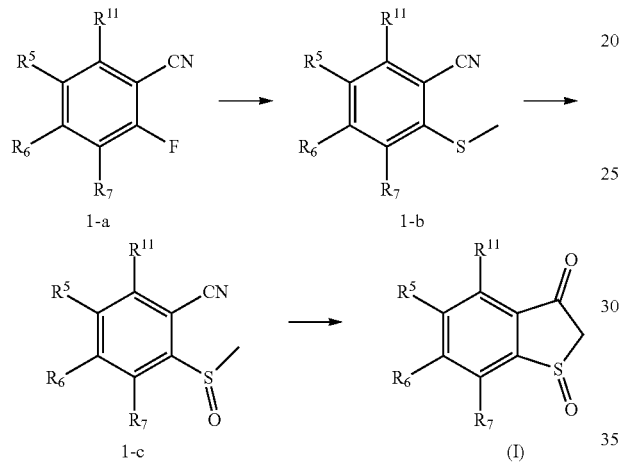

Scheme 1

Displacement of fluoro in a compound of formula 1-a where $R^5$, $R^6$, $R^7$, and $R^{11}$ are defined above, with thiomethoxide provides a compound of formula 1-b. The reaction is carried out in a polar, organic solvent such as acetonitrile. Compounds of formula 1-a are commercially available or they can be prepared by methods well known in the art. For example, 4-bromo-2-fluorobenzonitrile and 2,4-difluorobenzonitrile are commercially available. Compounds of formula 1-a where $R^7$ is haloalkyl can be prepared treating compound 1-a with LDA in DMF and treating the resulting formylbenzonitrile with a halogenating agent. Compounds of formula 1-a where $R^6$ is -L-$R^{10}$ can be prepared treating compound 1-a where $R^6$ is fluoro with a compound of formula $R^{10}$-LH where L is N, O, or S and $R^{10}$ is a defined in the Summary under alkylating or arylating conditions well known in the art. Compounds of formula $R^{10}$-LH are commercially available or they can be prepared by methods well known in the art. For example, 3-fluoro-5-hydroxybenzonitrile, 3,5-difluorophenol, 3-chloro-5-fluorophenol, 3-chloro-5-hydroxybenzonitrile, 5-fluoropyridin-3-ol, 5-chloropyridin-3-ol, 5-hydroxynicotinonitrile, 3-fluoro-5-mercaptobenzonitrile, 3-amino-5-fluorobenzonitrile, 3,3-difluorocyclobutan-1-ol are commercially available.

Treatment of compound 1-b with a suitable oxidizing agent such as Oxone, followed by cyclization of the resulting sulfoxide of formula 1-c provides a compound of Formula (I) where F and $R^4$ together with the carbon to which they are attached form oxo. Cyclization can be achieved by treating compound 1-c with an organic base such as LDA in an organic solvent such as tetrahydrofuran.

Compounds of Formula (I) can be converted to other compounds of Formula (I). Some illustrative examples are provided below.

Method (i)

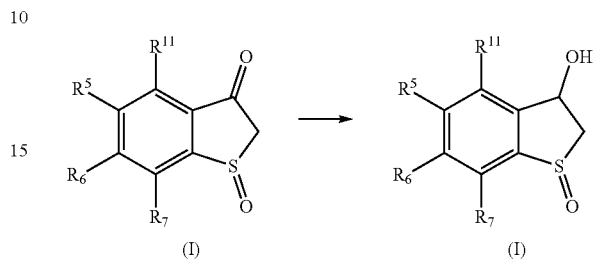

A compound of Formula (I) where $R^3$ and $R^4$ together with the carbon to which they are attached form oxo can be converted to a corresponding compound of Formula (I) where $R^3$ is hydroxy and $R^4$ is hydrogen by treating it with a suitable reducing agent such as sodium borohydride under conditions well known in the art.

Method (ii)

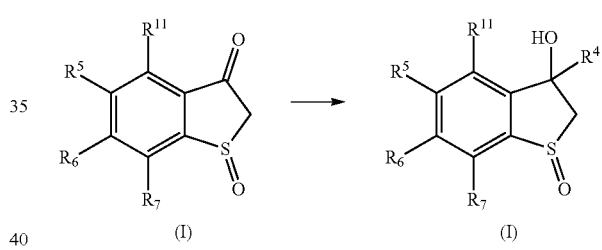

A compound of Formula (I) where $R^3$ and $R^4$ together with the carbon to which they are attached form oxo to a corresponding compound of Formula (I) where $R^3$ is hydroxy and $R^4$ is alkyl can be prepared by treating it with an alkyl Grignard reagent under conditions well known in the art.

Method (iii)

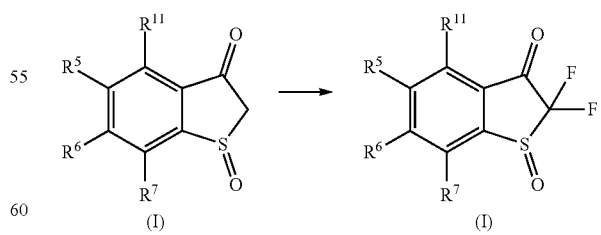

A compound of Formula (I) where $R^3$ and $R^4$ together with the carbon to which they are attached form oxo and $R^1$ and $R^2$ are each hydrogen can be converted to a corresponding compound of Formula (I) where $R^1$ and $R^2$ is fluoro by treating it with a suitable fluorinating agent such as Selectfluor under conditions well known in the art. The difluoro analog of compound (I) can be converted to a compound of Formula (I) where $R^3$ is hydroxy and $R^4$ is hydrogen or where $R^3$ is hydroxy and $R^4$ is alkyl as described in Methods (i) or (ii) above.

Method (iv)

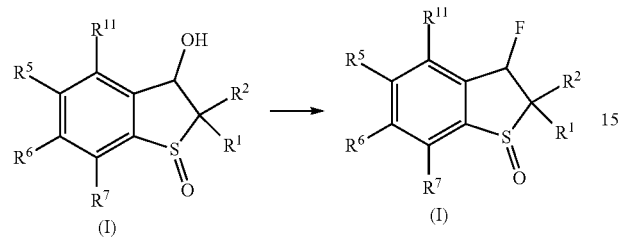

A compound of Formula (I) where $R^3$ is hydroxy and $R^4$ is hydrogen can be converted to a corresponding compound of formula (I) where $R^3$ is fluoro and $R^4$ is hydrogen by treating it with fluorinating agent such as DAST under conditions well known in the art.

Additionally, a compound of Formula (I) where $R^7$ is iodo can be converted to a corresponding compound of formula (I) where $R^7$ is alkyl, cycloalkyl, haloalkyl, or alkylsulfone by transition metal catalyzed reactions known in the art.

Compounds of Formula (I) can also be prepared by methods known in the art for example PCT Application publication No. WO2015/095048.

Compounds of Formula (I) where $R^1$ $R^2$, $R^3$, and $R^4$ are independently hydrogen, alkyl, or fluoro, $X^1$ is N or $CR^{11}$ where $R^{11}$ is as defined in the Summary, $R^6$ is other than hydrogen; and $R^5$ and $R^7$ are as defined in the Summary can be prepared as described in Scheme 2 below.

Scheme 2

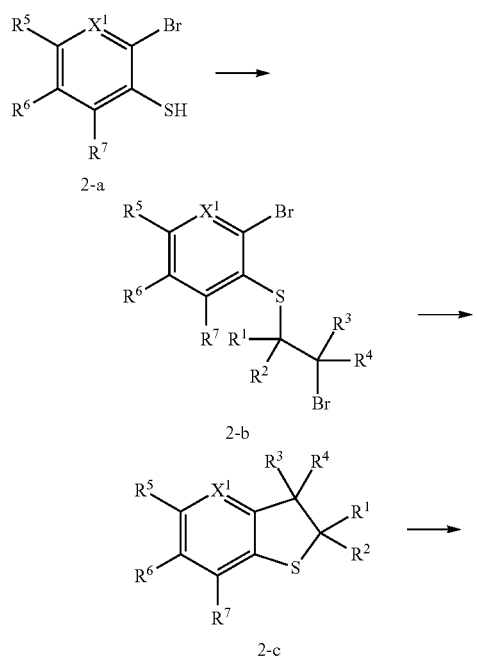

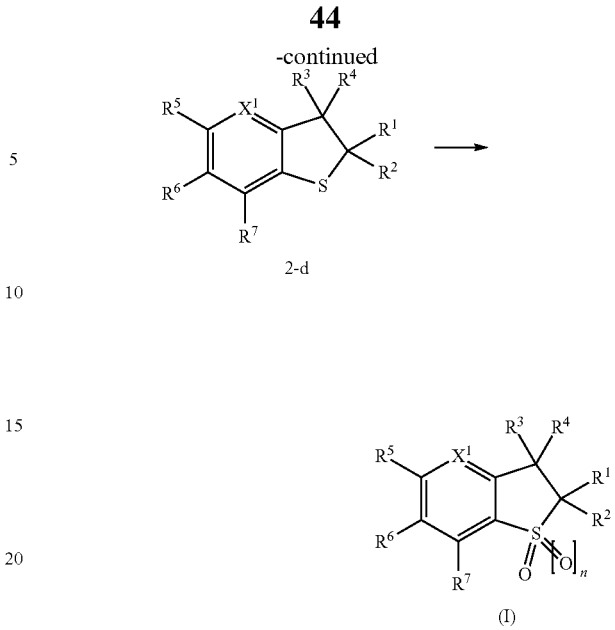

Alkylation of a bromothiol compound of formula 2-a where $R^7$ is hydrogen with 1,2-dibromoethane of formula $BrCR^1R^2CR^3R^4Br$ where $R^1$, $R^2$, $R^3$, and $R^4$ are independently H, alkyl, or fluoro, followed by intramolecular coupling mediated by copper provides a compound of formula 2-c. Compounds of formula 2-a are commercially available or they can be prepared by methods well known in the art. For example, 2-bromo-5-fluorobenzene-1-thiol is commercially available. 2-Bromo-5-chloropyridine-3-thiol can be prepared from 2-bromo-5-chloro-3-fluoropyridine by displacement of the fluoride with 2-ethylhexyl 3-sulfanylpropanoate followed by hydrolysis of resulting thioether.

Compounds of formula 2-d where $R^7$ is chloro, bromo, difluoromethane or cyano group can be prepared, if desired, from compound of formula 2-c by methods well known in the art. For example, lithiation of formula 2-c followed by treatment of the lithio intermediate with hexachloroethane or carbon tetrabromide provides compounds of formula 2-d where $R^7$ is chloro or bromo respectively. Treatment of the lithio intermediate with formaldehyde followed by fluorination of the resulting aldehyde provides compounds of formula 2-d where $R^7$ is difluoromethane. The aldehyde can also be converted to cyano group by converging the aldehyde group to an imine, followed by dehydration in acetic anhydride.

Compounds of formula 2-c or 2-d where $R^6$ is halo can be converted to corresponding compound of formula 2-c or 2-d where $R^6$ is $-LR^{10}$ as described in Scheme 1 above. Compounds of formula 2-c and 2-d are converted to a compound of Formula (I) where n is 0 or 1 by oxidizing sulfur atom in compound 2-c and 2-d with a suitable oxidizing agent such as $H_2O_2$, $KMnO_4$, $NaIO_4$, Oxone or m-CPBA under conditions known in the art.

Compounds of Formula (I) where $R^1$ and $R^2$ are independently hydrogen or halo, $X^1$ is $C-LR^{12}$ where L and $R^{12}$ are as defined in the Summary, $R^3$ is hydrogen, halo, or hydroxy, $R^4$ is hydrogen, alkyl, or halo or $R^3$ and $R^4$ together with the carbon to which they are attached form oxo; $R^6$ is other than $-L-R^{10}$; and $R^5$ and $R^7$ are as defined in the Summary can be prepared as illustrated and described in Scheme 3 below.

Scheme 3

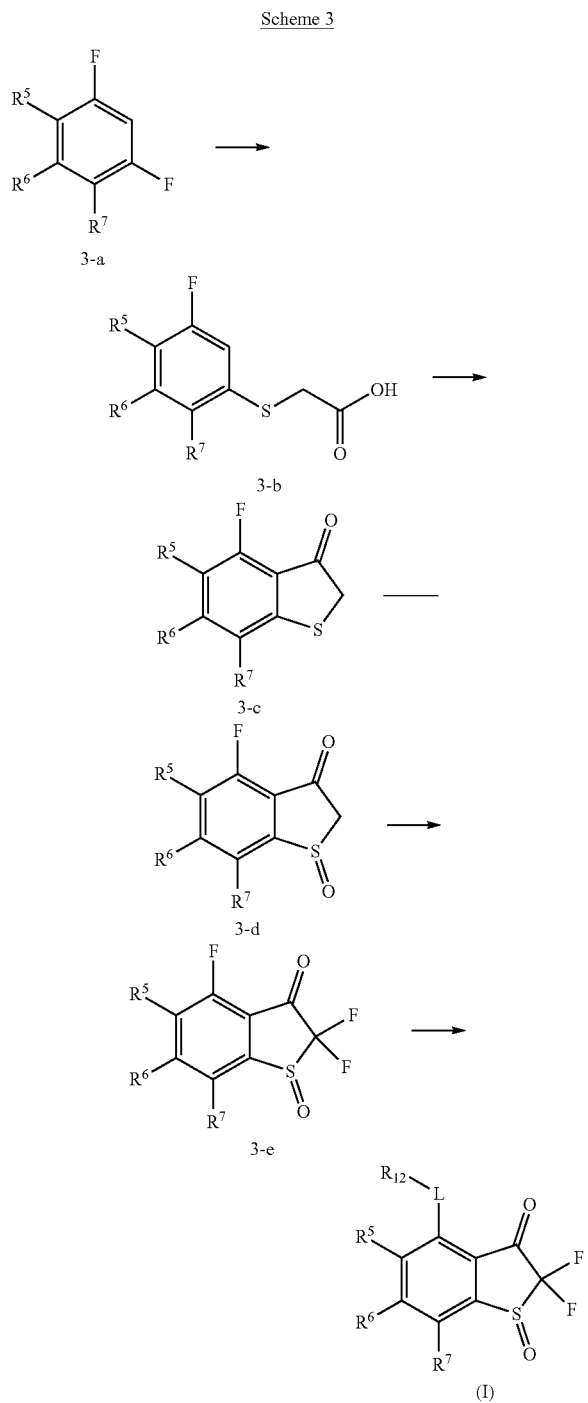

Selective substitution of difluoro 3-a with methyl 2-mercaptoacetate in the presence of base, followed by hydrolysis of the ester group under basic condition provides a carboxylic acid compound of formula 3-b. Compounds of formula 3-a are commercially available or they can be prepared by methods well known in the art. For example, 2,4-difluoro-1-iodobenzene is commercially available.

Conversion of the carboxylic acid to acyl chloride, followed by cyclization mediated by trichloroalumane provides a ketone of formula 3-c. Oxidation of sulfide and then fluorination gives 3-e.

Compounds of formula (I) where $X^1$ is C-LR$^{12}$ can be prepared treating compound 3-d or 3-e with a compound of formula R$^{12}$-LH where L is N, O, or S and R$^{12}$ is a defined in the Summary by method well known in the art. Compounds of formula R$^{12}$-LH are commercially available or they can be prepared by methods well known in the art. For example, 3-fluoro-5-hydroxybenzonitrile, 3,5-difluorophenol, 3-chloro-5-fluorophenol, 3-chloro-5-hydroxy-benzonitrile, 5-fluoropyridin-3-ol, 5-chloropyridin-3-ol, 5-hydroxynicotinonitrile, 3-fluoro-5-mercaptobenzonitrile, 3-amino-5-fluorobenzonitrile, 3,3-difluorocyclobutan-1-ol are commercially available. Compounds of Formula (I) can then be converted to other compounds of formula (I) by methods described in Schemes 1 and 2 above or by methods well known in the art. For example, a compound of Formula (I) where R$^7$ is iodo can be converted to a corresponding compound of Formula (I) where R$^7$ is methylsulfonyl or trifluoromethyl by reacting it with sodium methanesulfinate or methyl 2,2-difluoro-2-sulfoacetate, respectively in the presence of copper iodide under conditions well known in the art. The oxo group at the 3-position can then be converted to other groups as described in Scheme 1 above.

Utility

The compounds disclosed herein are useful for the treatment of HIF-2α mediated diseases which include but are not limited to, various types of cancer, liver disease such as nonalcoholic steatohepatitis (NASH), inflammatory disease such as inflammatory bowel disease (IBD), pulmonary diseases such as pulmonary arterial hypertension (PAH), and iron load disorders.

HIF-2α plays an important role in the initiation and progression of many human cancers. Many extensive studies have demonstrated the role of increased HIF-2α activity in driving clear cell renal cell carcinoma (ccRCC) (see review by Shen and Kaelin, Seminars in Cancer Biology 23: 18-25, 2013). Abnormal HIF-2α activity is largely due to loss of function of a tumor suppressor, VHL. It is known that over eighty percent of ccRCC have defective VHL either through deletion, mutation or disturbed post-translational modification. Defective VHL leads to constitutively active HIF-2α proteins regardless of oxygen level. Various studies employing gain-of-function and loss-of-function approaches in mouse models have demonstrated that HIF-2α is an oncogenic substrate of VHL (see Kondo, et al. Cancer Cell 1: 237-246, 2002; Kondo, et al. PLoS Biology 1: 439-444, 2002; Maranchi, et al. Cancer Cell 1: 247-255, 2002; Zimmer, et al. Mol. Cancer Res 2: 89-95, 2004). For example, knockdown of HIF-2α in VHL-null tumors inhibited tumor formation; while reintroduction of VHL and overexpression of HIF-2α overcame the tumor suppressive role of VHL. Moreover, single nucleotide polymorphism in HIF-2α, is associated with resistant to PHD-mediated degradation, has been linked to an increased risk of developing RCC. In addition to serving as an archetypical tumor-initiating event in ccRCC, the VHL-HIF-2α axis has also been implicated in ccRCC tumor metastasis through its downstream CXCR4 and CYTIP (see Vanharanta et al. Nature Medicine 19: 50-59, 2013; Peter Staller et al. Nature. 2003 Sep. 18; 425(6955):307-11). Taken together, these studies support the potential therapeutic utility of HIF-2α targeted agents for the treatment of ccRCC.

Defective VHL not only predisposes patients to kidney cancer (with a 70% lifetime risk), but also to hemangioblastomas, pheochromocytoma, endolymphatic sac tumors and pancreatic neuroendocrine tumors. Tumors derived from defective VHL are frequently driven by the constitutively active downstream HIF-α proteins, with the majority of these dependent on HIF-2α activity (see Maher, et al. Eur. J. Hum. Genet. 19: 617-623, 2011). Both genetic and epigenetic mechanisms can lead to the loss of function in VHL. Epigenetic inactivation of VHL expression and thus constitutive activation of HIF-2α proteins has been found in many cancers including RCC, multiple myeloma, retinoblastoma, NSCLC, pancreatic endocrine tumors, squamous cell carcinoma, acute myeloid leukemia, myelodysplastic syndrome, and esophageal squamous cell carcinoma (see reviewed in Nguyen, et al. Arch. Phann. Res 36: 252-263, 2013). HIF-2α has also been linked to cancers of the retina, adrenal gland and pancreas through both loss of function in VHL and activating mutations in HIF-2α. Recently, gain-of-function HIF-2α mutations have been identified in erythrocytosis and paraganglioma with polycythemia (see Zhuang, et al. NEJM 367: 922-930, 2012; Percy, et al. NEJM 358: 162-168, 2008; and Percy, et al. Am. J. Hematol. 87: 439-442, 2012). Notably, many of the known HIF-2α target gene products (e.g., VEGF, PDGF, and cyclin Dl) have been demonstrated to play pivotal roles in cancers derived from kidney, liver, colon, lung, and brain. Thus, a HIF-2α targeted therapy could be beneficial for the above cancers In addition to loss of function in VHL and activating mutation of HIF-2α, HIF-2α proteins are also frequently upregulated in the intratumor environment of rapidly growing tumors, due to the hypoxic condition resulting from poor vascularization in large tumors. The activated HIF-2α pathways, in turn, further promotes tumor cell survival and proliferation by transcriptionally upregulating various essential factors.

A large body of studies have demonstrated a correlation between HIF-2α overexpression and poor prognosis in various cancers including cancers of astrocytoma, breast, cervical, colorectal, glioblastoma, glioma, head and neck, liver, non-small cell lung, melanoma, neuroblastoma, ovarian, and prostate, thereby supporting the pursuit of HIF-2α as a therapeutic target in treating these cancers (see reviewed in Keith, et al. Nature Rev. Cancer 12: 9-22, 2012). HIF-2α has been demonstrated to augment the growth of APC mutant colorectal cancer through its regulation of genes involved in proliferation, iron utilization and inflammation (see Xue, et al. Cancer Res 72: 2285-2293, 2012; and Xue and Shah, Carcinogenesis 32: 163-169, 2013). In hepatocellular carcinoma (HCC), knock-down of HIF-2α in preclinical models led to the inhibition of cell proliferation in vitro and tumor growth in vivo through the downregulation of VEGF and cyclin D 1 (see He, et al. Cancer Sci. 103: 528-534, 2012). In NSCLC, around 50% of patients exhibited overexpression of HIF-2α protein, which strongly correlates with higher VEGF expression and reduced overall survival. On the other hand, HIF-1α does not correlate with reduced overall survival in lung cancer patients even though its expression is also often increased (see Giatromanolaki, et al. Br. J. Cancer 85: 881-890, 2001). Extensive studies in mice engineered with both non-degradable HIF-2α and mutant KRAS tumors have demonstrated an increased tumor burden and a decreased survival when compared to mice with only mutant KRAS expression (see Kim, et al. J. Clin. Invest. 119: 2160-2170, 2009). These studies demonstrate that HIF-2α promotes tumor growth and progression in lung cancer, and also negatively correlates with clinical prognosis.

HIF-2α activity has also been linked to the progression of chronic obstructive pulmonary disease (COPD), in addition to lung cancer, in mouse models (see Karoor, et al. Cancer Prev. Res. 5: 1061-1071, 2012). HIF-2α activity has also been demonstrated to be important in cancers of the central nervous system (see Holmquist-Mengelbier, et al. Cancer Cell 10: 413-423, 2006 and Li, et al. *Cancer Cell* 15: 501-513, 2009). HIF-2α knockdown reduced tumor growth in preclinical animal models of neuroblastoma. Conversely, increased level of HIF-2α correlated with advanced disease, poor prognosis and higher VEGF levels, which likely contribute to the poor clinical outcome. Similarly, higher HIF-2α expression has been correlated with a poor survival in glioma Experimentally, inhibition of HIF-2α in glioma stem cells reduced cell proliferation and survival in vitro and tumor initiation in vivo. Interestingly, while HIF-1α is expressed in both neural progenitors and brain tumor stem cells, HIF-2α is found exclusively in the latter. Moreover, survival of glioma patients correlates to with HIF-2α, but not HIF-1α level.

Radiation therapy is frequently used for approximately 50% of cancer patients, either alone or in combination with other therapies. However, the hypoxia microenvironment within the tumor has long been associated with resistance to radiation therapy. Bhatt and co-workers found that decreased level of HIF-2α leads to increased sensitivity to ionizing radiation in renal cell carcinoma cell lines (see Bhatt, et al. BJU Int. 102: 358-363, 2008). Furthermore, mechanistic studies from Bertout et. al, have demonstrated that HIF-2α inhibition enhances the effectiveness of radiation through increased p53-dependent apoptosis (see Bertout, et al. *PNAS* 106: 14391-14396, 2009). Thus, HIF-2α targeted therapy, such as specific HIF-2α inhibitors, could improve the response to radiation therapy in various cancers.

In addition to a direct role in promoting the initiation, progression and metastasis of tumor cells (e.g. ccRCC), HIF-2α also indirectly contributes to tumorigenesis through augmenting the immunosuppressive effect of hypoxia within the tumor microenvironment. Expression of HIF-2α has been detected in cells of the myeloid lineage (see Talks K L, et dal. Am J Pathol. 2000; 157(2):411-421). For example, HIF-2α is shown to favor the polarization of macrophages to the immunosuppressive M2 phenotype and enhances migration and invasion of tumor-associated macrophages (see Imtiyaz H Z et al. J Clin Invest. 2010; 120(8):2699-2714). Thus, increased level of HIF-2α in tumor-associated macrophages (TAMs) is associated with high-grade human tumors and more importantly, correlates with poor prognosis. Furthermore, HIF-2α can indirectly promote additional immunosuppressive pathways (e.g. adenosine and arginase etc.) by modulating the expression of key signaling regulators such as adenosine A2B/A2A receptors and arginase. These data support that HIF-2α is a potential therapeutic target for treating a broader range of inflammatory disorders and cancer either as a single agent or in combination with other therapeutic agents, e.g., immunotherapies.

Due to the key roles of HIF-α proteins in regulating physiological response to the fluctuation of oxygen levels, they have been causally associated with many hypoxia-related pathological processes in addition to cancer. One such disease is PAH, a debilitating and life-threatening disease with very poor prognosis. Recent studies demonstrated that HIF-2α contributed to the process of hypoxic pulmonary vascular remodeling, reduced plasticity of the vascular bed, and ultimately, debilitating PAH (see Andrew S., et al. Proc Natl Acad Sci USA. 2016 Aug. 2; 113(31): 8801-8806, Tang H, et al. Am J Physiol Lung Cell Mol Physiol. 2018 Feb. 1; 314(2):L256-L275.). These studies offer new understanding in the role of pulmonary endothelial; HIF-2α in regulating the pulmonary vascular response to hypoxia, provide a new therapeutic strategy by targeting HIF-2α. Another example of hypoxia-related pathological processes is IBD, a chronic relapsing inflammatory disease of the intestine. It has been found that intestinal inflammation and subsequently IBD arose when a dysregulated epithelial oxygen tension occurs and intensifies across epithelial villi in the intestine (see Shah Y. M., Molecular and Cellular Pediatrics, 2016 December; 3(1):1). Interestingly, HIF-2α activation contributes to IBD, while HIF-1α in intestinal epithelial cells is considered as a major protective factor in IBD (see Karhausen J, et al. J Clin Invest. 2004; 114(8):1098-1106; Furuta G T, et al. J Exp Med. 2001; 193(9):1027-1034). Mechanistically, HIF-2α activation not only leads to the upregulation of pro-inflammatory cytokines which promotes IBD directly, but also results in loss of intestine barrier integrity, thus indirectly contributing to the manifestation of IBD. (see Xue X, et al. Gastroenterology. 2013; 145(4):831-841; Glover L E, et al. Proc Natl Acad Sci U S A. 2013; 110(49):19820-19825). Therefore, a HIF-2α inhibitor holds the promise of reverting the pro-inflammatory condition and increasing the intestinal barrier integrity, thus alleviating the symptoms of IBD.

HIF-2α inhibitor also represents a novel therapeutic approach in NASH, for which limited therapeutic options are available. An elegant study recently showed that an intestine-specific disruption of HIF-2α led to a significant reduction of hepatic steatosis and obesity induced by high-fat-diet. Mechanistically, intestine HIF-2α positively regulates the gene encoding neuraminidase 3, thus regulates ceramide metabolism which contributes to the development of NASH (see Xie C, et al. Nat Med. 2017 November; 23(11):1298-1308.). Therefore, a HIF-2α-specific inhibitor will have preventive and therapeutic effects on metabolic disorders, such as NASH.

Several connections between the level of HIF-2α and iron homeostasis have been identified (see Peyssonnaux C et al, Cell Cycle. 2008; 7(1):28-32). In particular, multiple studies have demonstrated the important role of HIF-2α in iron load disorders. Interestingly, HIF-2α, not HIF-1α, has emerged as an important "local" regulator of intestinal iron status through its regulation of various genes essential in iron transport and absorption (see Mastrogiannaki M, et al. J Clin Invest. 2009; 119(5):1159-1166). Therefore, a small molecule inhibitor of HIF-2α may be useful in improving iron homeostasis in patients with iron disorders.

Accordingly, the present invention provides a method for treating the severity of a disease condition, or disorder where activation or over activation of HIF-2α is implicated in the disease state. In another aspect, the present disclosure provides a method of treating renal cell carcinoma of a subject with a compound disclosed herein or a pharmaceutically acceptable salt thereof.

HIF-2α inhibitors also have therapeutic potentials for a broad range of non-cancer indications, including, but not limited to, NASH, IBD, PAH, and iron overload.

Testing

The HIF-2α inhibitory activity of the compounds of the present disclosure can be tested using the in vitro assay described in Biological Example 1 below.

Pharmaceutical Compositions

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the patient, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance.

The compositions are comprised of in general, a compound of this disclosure in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator. Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

Combinations and Combination Therapies

The compounds of this disclosure may be used in combination with one or more other drugs in the treatment of diseases or conditions for which compounds of this disclosure or the other drugs may have utility. Such other drug(s) may be administered, by a route and in an amount commonly used therefore, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other drugs, in addition to a compound of the present disclosure.

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of the present disclosure. When a compound of this disclosure is used contemporaneously with one or more other drugs, a pharmaceutical composition containing such other drugs in addition to the compound of this disclosure can be used. Accordingly, the pharmaceutical compositions of the present disclosure also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™) geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel," which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Suitable anti-cancer agents also include inhibitors of kinases associated cell proliferative disorder. These kinases include but not limited to Aurora-A, BTK, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, MEK, PAK1, PAK2, PAK3, PAK4, PDK1, PKA, PKC, RAF, Rsk and SGK. For example, inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, carbozantinib, or crizotinib; VEGFR inhibitor such as sunitinib, sorafenib, regorafinib, lenvatinib, vandetanib, carbozantinib, axitinib; EGFR inhibitor such as afatinib, brivanib, carbozatinib, erlotinib, gefitinib, neratinib, lapatinib; PI3K inhibitor such as XL147, XL765, BKM120 (buparlisib), GDC-0941, BYL719, IPI145, BAY80-6946. BEX235 (dactolisib), CAL101 (idelalisib), GSK2636771, TG100-115; MTOR inhibitor such as rapamycin (sirolimus), temsirolimus, everolimus, XL388, XL765, AZD2013, PF04691502, PKI-587, BEZ235, GDC0349; MEK inhibitor such as AZD6244, trametinib, PD184352, pimasertinib, GDC-0973, AZD8330; CSF1R inhibitors (PLX3397, LY3022855, etc.) and CSF1R antibodies (IMC-054, RG7155, etc.); TGF beta receptor kinase inhibitor such as LY2157299; BTK inhibitor such as ibrutinib;

Other anti-cancer agents include proteasome inhibitor such as carfilzomib, MLN9708, delanzomib, or bortezomib; BET inhibitors such as INCB054329, OTX015, CPI-0610;LSD1 inhibitors such as GSK2979552, INCB059872; HDAC inhibitors such as panobinostat, vorinostat; DNA methyl transferase inhibitors such as azacytidine, decitabine), and other epigenetic modulator; SHP-2 inhibitor such as TNO155; Bcl2 inhibitor ABT-199, and other Bcl-2 family protein inhibitors; HIF-2α inhibitors such as PT2977 and PT2385; Beta catenin pathway inhibitors, notch pathway inhibitors and hedgehog pathway inhibitors; Antibodies or other therapeutic proteins against VEGF include bevacizumab and aflibercept Other anti-cancer agents/drugs that can be used in combination with the compounds of the invention include, but are not limited to, liver X receptor (LXR) modulators, including LXR agonists and LXR beta-selective agonists; and aryl hydrocarbon receptor (AhR) inhibitors.

Other anti-cancer agents that can be employed in combination with a compound of this disclosure include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or Ril2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of the disclosure include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of this disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., cytarabine), purine analogs (e.g., mercaptopurine, thioguanine, pentostatin).

Examples of natural products useful in combination with a compound of this disclosure include but are not limited to *vinca* alkaloids (e.g., vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of this disclosure) include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, cytarabine), purine analogs (e.g., mercaptopurine, thioguanine, pentostatin.

Examples of hormones and antagonists useful in combination a compound of this disclosure include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Other anti-cancer agents that can be employed in combination with a compound of the disclosure include: anticancer agents which act by arresting cells in the G2-M phases due to stabilized microtubules and include Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

One or more additional immune checkpoint inhibitors can be used in combination with a compound as described herein for treatment of HIF-2α-associated diseases, disorders or conditions. Exemplary immune checkpoint inhibitors include inhibitors (smack molecules or biologics) against immune checkpoint molecules such as CD27, CD28, CD40, CD122, CD96, CD73, CD39, CD47, OX40, GITR, CSF1R, JAK, PI3K delta, PI3K gamma, TAM, arginase, CD137 (also known as 4-1BB), ICOS, A2AR, A2BR, SHP-2, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR, CD137 and STING. In some embodiments, the immune checkpoint molecule is an inhibitory checkpoint molecule selected from B7-H3, B7-H4, BTLA, CTLA-4, IDO, TDO, Arginase, KIR, LAG3, PD-1, TIM3, CD96, TIGIT and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, or pembrolizumab or PDR001. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C.

In some embodiments, the anti-PD-L1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab. In some embodiments, the inhibitor of an immune checkpoint molecule is an inhibitor of LAG3, e.g., an anti-LAG3 antibody. In some embodiments, the anti-LAG3 antibody is BMS-986016 or LAG525. In some embodiments, the inhibitor of an immune checkpoint molecule is an inhibitor of GITR, e.g., an anti-GITR antibody. In some embodiments, the anti-GITR antibody is TRX518 or, MK-4166, INCAGN01876 or MK-1248. In some embodiments, the inhibitor of an immune checkpoint molecule is an inhibitor of OX40, e.g., an anti-OX40 antibody or OX40L fusion protein. In some embodiments, the anti-OX40 antibody is MEDI0562 or, INCAGN01949, GSK2831781, GSK-3174998, MOXR-0916, PF-04518600 or LAG525. In some embodiments, the OX40L fusion protein is MEDI6383.

Compounds of the invention can also be used to increase or enhance an immune response including increasing the immune response to an antigen; to improve immunization, including increasing vaccine efficacy; and to increase inflammation. In some embodiments, the compounds of the invention can be sued to enhance the immune response to vaccines including, but not limited, *Listeria* vaccines, oncolytic viral vaccines, and cancer vaccines such as GVAX® (granulocyte-macrophage colony-stimulating factor (GM-CF) gene-transfected tumor cell vaccine). Anti-cancer vaccines include dendritic cells, synthetic peptides, DNA vaccines and recombinant viruses. Other immune-modulatory agents also include those that block immune cell migration such as antagonists to chemokine receptors, including CCR2 and CCR4; Sting agonists and Toll receptor agonists.

Other anti-cancer agents also include those that augment the immune system such as adjuvants or adoptive T cell transfer. Compounds of this application may be effective in combination with CAR (Chimeric antigen receptor) T cell treatment as a booster for T cell activation

EXAMPLES

The following preparations of compounds of Formula (I) are given to enable those skilled in the art to more clearly understand and to practice the present disclosure. They should not be considered as limiting the scope of the disclosure, but merely as being illustrative and representative thereof.

Example 1

Synthesis of 3-((7-(difluoromethyl)-2,2-difluoro-1-oxido-3-oxo-2,3-dihydrobenzo[b]thiophen-6-yl oxy)-5-fluorobenzonitrile

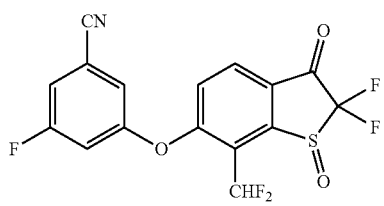

Step 1: 2,4-difluoro-3-formylbenzonitrile

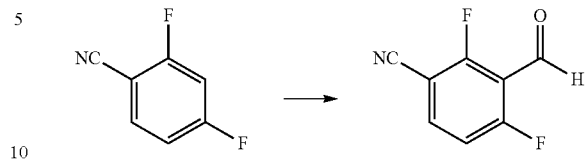

To a stirred solution of 2,4-difluorobenzonitrile (6 g, 43.13 mmol, 1.0 equiv) in THF (200 mL) was added LDA (94 mL, 87.36 mmol, 2.0 equiv) dropwise at −78° C. under nitrogen atmosphere. The reaction mixture was stirred at −78° C.-60° C. for 35 mins. To the above mixture was added DMF (8.3 mL, 114.17 mmol, 6.0 equiv) dropwise over 5 minutes at −78° C. The resulting mixture was stirred for additional 5 min at −78° C. and then was poured into 200 mL of HCl aq. Solution (0.5 M). The mixture was extracted with EtOAc. The combined organic layer was washed with brine, dried over anhydrous $Na_2SO_4$. After filtration, the filtrate was concentrated in vacuum. The residue was purified by flash chromatography, eluted with PE/EtOAc (0-25%) to afford 3.7 g (51.33%) of the title product as a white solid.

Step 2: 3-(difluoromethyl)-2,4-difluorobenzonitrile

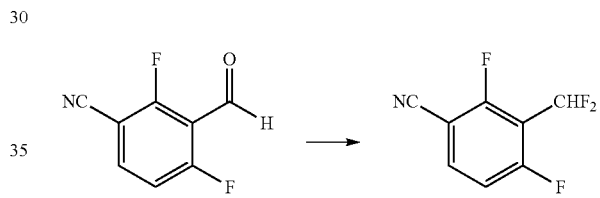

To a stirred solution of 2,4-difluoro-3-formylbenzonitrile (3.7 g, 22.14 mmol, 1 equiv) in DCM (40 mL) was added DAST (7.1 g, 44.28 mmol, 2.0 equiv) in portions at room temperature under nitrogen atmosphere. After stirring for 3 h, the reaction mixture was concentrated in vacuum. The residue was purified by flash chromatography, eluted with PE/EtOAc (10:1) to afford 3.4 g, (81.20%) of title product as a white solid.

Step 3: 4-(3-cyano-5-fluorophenoxy)-3-(difluoromethyl)-2-fluorobenzonitrile

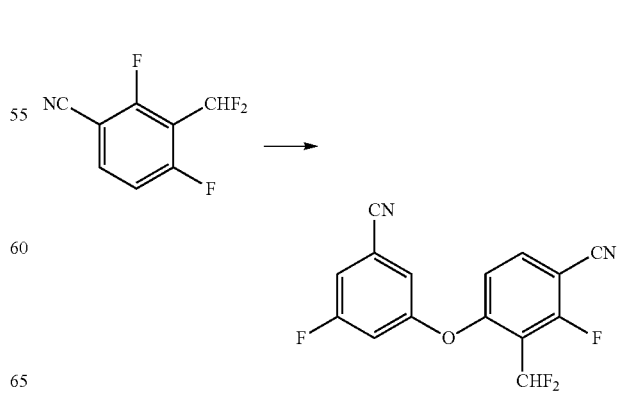

To a stirred mixture of 3-(difluoromethyl)-2,4-difluorobenzonitrile (4 g, 21.15 mmol, 1.0 equiv) and K₃PO₄ (4.5 g, 21.20 mmol, 1.0 equiv) in acetonitrile (100 mL) was added 3-fluoro-5-hydroxybenzonitrile (2.2 g, 15.86 mmol, 0.75 equiv) in portions at room temperature under nitrogen atmosphere. The reaction mixture was stirred for 2 h and then quenched with water at room temperature. The resulting mixture was extracted with EtOAc. The combined organic layer was washed with brine, dried over anhydrous Na₂SO₄. After filtration, the filtrate was concentrated in vacuum. The residue was purified by flash chromatography, with PE/EtOAc (5:1) as eluent to afford 3.9 g of crude product. The crude product was purified by reverse flash chromatography under following conditions: column, C18 silica gel; ACN in water, 30% to 75% gradient to give 1.6 g (24.70%) of the title compound as a white solid.

Step 4: 4-(3-cyano-5-fluorophenoxy)-3-(difluoromethyl)-2-(methylthio)benzonitrile

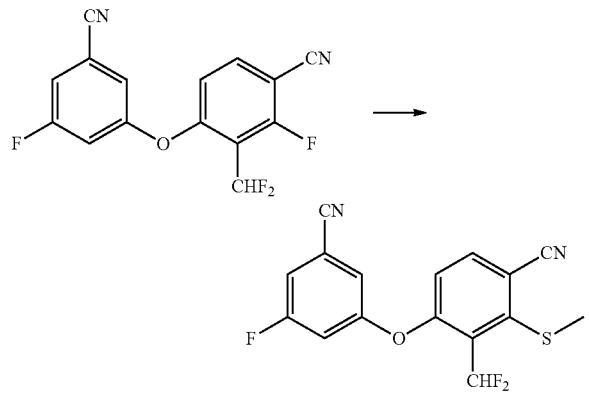

To a stirred solution of 4-(3-cyano-5-fluorophenoxy)-3-(difluoromethyl)-2-fluorobenzonitrile (600 mg, 1.96 mmol, 1.0 equiv) in ACN (40 mL) was added sodium thiomethoxide (206.0 mg, 2.94 mmol, 1.5 equiv) at 0° C. The resulting mixture was stirred for 4 h at this temperature and then quenched with water at 0° C. The resulting mixture was extracted with EtOAc. The combined organic layer was washed with brine, dried over anhydrous Na₂SO₄. After filtration, the filtrate was concentrated in vacuum. The residue was purified by flash chromatography, using with PE/EtOAc (5:1) as eluent to afford 430 mg (67.87%) of the title compound as a light yellow solid.

Step 5: 4-(3-cyano-5-fluorophenoxy)-3-(difluoromethyl)-2-(methylsulfinyl)benzonitrile

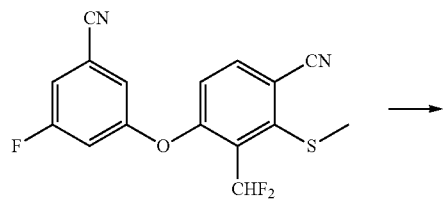

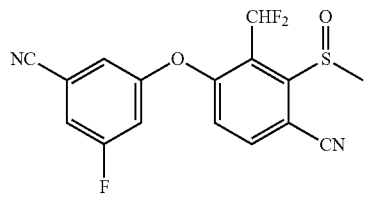

To a stirred solution of 4-(3-cyano-5-fluorophenoxy)-3-(difluoromethyl)-2-(methylsulfanyl)-benzonitrile (100 mg, 0.3 mmol, 1.0 equiv) in ACN (4 mL) were added a solution of Oxone (276 mg, 0.45 mmol, 1.5 equiv) in water (0.4 mL) at room temperature. The reaction mixture was stirred for 3 h at 45° C. and then quenched with water at room temperature. The resulting mixture was extracted with CH₂Cl₂. The combined organic layer was washed with brine, dried over anhydrous Na₂SO₄. After filtration, the filtrate was concentrated in vacuum. The residue was purified by Prep-TLC (PE/EtOAc=2/1) to afford 50 mg (47.7%) of the title product as a white solid. MS (ES, m z): [M+1]=351.

Step 6: 3-((7-(difluoromethyl)-1-oxido-3-oxo-2,3-dihydrobenzo[b]thiophen-6-yl)oxy)-5-fluorobenzonitrile

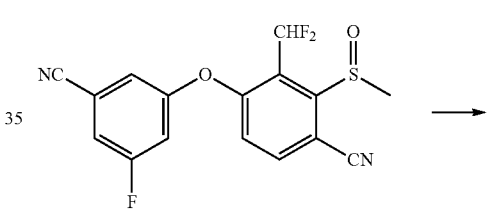

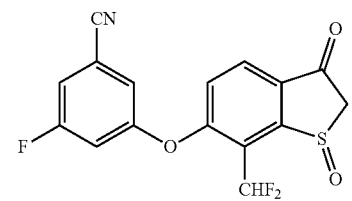

To a stirred solution of 4-(3-cyano-5-fluorophenoxy)-3-(difluoromethyl)-2-methanesulfinyl-benzonitrile (500 mg, 1.43 mmol, 1.0 equiv) in THF (20 mL) was added LDA (0.85 mL, 1.71 mmol, 1.2 equiv) dropwise at −78° C. under nitrogen atmosphere. The reaction solution was stirred for 3 h −78° C. and then quenched with water at −78° C. The resulting mixture was diluted with EtOAc and the phases were separated. The organic layer was washed with water and brine, dried over anhydrous Na₂SO₄ and concentrated. The residue was purified by flash chromatography, using PE/EtOAc (5:1) as eluent to afford the title compound (200 mg, 39.8%) as a white solid. MS (ES, m z): [M+1+41]⁺= 393.1.

Step 7: 3-((7-(difluoromethyl)-2,2-difluoro-1-oxido-3-oxo-2,3-dihydrobenzo[b]thiophen-6-yl)oxy)-5-fluorobenzonitrile

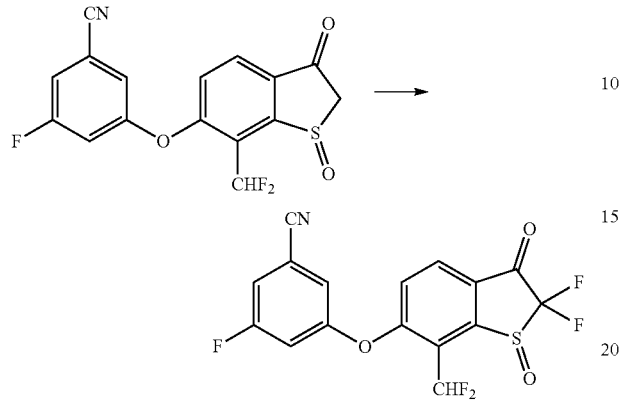

To a stirred solution of 3-((7-(difluoromethyl)-1-oxido-3-oxo-2,3-dihydrobenzo[b]thiophen-6-yl)oxy)-5-fluorobenzonitrile (240 mg, 0.68 mmol, 1.0 equiv) in acetonitrile (10 mL) were added Na₂CO₃ (159.3 mg, 1.50 mmol, 2.2 equiv) and selectfluor (532.4 mg, 1.50 mmol, 2.2 equiv) at room temperature. After stirring for 2 h, the reaction was quenched with water at room temperature. The resulting mixture was extracted with EtOAc. The combined organic layers were washed with brine, dried over anhydrous Na₂SO₄ and concentrated. The residue was purified by silica gel column chromatography, with PE/EtOAc (10:1) as eluent to afford the title compound (150 mg, 56.6%) as a white solid. GCMS (EI): [M]=387.

Example 2

Synthesis of 3-((7-(difluoromethyl)-2,2-difluoro-3-hydroxy-1-oxido-2,3-dihydrobenzo[b]-thiophen-6-yl)oxy)-5-fluorobenzonitrile

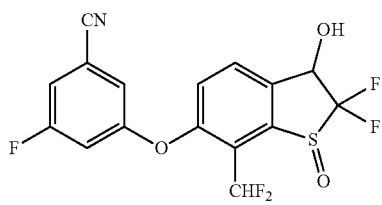

To a stirred solution of 3-((7-(difluoromethyl)-2,2-difluoro-1-oxido-3-oxo-2,3-dihydrobenzo[b]thiophen-6-yl)oxy)-5-fluorobenzonitrile (40 mg, 1 equiv) in MeOH (2 mL) was added NaBH₄ (8 mg, 0.21 mmol, 2.05 equiv) at 0° C. The reaction solution was stirred for 1 h at 0° C. and then quenched with water at 0° C. The resulting mixture was extracted with EtOAc. The organic layer was washed with water and brine, dried over anhydrous Na₂SO₄. After filtration, the filtrate was concentrated under reduced pressure to afford the title compound (30 mg, 74.6%) as a white solid.

Example 3

Synthesis of a mixture of 3-(((1S,3R)-7-(difluoromethyl)-2,2,3-trifluoro-1-oxido-2,3-dihydrobenzo[b]-thiophen-6-yl)oxy)-5-fluorobenzonitrile and 3-(((1R,3S)-7-(difluoromethyl)-2,2,3-trifluoro-1-oxido-2,3-dihydrobenzo[b]thiophen-6-yl)oxy)-5-fluorobenzonitrile (3a) and a mixture of 3-(((1S,3S)-7-(difluoromethyl)-2,2,3-trifluoro-1-oxido-2,3-dihydrobenzo[b]thiophen-6-yl)oxy)-5-fluorobenzonitrile and 3-(((1R,3R)-7-(difluoromethyl)-2,2,3-trifluoro-1-oxido-2,3-dihydrobenzo[b]thiophen-6-yl)oxy)-5-fluorobenzonitrile (3b)

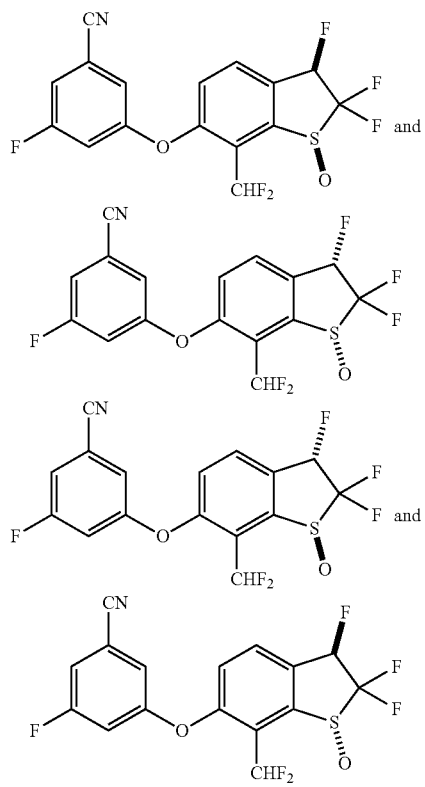

To a stirred solution of 3-[[7-(difluoromethyl)-2,2-difluoro-3-hydroxy-1-oxo-2,3-dihydro-1lambda4-benzothiophen-6-yl]oxy]-5-fluorobenzonitrile (30 mg, 0.08 mmol, 1.0 equiv) in DCM (3 mL) was added DAST (16.1 mg, 0.10 mmol, 1.3 equiv) in portions at room temperature under nitrogen atmosphere. The reaction solution was stirred for 2 h and then quenched by saturated sodium carbonate aqueous solution. The resulting mixture was extracted with CH₂Cl₂. The combined organic layer was washed with brine, dried over anhydrous Na₂SO₄ and concentrated. The residue was purified by Prep-HPLC to afford the title compounds (8.5 mg, 28%) as a white solid. The material was separated chiral HPLC to give two enantiomers. The configuration of these two enantiomers were not established.

Separation condition: CHTRALPAK IA-3 column; flow rate: 1.0 mL/min; EtOH/Hexane 20% One of 3a and 3b has $t_R$=2.0 min; MS (ES, m z): [M−1]=390 and the other of 3a and 3b has tR=2.5 min; MS (ES, m z): [M−1]=390.

Example 4

Synthesis of 3-chloro-5-((7-(difluoromethyl)-2,2-difluoro-1-oxido-3-oxo-2,3-dihydrobenzo[b]thiophen-6-yl)oxy)benzonitrile

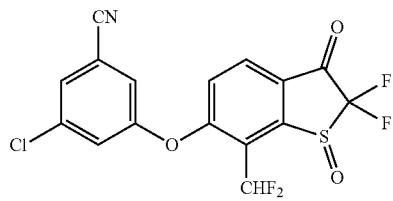

Step 1: 4-bromo-2-fluoro-3-formylbenzonitrile

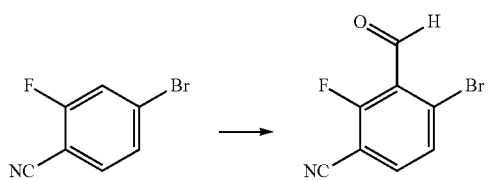 [SMILES: N#Cc1ccc(Br)cc1F ; N#Cc1ccc(Br)c(C=O)c1F]

To a stirred solution of 4-bromo-2-fluorobenzonitrile (20 g, 100 mmol, 1.0 equiv) in THF (200 mL) was added LDA (75.00 mL, 150 mmol, 1.5 equiv) dropwise at −78° C. under nitrogen atmosphere. After stirred at −78° C.~−60° C. for 30 minutes, and methyl formate (12.01 g, 200 mmol, 2.0 equiv) was added to the above mixture dropwise over 1 min at −78° C. and the resulting mixture was stirred for additional 1 min at −78° C. The reaction mixture was poured into HCl aq. solution (0.5 M, 400 mL) and extracted with EtOAc. The combined organic layers were washed with brine, dried over anhydrous $Na_2SO_4$ and concentrated. The residue was purified by silica gel column chromatography, with EtOAc/PE (0-25%) as eluent to afford the title compound 11g (48.2%) as a yellow solid.

Step 2: 4-bromo-3-(difluoromethyl)-2-fluorobenzonitrile

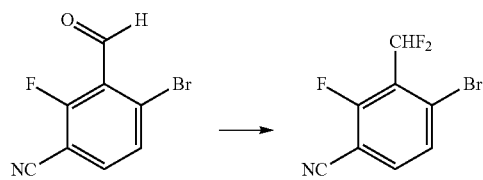 [SMILES: N#Cc1ccc(Br)c(C=O)c1F ; N#Cc1ccc(Br)c(C(F)F)c1F]

To a stirred solution of 4-bromo-2-fluoro-3-formylbenzonitrile (24 g, 105.25 mmol, 1.0 equiv) in DCM (300 mL) was added DAST (33.93 g, 210.51 mmol, 2.0 equiv) dropwise at room temperature under nitrogen atmosphere. After stirred for 3 h, the reaction was quenched with sat. $NaHCO_3$ aq. solution at 0° C. and then extracted with $CH_2Cl_2$. The combined organic layers were washed with brine, dried over anhydrous $Na_2SO_4$ and concentrated. The residue was purified by silica gel column chromatography, using PE/EtOAc (10:1) as eluent to afford the title compound 20 g (76%) as a yellow solid.

Step 3: 4-bromo-3-(difluoromethyl)-2-(methylthio)benzonitrile

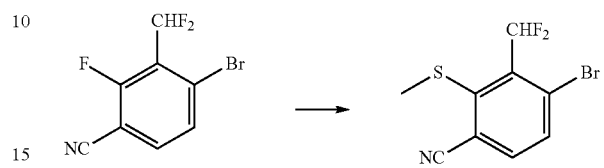

To a stirred solution of 4-bromo-3-(difluoromethyl)-2-fluorobenzonitrile (10 g, 40 mmol, 1.0 equiv) in ACN (150 mL) was added (methylsulfanyl)sodium (5.61 g, 80 mmol, 2.0 equiv) at 0° C. After stirring at rt for 4 h, the reaction mixture was quenched with water at 0° C. and then extracted with EtOAc. The combined organic layers were washed with brine, dried over anhydrous $Na_2SO_4$ and concentrated. The crude material (8.8 g) was used in next step directly without further purification.

Step 4: 4-bromo-3-(difluoromethyl)-2-(methylsulfinyl)benzonitrile

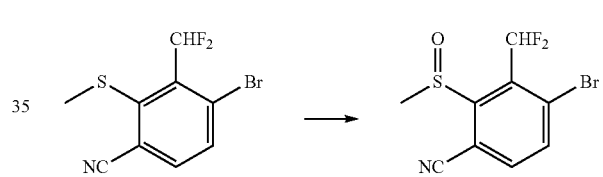

To a stirred solution of 4-bromo-3-(difluoromethyl)-2-(methylsulfanyl)benzonitrile (8.8 g, 31.64 mmol, 1.0 equiv) in ACN (150 mL) were added Oxone (10.64 g, 63.27 mmol, 2.0 equiv) and water (15 mL) at room temperature. After stirring for 3 h at 40° C., the reaction was quenched with water at 0° C. The resulting mixture was extracted with EtOAc. The combined organic layers were washed with brine, dried over anhydrous $Na_2SO_4$ and concentrated. The residue was purified by silica gel column chromatography, with EtOAc/PE (10%-40%) as eluent to afford the title compound 6 g (64.4%) as a white solid.

Step 5: 6-bromo-7-(difluoromethyl)benzo[b]thiophen-3(2H)-one 1-oxide

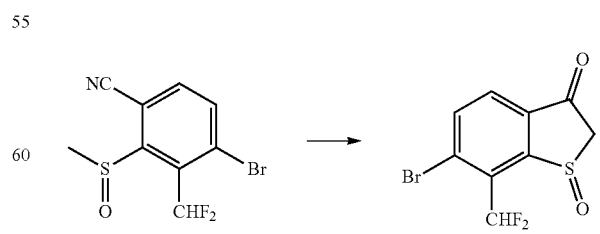

To a stirred solution of 4-bromo-3-(difluoromethyl)-2-methanesulfinylbenzonitrile (3.0 g, 10.20 mmol, 1.0 equiv) in THF (250 mL) was added LDA (8.67 mL, 17.34 mmol, 1.7 equiv) in THF (300 mL) dropwise at −78° C. under nitrogen atmosphere. After stirring for 1 hour at −78° C.~−70° C., the reaction was quenched with HCl aq. Solution (0.5 M, 200 mL) and then stirred at 0° C. for 1 h. The resulting mixture was extracted with EtOAc. The combined organic layers were washed with brine, dried over anhydrous Na$_2$SO$_4$ and concentrated. The residue was purified by silica gel column chromatography, eluted with EtOAc/PE (20%-50%) to afford the title compound 0.8 g (26.6%) as a light yellow solid. MS (ES, m z): [M+1]$^+$=295.

Step 6: 6-bromo-7-(difluoromethyl)-2,2-difluorobenzo[b]thiophen-3(2H)-one 1-oxide

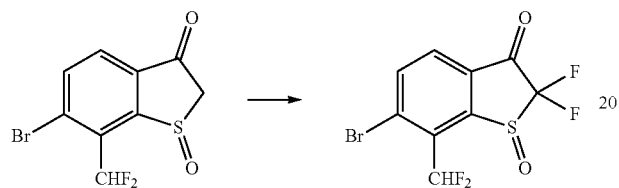

To a stirred solution of 6-bromo-7-(difluoromethyl)benzo[b]thiophen-3(2H)-one 1-oxide (0.8 g, 2.71 mmol, 1.0 equiv) in ACN (15 mL) were added selectfluor (2.11 g, 5.96 mmol, 2.2 equiv) and Na$_2$CO$_3$ (0.63 g, 5.96 mmol, 2.2 equiv) at room temperature under nitrogen atmosphere. After stirring for 2 h at room temperature, the reaction mixture was concentrated under reduced pressure. The residue was purified by silica gel column chromatography, eluted with PE/EtOAc (20%-50%) to afford the title compound (0.8 g) as a light yellow solid. MS (ES, m z): [M+1]$^+$=331.

Step 7: 3-chloro-5-((7-(difluoromethyl)-2,2-difluoro-1-oxido-3-oxo-2,3-dihydrobenzo[b]thiophen-6-yl)oxy)benzonitrile

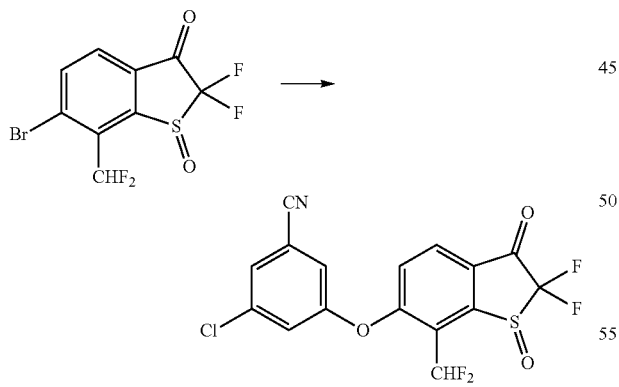

To a stirred solution of 6-bromo-7-(difluoromethyl)-2,2-difluorobenzo[b]thiophen-3(2H)-one 1-oxide (40 mg, 0.12 mmol, 1.0 equiv) and 3-chloro-5-hydroxybenzonitrile (18.55 mg, 0.12 mmol, 1.0 equiv) in DMF (1 mL) was added Cs$_2$CO$_3$ (43.30 mg, 0.13 mmol, 1.1 equiv) at room temperature under nitrogen atmosphere. After stirring at rt for 2 h, the reaction was quenched with water and extracted with EtOAc. The combined organic layers were washed with brine, dried over anhydrous Na$_2$SO$_4$ and concentrated. The residue was purified by silica gel column chromatography, eluted with EtOAc/PE (10%-30%) to afford the title compound (35 mg, 71.75%) as a light yellow solid. MS (ES, m/z): [M+1]=404.

Example 5

Synthesis of 3-chloro-5-((7-(difluoromethyl)-2,2-difluoro-3-hydroxy-1-oxido-2,3-dihydrobenzo[b]thiophen-6-yl)oxy)benzonitrile

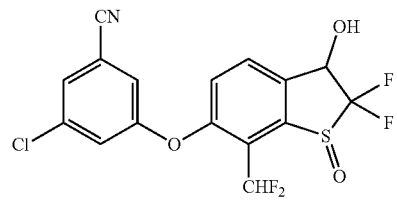 [SMILES: N#Cc1cc(Cl)cc(Oc2ccc3c(c2C(F)F)S(=O)C(F)(F)C3O)c1]

To a stirred solution of 3-chloro-5-((7-(difluoromethyl)-2,2-difluoro-1-oxido-3-oxo-2,3-dihydrobenzo[b]thiophen-6-yl)oxy)benzonitrile (75 mg, 0.186 mmol, 1.0 equiv) in MeOH (1 mL) was added NaBH$_4$ (14.06 mg, 0.372 mmol, 2.0 equiv) at room temperature. After stirring for 1 h at room temperature, the reaction was quenched with sat. NH$_4$Cl aq. solution at 0° C. The resulting mixture was extracted with EtOAc. The combined organic layers were washed with brine, dried over anhydrous Na$_2$SO$_4$ and concentrated to afford the title compound (65 mg, 86.2%) as a white solid. MS (ES, m/z): [M+1]$^+$=406.

Example 6

Synthesis of 3-chloro-5-(((1R,3R)-7-(difluoromethyl)-2,2,3-trifluoro-1-oxido-2,3-dihydrobenzo[b]thiophen-6-yl)oxy)benzonitrile (6a), 3-chloro-5-(((1S,3S)-7-(difluoromethyl)-2,2,3-trifluoro-1-oxido-2,3-dihydrobenzo[b]thiophen-6-yl)oxy)benzonitrile (6b), 3-chloro-5-(((1S,3R)-7-(difluoromethyl)-2,2,3-trifluoro-1-oxido-2,3-dihydrobenzo[b]thiophen-6-yl)oxy)benzonitrile (6c) and 3-chloro-5-(((1R,3S)-7-(difluoromethyl)-2,2,3-trifluoro-1-oxido-2,3-dihydrobenzo[b]thiophen-6-yl)oxy)benzonitrile (6d)

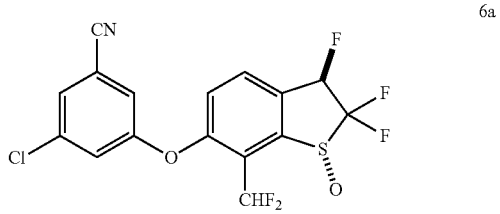

6a

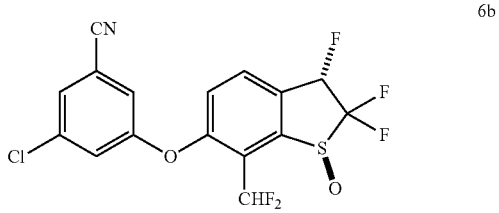

6b

-continued

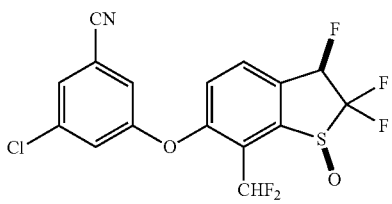
6c

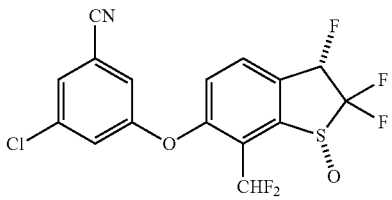
6d

To a stirred solution of 3-chloro-5-((7-(difluoromethyl)-2,2-difluoro-3-hydroxy-1-oxido-2,3-dihydrobenzo[b]thiophen-6-yl)oxy)benzonitrile (65 mg, 0.16 mmol, 1.0 equiv) in DCM (1 mL) was added DAST (38.73 mg, 0.24 mmol, 1.5 equiv) dropwise room temperature under nitrogen atmosphere. After stirring for 2 h at room temperature, the reaction was quenched with sat. NaHCO$_3$ aq. solution at 0° C. The resulting mixture was extracted with CH$_2$Cl$_2$. The combined organic layers were washed with brine, dried over anhydrous Na$_2$SO$_4$ and concentrated. The crud product (70 mg) was purified by Chiral-HPLC to afford four enantiomerically pure compounds. The compound numbers below are arbitrarily assigned to specific enantiomers since the configuration of these isomers has not been established.

Separation condition: Chiral HPLC CHIRALPAK AD-3; flow rate: 1.0 mL/min; EtOH/Hexane 20%. Retention times of the four isomers were: $t_R$=1.7 min, 2.0 min, 2.5 min, 3.4 min and their MS (ES, m z): [M−1]$^−$=406.

Example 7

Synthesis of 7-(difluoromethyl)-6-(3,5-difluorophenoxy)-2,2-difluorobenzo[b]thiophen-3(2H)-one 1-oxide

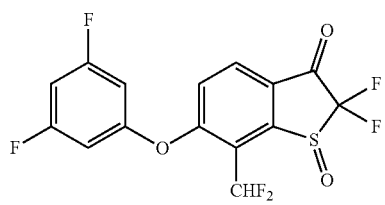 [SMILES: O=C1c2ccc(Oc3cc(F)cc(F)c3)c(C(F)F)c2S(=O)C1(F)F]

To a stirred mixture of 6-bromo-7-(difluoromethyl)-2,2-difluorobenzo[b]thiophen-3(2H)-one 1-oxide (0.1 g, 0.30 mmol, 1.0 equiv) and 3,5-difluorophenol (43.22 mg, 0.33 mmol, 1.1 equiv) in DMF (1 mL) was added Cs$_2$CO$_3$ (108.25 mg, 0.33 mmol, 1.10 equiv) at room temperature. After stirring for 2 h at room temperature, the reaction was quenched with water at 0° C. The resulting mixture was extracted with EtOAc. The combined organic layers were washed with brine, dried over anhydrous Na$_2$SO$_4$ and concentrated. The residue was purified by silica gel column chromatography, eluted with EtOAc/PE (10%-40%) to afford the title compound 90 mg (78.4%) as a light yellow solid. MS (ES, m/z): [M+1]=381.

Example 8

Synthesis of 7-(difluoromethyl)-6-(3,5-difluorophenoxy)-2,2-difluoro-3-hydroxy-2,3-dihydrobenzo[b]thiophene 1-oxide

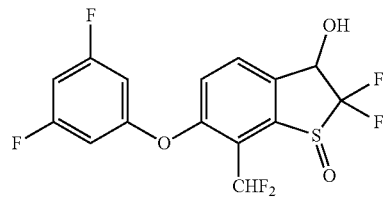 [SMILES: O=S1c2c(ccc(Oc3cc(F)cc(F)c3)c2C(F)F)C(O)C1(F)F]

To a stirred solution of 7-(difluoromethyl)-6-(3,5-difluorophenoxy)-2,2-difluorobenzo[b]-thiophen-3(2H)-one 1-oxide (90 mg, 0.23 mmol, 1.00 equiv) in THF (2 mL) was added L-selectride (0.28 mL, 0.28 mmol, 1.20 equiv) dropwise in portions at 0° C. under nitrogen atmosphere. After stirring for 2 h at room temperature, the reaction was quenched with sat. NH$_4$C aq. solution at 0° C. and the resulting mixture was extracted with EtOAc. The combined organic layers were washed with brine, dried over anhydrous Na$_2$SO$_4$ and concentrated. The residue was purified by silica gel column chromatography, eluted with EtOAc/PE (10%-35%) to afford the title compound 70 mg (77.4%) as a light yellow oil. MS (ES, m/z): [M+1]$^+$=383.

Example 9

Synthesis of (1S,3S)-7-(difluoromethyl)-6-(3,5-difluorophenoxy)-2,2,3-trifluoro-2,3-dihydrobenzo[b]thiophene 1-oxide (9a) and (1R,3R)-7-(difluoromethyl)-6-(3,5-difluorophenoxy)-2,2,3-trifluoro-2,3-dihydrobenzo[b]thiophene 1-oxide (9b) and (1R,3S)-7-(difluoromethyl)-6-(3,5-difluorophenoxy)-2,2,3-trifluoro-2,3-dihydrobenzo[b]thiophene 1-oxide (9c) and (1R,3S)-7-(difluoromethyl)-6-(3,5-difluorophenoxy)-2,2,3-trifluoro-2,3-dihydrobenzo[b]thiophene 1-oxide (9d)

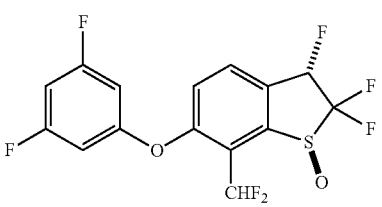
9a

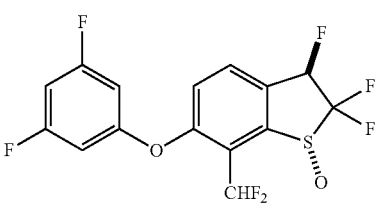
9b

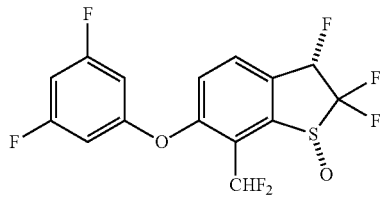

9c

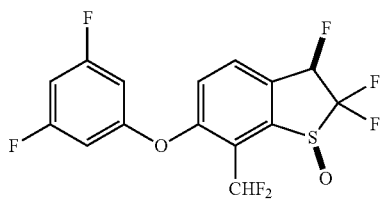

9d

To a stirred solution of 7-(difluoromethyl)-6-(3,5-difluorophenoxy)-2,2-difluoro-3-hydroxy-2,3-dihydrobenzo[b]thiophene 1-oxide (70 mg, 0.18 mmol, 1.0 equiv) in DCM (1.0 mL) was added DAST (44.27 mg, 0.27 mmol, 1.5 equiv) dropwise at rt under nitrogen atmosphere. After stirring for 2 h at rt, the reaction was cooled at 0° C. and quenched with sat. NaHCO$_3$ aq. solution. The resulting mixture was extracted with CH$_2$Cl$_2$. The combined organic layers were washed with brine, dried over anhydrous Na$_2$SO$_4$ and concentrated. The crude material (60 mg) was purified by Chiral-HPLC to afford four enantiomerically pure compounds. The compound numbers are arbitrarily assigned to specific enantiomers since the configuration of these isomers has not been established.

Separation condition: Chiral HPLC CHIRALCEL OD-3; flow rate: 1.0 mL/min; EtOH/Hexane 5%. Retention times for the four isomers were $t_R$: 1.7 min, 2.1 min, 2.9 min, 4.2 min and their MS (ES, m/z) [M+1]$^+$=383.

Example 10

Synthesis of 6-(3-chloro-5-fluorophenoxy)-7-(difluoromethyl)-2,2-difluorobenzo[b]thiophen-3(2H)-one 1-oxide

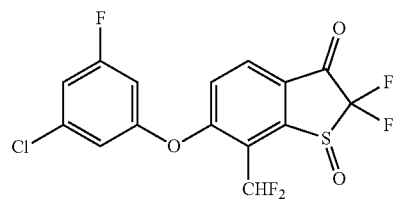 [SMILES: O=C1c2ccc(Oc3cc(F)cc(Cl)c3)c(C(F)F)c2S(=O)C1(F)F]

To a stirred mixture of 6-bromo-7-(difluoromethyl)-2,2-difluorobenzo[b]thiophen-3(2H)-one 1-oxide (0.2 g, 0.60 mmol, 1.0 equiv) and 3-chloro-5-fluorophenol (97.38 mg, 0.66 mmol, 1.1 equiv) in DMF (2 mL) was added Cs$_2$CO$_3$ (216.50 mg, 0.66 mmol, 1.1 equiv) at rt. After stirring for 2 h at rt, the reaction was quenched with water at 0° C. The resulting mixture was extracted with EtOAc. The combined organic layers were washed with brine, dried over anhydrous Na$_2$SO$_4$ and concentrated. The residue was purified by silica gel column chromatography, eluted with PE/EtOAc (3:1) to afford the title compound (0.17 g, 70.94%) as a light yellow solid. MS (ES, m/z): [M+1]$^+$=396.9.

Example 11

Synthesis of 6-(3-chloro-5-fluorophenoxy)-7-(difluoromethyl)-2,2-difluoro-3-hydroxy-2,3-dihydrobenzo[b]thiophene 1-oxide

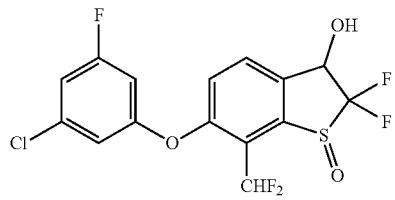

To a stirred solution of 6-(3-chloro-5-fluorophenoxy)-7-(difluoromethyl)-2,2-difluorobenzo[b]thiophen-3(2H)-one 1-oxide (100 mg, 0.25 mmol, 1.0 equiv) in THF (2 mL) was added L-selectride (0.30 mL, 0.30 mmol, 1.2 equiv) at 0° C. under nitrogen atmosphere. After stirring for 2 h at room temperature, the reaction was quenched with sat. NH$_4$Cl aq. solution at 0° C. and then extracted with EtOAc. The combined organic layers were washed with brine, dried over anhydrous Na$_2$SO$_4$ and concentrated. The residue was purified by silica gel column chromatography, eluted with PE/EtOAc (3:1) to afford the title compound (70 mg, 69.6%) as a light yellow oil. MS (ES, m/z): [M+1]=400.0.

Example 12

Synthesis of (1S,3S)-6-(3-chloro-5-fluorophenoxy)-7-(difluoromethyl)-2,2,3-trifluoro-2,3-dihydrobenzo[b]thiophene 1-oxide (12a) and (1R,3R)-6-(3-chloro-5-fluorophenoxy)-7-(difluoromethyl)-2,2,3-trifluoro-2,3-dihydrobenzo[b]thiophene 1-oxide (12b) and (1R,3S)-6-(3-chloro-5-fluorophenoxy)-7-(difluoromethyl)-2,2,3-trifluoro-2,3-dihydrobenzo[b]thiophene 1-oxide (12c) and (1S,3R)-6-(3-chloro-5-fluorophenoxy)-7-(difluoromethyl)-2,2,3-trifluoro-2,3-dihydrobenzo[b]thiophene 1-oxide (12d)

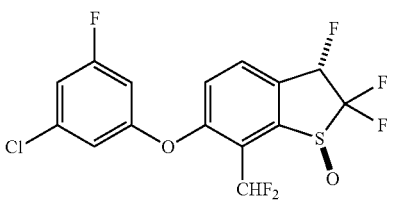

12a

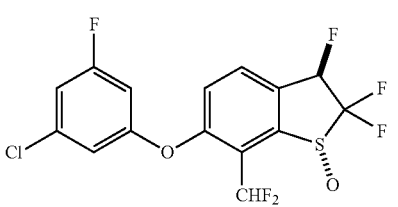

12b

73
-continued

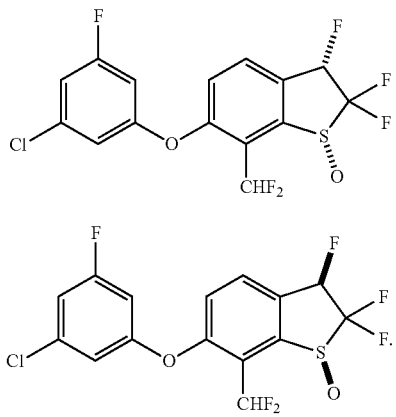

12c

12d

To a stirred solution of 6-(3-chloro-5-fluorophenoxy)-7-(difluoromethyl)-2,2-difluoro-3-hydroxy-2,3-dihydrobenzo[b]thiophene 1-oxide (70 mg, 0.17 mmol, 1.0 equiv) in DCM (1 mL) was added DAST (42.45 mg, 0.26 mmol, 1.5 equiv) dropwise at rt under nitrogen atmosphere. After stirring for 2 h at rt, the reaction was quenched with sat. $NaHCO_3$ aq. solution at 0° C. The resulting mixture was extracted with $CH_2Cl_2$. The combined organic layers were washed with brine, dried over anhydrous $Na_2SO_4$ and concentration. The crude material was purified by Chiral-HPLC to afford four enantiomerically pure compounds. The compound numbers are arbitrarily assigned to specific enantiomers since the configuration of each isomer has not been established.

Separation condition: Chiral HPLC CHIRALCEL OD; Flow rate: 1.0 ml/min; IPA/hexane 8%. Retention times for the four isomers were: $t_R$: 1.7, 2.1, 3.2, 4.5 min; and their MS (ES, m z) $[M-1]^-=399$;

Example 13

Synthesis of (R)-3-((7-(difluoromethyl)-2,2,3,3-tetrafluoro-1-oxido-2,3-dihydrobenzo[b]thiophen-6-yl)oxy)-5-fluorobenzonitrile and (S)-3-((7-(difluoromethyl)-2,2,3,3-tetrafluoro-1-oxido-2,3-dihydrobenzo[b]thiophen-6-yl)oxy)-5-fluorobenzonitrile

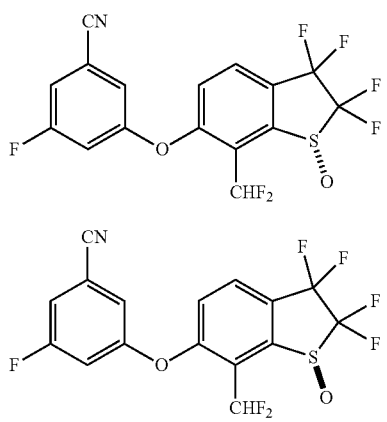

13a

13b

74

Step 1: 1-(2-bromo-5-fluorophenoxy)-N,N-dimethylmethanethioamide

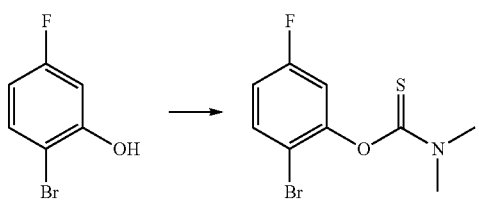

Into a 500-mL 4-necked round-bottom flask, was placed DMF (200 mL), 2-bromo-5-fluorophenol (30 g, 0.157 mol, 1 equiv), DABCO (35.24 g, 0.314 mol, 2 equiv), and (chloromethanethioyl)dimethylamine (38.83 g, 0.314 mol, 2.00 equiv). The resulting solution was stirred for 16 h at 20° C. and then diluted with $H_2O$. The resulting solution was extracted with of ethyl acetate and the organic layer was washed with of brine. The residue was applied onto a silica gel column and eluted with ethyl acetate/petroleum ether (1:5). The collected fractions were combined and concentrated to give 21 g of the title compound as a white solid.

Step 2: 1-[(2-bromo-5-fluorophenyl)sulfanyl]-N,N-dimethylformamide

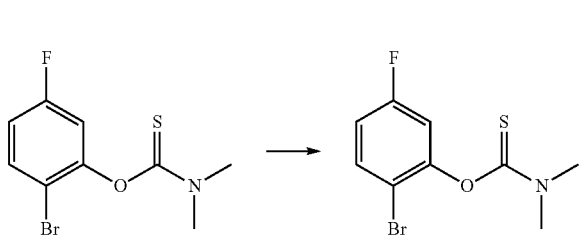

Into a 250-mL 4-necked round-bottom flask, was placed 1-(2-bromo-5-fluorophenoxy)-N,N dimethylmethanethioamide (21 g, 75.502 mmol, 1.0 equiv) and phenoxybenzene (80 mL). The resulting solution was stirred for 3 h at 250° C. in a heating jacket bath. The residue was applied onto a silica gel column and eluted with ethyl acetate/petroleum ether (1:5). The collected fractions were combined and concentrated to give 11 g (52%) of the title compound as a white solid.

Step 3: 2-bromo-5-fluorobenzene-1-thiol

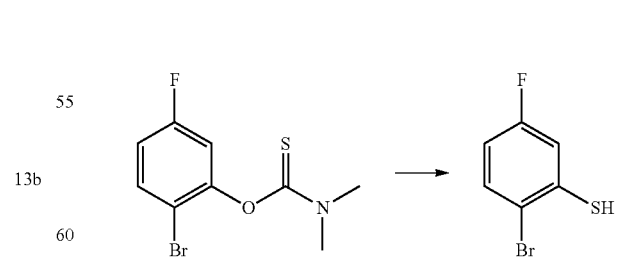

Into a 250-mL 4-necked round-bottom flask, was placed MeOH (80 mL), 1-[(2-bromo-5-fluorophenyl)sulfanyl]-N,N-dimethylformamide (11 g, 39.548 mmol, 1.0 equiv), and NaOH (1M aq. solution) (3.95 g, 98.871 mmol, 2.5 equiv). The resulting solution was stirred for 3 h at 50° C. in an oil bath. After cooling the reaction mixture to rt, the reaction was acidified to pH=2 by adding aq. HCl solution (1.0 M). The resulting solution was extracted with ethyl acetate and the organic layers were combined and concentrated. The residue was applied onto a silica gel column and eluted with ethyl acetate/petroleum ether (1:10) to give 6.0 g (73.2%) of the title compound as colorless oil.

Step 4: 1-bromo-2-[(2-bromo-1,1,2,2-tetrafluoroethyl)sulfanyl]-4-fluorobenzene

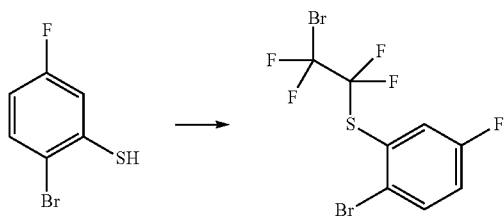 [SMILES: Fc1ccc(Br)c(S)c1 ; Fc1ccc(Br)c(SC(F)(F)C(F)(F)Br)c1]

To a stirred solution of 2-bromo-5-fluorobenzene-1-thiol (1.1 g, 5.31 mmol, 1.0 equiv) in DMF (15 mL) was added NaH (0.3 g, 7.97 mmol, 1.5 equiv, 60% in oil) in portions at −40° C.~ 0° C. and the resulting mixture was stirred at 0° C. for 30 mins. To the above mixture was added 1,2-dibromo-1,1,2,2-tetrafluoroethane (1.7 g, 6.64 mmol, 1.25 equiv) dropwise at −40° C. The resulting mixture was allowed to warm to 0° C. and stirred for additional 3 h at 0° C. The reaction mixture was quenched by the addition of water at 0° C. and the resulting mixture was extracted with EtOAc. The combined organic layers were washed with brine, dried over anhydrous $Na_2SO_4$. After filtration, the filtrate was concentrated under reduced pressure and the residue was purified by silica gel column chromatography, with PE as eluent to afford 1.2 g (58.5%) of the title compound as a light yellow oil.

Step 5: 2,2,3,3,6-pentafluoro-2,3-dihydro-1-benzothiophene

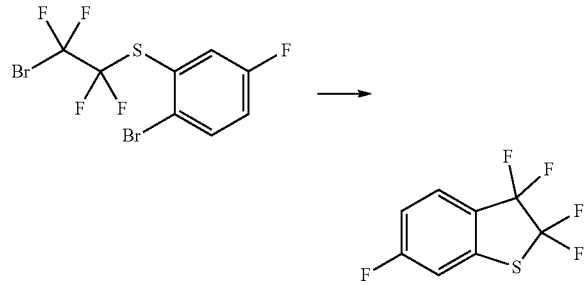

To a stirred mixture of 1-bromo-2-[(2-bromo-1,1,2,2-tetrafluoroethyl)sulfanyl]-4-fluoro-benzene (0.9 g, 2.33 mmol, 1 equiv) and Cu (0.7 g, 11.66 mmol, 5 equiv) in DMSO (5 mL) was added 2,2-bipyridine (36.4 mg, 0.23 mmol, 0.1 equiv) at room temperature under nitrogen atmosphere. The resulting mixture was stirred for 1.5 h at 150° C. under nitrogen atmosphere. After cooling the reaction mixture to rt, the mixture was diluted with water/EtOAc and filtered. The filtrate was extracted with EtOAc and the combined organic layers were washed with brine and dried over anhydrous $Na_2SO_4$. After filtration, the filtrate was concentrated under reduced pressure. The residue was purified by silica gel column chromatography, with hexane as eluent to afford 0.24 g (45.5%) of the title compound as a light-yellow oil.

Step 6: 2,2,3,3,6-pentafluoro-2,3-dihydro-1-benzothiophene-7-carbaldehyde

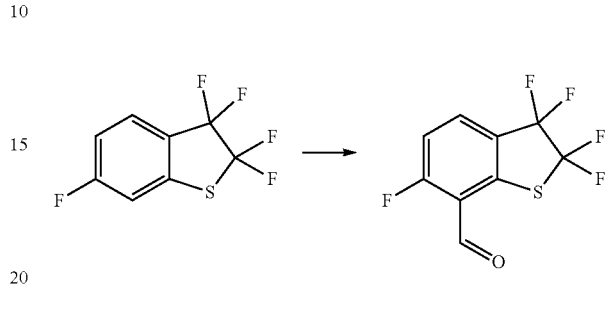

To a stirred solution of 2,2,3,3,6-pentafluoro-2,3-dihydro-1-benzothiophene (0.24 g, 1.06 mmol, 1.0 equiv) in THF (5 mL) was added LDA (0.85 mL, 1.7 mmol) dropwise at −78° C. under nitrogen atmosphere. The reaction mixture was stirred at −78° C.~−60° C. for 30 minutes. To the above mixture was added DMF (0.2 mL, 1.37 mmol, 1.22 equiv) dropwise over 5 minutes at −78° C. The resulting mixture was stirred for additional 5 minutes at −78° C. and the reaction mixture was poured into 0.5 M HCl aq. solution. The mixture was extracted with EtOAc and the combined organic layers were washed with brine and, dried over anhydrous $Na_2SO_4$. After filtration, the filtrate was concentrated under reduced pressure to afford 120 mg of the title compound as a light yellow oil.

Step 7: 7-(difluoromethyl)-2,2,3,3,6-pentafluoro-2,3-dihydro-1-benzothiophene

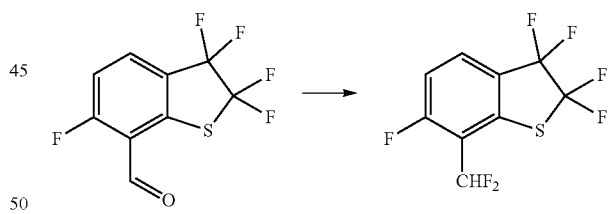

To a stirred solution of 2,2,3,3,6-pentafluoro-2,3-dihydro-1-benzothiophene-7-carbaldehyde (120 mg, 0.472 mmol, 1.0 equiv) in DCM (4 mL) was added DAST (190.25 mg, 1.180 mmol, 2.5 equiv) dropwise at room temperature under nitrogen atmosphere. After stirring for 2 h, the reaction was quenched with sat. $NaHCO_3$ (aq.) at room temperature. The resulting mixture was extracted with $CH_2Cl_2$ and the combined organic layers were washed with brine and dried over anhydrous $Na_2SO_4$. After filtration, the filtrate was concentrated under reduced pressure. The residue was purified by silica gel column chromatography eluting with PE/EtOAc (10:1) to afford 35 mg of the title compound as a light yellow oil.

Step 8: 3-[[7-(difluoromethyl)-2,2,3,3-tetrafluoro-2,3-dihydro-1-benzothiophen-6-yl]oxy]-5-fluorobenzonitrile

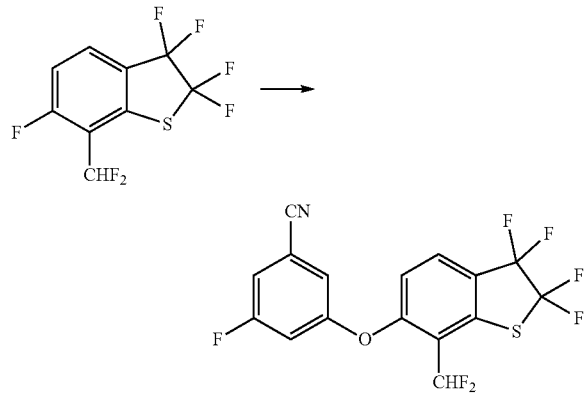

To a stirred mixture of 7-(difluoromethyl)-2,2,3,3,6-pentafluoro-2,3-dihydro-1-benzothiophene (35 mg, 0.127 mmol, 1.0 equiv) and Cs$_2$CO$_3$ (41.29 mg, 0.127 mmol, 1.0 equiv) in DMF (1 mL) was added 3-fluoro-5-hydroxybenzonitrile (17.38 mg, 0.127 mmol, 1.0 equiv) at room temperature under nitrogen atmosphere. After stirring for 5 h at room temperature, the reaction was quenched with water at room temperature. The resulting mixture was extracted with EtOAc. The combined organic layers were washed with brine, dried over anhydrous Na$_2$SO$_4$ and concentrated. The residue was purified by silica gel column chromatography by eluting with PE/EtOAc (10:1) to afford the title compound 35 mg (70.22%) as a light yellow oil.

Step 9: (R)-3-((7-(difluoromethyl)-2,2,3,3-tetrafluoro-1-oxido-2,3-dihydrobenzo[b]thiophen-6-yl)oxy)-5-fluorobenzonitrile (13a) and (S)-3-((7-(difluoromethyl)-2,2,3,3-tetrafluoro-1-oxido-2,3-dihydrobenzo[b]thiophen-6-yl)oxy)-5-fluorobenzonitrile (13b)

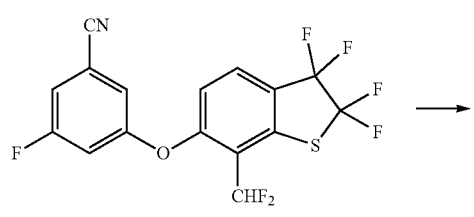

13a

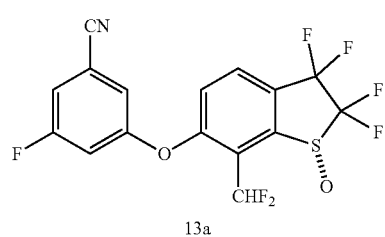

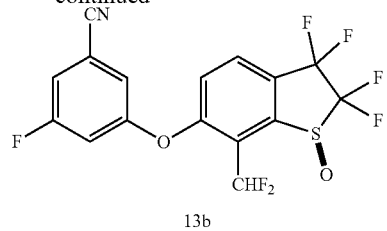

13b

To a stirred solution of 3-[[7-(difluoromethyl)-2,2,3,3-tetrafluoro-2,3-dihydro-1-benzothiophen-6-yl]oxy]-5-fluorobenzonitrile (35 mg, 0.089 mmol, 1.0 equiv) in CH$_3$COOH (1 mL) was added H$_2$O$_2$(0.3 mL, 30%) dropwise at room temperature. After stirring for 1 h at 90° C. the reaction was quenched with water at room temperature. The resulting mixture was extracted with EtOAc. The combined organic layers were washed with brine, dried over anhydrous Na$_2$SO and concentrated. The crude product was purified by Prep-HPLC to afford 16 mg (43.9%) of the the title compound as a white solid. The product was further separated by chiral HPLC to afford two enantiomers. The compound numbers are arbitrarily assigned to specific enantiomers since the absolute configuration of these isomers was not established.

Separation condition: CHIRALPAK IC-3 column; Flow rate: 1.0 ml/min; EtOH/hexane 20%.

One of 13a and 13b has $t_R$=1.7 min; MS (ES, m z): [M−1]$^-$=408;

The other of 13a and 13b: $t_R$=2.1 min; MS (ES, m z): [M−1]$^-$=408.

Example 14

Synthesis of 7-(difluoromethyl)-6-(3,5-difluorophenoxy)-2,2,3,3-tetrafluoro-2,3-dihydrobenzo[b]thiophene 1-oxide

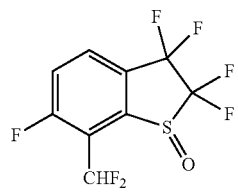

To a stirred solution of 7-(difluoromethyl)-2,2,3,3,6-pentafluoro-2,3-dihydro-1-benzothiophene (200 mg, 1.0 equiv) in AcOH (1.2 mL) were added 30% H$_2$O$_2$(0.4 mL). The resulting mixture was stirred for 3 h at 90° C. under air atmosphere. The resulting mixture was added brine and then extracted with EtOAc. The combined organic layers were concentrated and the residue was purified by silica gel column chromatography, eluted with PE/EtOAc (10:1) to afford the title compound (150 mg,70%) as a colorless oil.
$^1$HNMR (300 MHz, CDCl$_3$) δ 8.04 (ddq, J=8.8, 4.4, 1.1 Hz, 1H), 7.71-7.61 (m, 1H), 7.43-7.01 (m, 1H).

Example 15

Synthesis of 7-(difluoromethyl)-6-(3,5-difluorophenoxy)-2,2,3,3-tetrafluoro-2,3-dihydrobenzo[b]thiophene 1-oxide

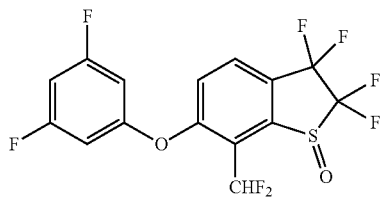

To a stirred solution of 7-(difluoromethyl)-2,2,3,3,6-pentafluoro-2,3-dihydrobenzo-[b]thiophene 1-oxide (15 mg, 0.05 mmol, 1.0 equiv) and 3,5-difluorophenol (10.02 mg, 0.08 mmol, 1.5 equiv) in ACN (0.30 mL) were added Cs$_2$CO$_3$ (50.18 mg, 0.15 mmol, 3.0 equiv) in portions at rt under air atmosphere. After stirring at 70° C. for 2 h, the resulting mixture was cooled at rt and filtered. The filtrate was concentrated and purified by Prep-HPLC to afford the title product (5 mg) as a white solid. MS (ES, m z): [M−1]$^−$=400.9.

Example 16

Synthesis of 5-((7-(difluoromethyl)-2,2,3,3-tetrafluoro-1-oxido-2,3-dihydrobenzo[b]thiophen-6-yl)oxy)nicotinonitrile

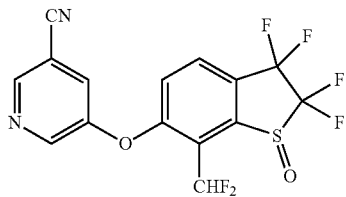

The title compound was synthesized followed by the method described in Example 15 using 5-hydroxynicotinonitrile instead of 3,5-difluorophenol. MS (ES, m z): [M+H]$^+$=393.0.

Example 17

Synthesis of 7-(difluoromethyl)-2,2,3,3-tetrafluoro-6-((5-fluoropyridin-3-yl)oxy)-2,3-dihydrobenzo[b]thiophene 1-oxide

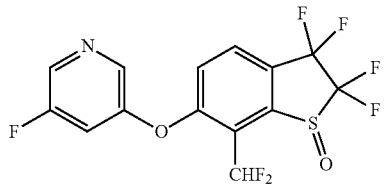 [SMILES: O=S1c2c(ccc(Oc3cncc(F)c3)c2C(F)F)C(F)(F)C1(F)F]

The title compound was synthesized followed by the method described in Example 15 using 5-fluoropyridin-3-ol instead of 3,5-difluorophenol. MS (ES, m z): [M+1]$^+$=386.0.

Example 18

Synthesis of 6-((5-chloropyridin-3-yl)oxy)-7-(difluoromethyl)-2,2,3,3-tetrafluoro-2,3-dihydrobenzo[b]thiophene 1-oxide

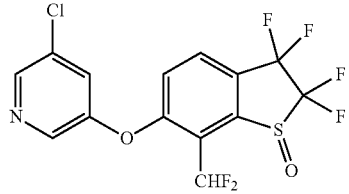 [SMILES: O=S1c2c(ccc(Oc3cncc(Cl)c3)c2C(F)F)C(F)(F)C1(F)F]

The title compound was synthesized followed by the method described in Example 15 using 5-chloropyridin-3-ol instead of 3,5-difluorophenol. MS (ES, m z): [M−1]$^−$=399.9.

Example 19

Synthesis of 6-(3,3-difluorocyclobutoxy)-7-(difluoromethyl)-2,2,3,3-tetrafluoro-2,3-dihydrobenzo[b]thiophene 1-oxide [3.6]

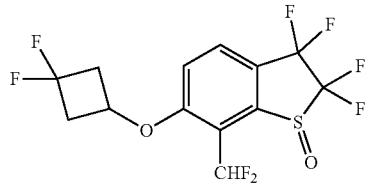 [SMILES: O=S1c2c(ccc(OC3CC(F)(F)C3)c2C(F)F)C(F)(F)C1(F)F]

The title compound was synthesized followed by the method described Example 15 using 3,3-difluorocyclobutan-1-ol instead of 3,5-difluorophenol. MS (ES, m z): [M+41+1]$^+$=422.1.

Example 20

Synthesis of 3-((7-(difluoromethyl)-2,2,3,3-tetrafluoro-1,1-dioxido-2,3-dihydrobenzo-[b]thiophen-6-yl)oxy)-5-fluorobenzonitrile

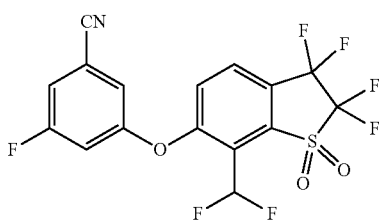 [SMILES: N#Cc1cc(F)cc(Oc2ccc3c(c2C(F)F)S(=O)(=O)C(F)(F)C3(F)F)c1]

Step 1: 7-(difluoromethyl)-2,2,3,3,6-pentafluoro-2,
3-dihydrobenzo[b]thiophene 1,1-dioxide

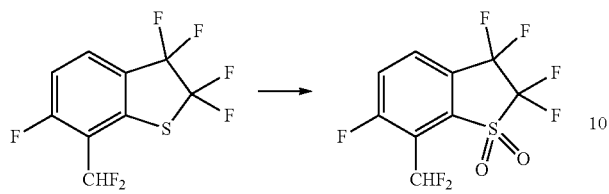

Into an 8-mL vial, was placed 7-(difluoromethyl)-2,2,3,3,6-pentafluoro-2,3-dihydro-1-benzothiophene (50 mg, 0.18 mmol, 1.0 equiv), AcOH (2 mL), KMnO$_4$ (228 mg, 1.45 mmol, 8.0 equiv). The resulting mixture was stirred at 100° C. for 30 mins. The resulting solution was diluted with water and extracted ethyl acetate. The organic layers were combined and concentrated under vacuum. The residue was purified by silica gel column chromatography, eluting with ethyl acetate/petroleum ether (1/1) to afford 35 mg (62.7%) of the title compound as light yellow oil. GCMS (EI): [M]=308.

Step 2: 3-((7-(difluoromethyl)-2,2,3,3-tetrafluoro-1,1-dioxido-2,3-dihydrobenzo[b]thiophen-6-yl)oxy)-5-fluorobenzonitrile

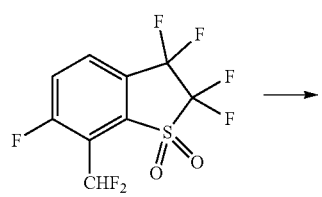

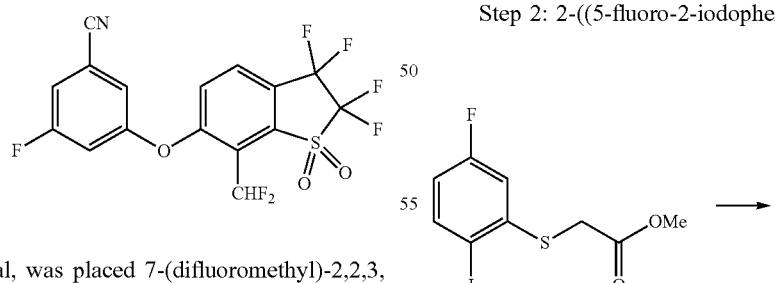

Into an 8-mL vial, was placed 7-(difluoromethyl)-2,2,3,3,6-pentafluoro-2,3-dihydrobenzo-[b]thiophene 1,1-dioxide (35 mg, 0.11 mmol, 1.0 equiv), Cs$_2$CO$_3$ (74 mg, 0.23 mmol, 2.0 equiv), DMF (1 mL), 3-fluoro-5-hydroxybenzonitrile (23.4 mg, 0.17 mmol, 1.5 equiv). The resulting mixture was stirred at 100° C. for 16 h. After cooled at rt, the reaction mixture was filtered and the filtrate was concentrated under vacuum. The crude material was purified by Prep-HPLC to afford 19 mg (39.34%) of the title compound as a white solid. MS (ES, m z): [M+1]$^+$=424.

Example 21

Synthesis of 3-((2,2-difluoro-7-iodo-1-oxido-3-oxo-2,3-dihydrobenzo[b]thiophen-4-yl)oxy)-5 fluorobenzonitrile

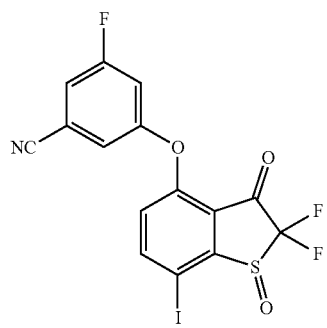 [SMILES: N#Cc1cc(F)cc(Oc2ccc(I)c3c2C(=O)C(F)(F)S3=O)c1]

Step 1: methyl 2-((5-fluoro-2-iodophenyl)thio)acetate

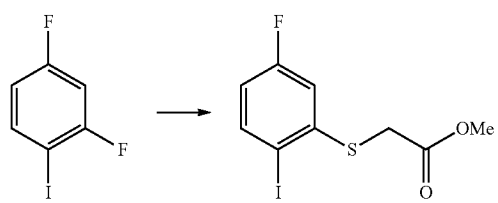 [SMILES: Fc1ccc(I)c(F)c1 ; COC(=O)CSc1cc(F)ccc1I]

Into a 250-mL round-bottom flask, was placed 2,4-difluoro-1-iodobenzene (10 g, 41.6 mmol, 1.0 equiv), DMF (150 mL), K$_3$PO$_4$ (10.613 g, 50 mmol, 1.2 equiv), methyl 2-sulfanylacetate (5.307 g, 50 mmol, 1.2 equiv). After stirring at rt for 24 h, the reaction mixture was diluted with water and extracted PE/EA (3/1). The organic layers were combined, dried over anhydrous sodium sulfate and concentrated in vacuum. The residue was purified by silica gel column chromatography, eluting with ethyl acetate/petroleum ether (1/10) to afford 2.8 g (20.6%) of the title compound.

Step 2: 2-((5-fluoro-2-iodophenyl)thio)acetic acid

Into a 100-mL round-bottom flask, was placed methyl 2-[(5-fluoro-2-iodophenyl)sulfanyl]-acetate (2.8 g, 8.58 mmol, 1.0 equiv), THF (40 mL), water (20 mL), lithium hydroxide monohydrate (1.08 g, 25.757 mmol, 3.0 equiv) and the resulting solution was stirred for 16 h at room temperature. The reaction mixture was then acidified to pH=5 with HCl aq. solution (1.0 M). The resulting solution was extracted with ethyl acetate. The combined organic layer was dried over anhydrous sodium sulfate and concentrated under vacuum. The residue was washed with a mixed solution of PE/EA=20/1 and filtered to afford 2.25 g (83.9%) of the title compound as a white solid.

Step 3: 4-fluoro-7-iodobenzo[b]thiophen-3(2H)-one

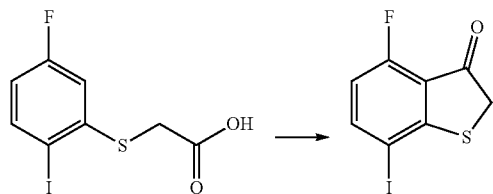 [SMILES: O=C(O)CSc1cc(F)ccc1I ; O=C1CSc2c(I)ccc(F)c21]

Into a 40-mL vial, was placed 2-[(5-fluoro-2-iodophenyl)sulfanyl]acetic acid (2.2 g, 7.049 mmol, 1.0 equiv), 1,2-dichlorobenzene (7 mL), N,N-dimethylformamide (26 mg, 0.352 mmol, 0.05 equiv), thionyl chloride (922 mg, 7.754 mmol, 1.1 equiv). The resulting solution was stirred for 1 h at 60° C. in an oil bath. The reaction was cooled to rt and added a mixture of trichloroalumane (1.4 g, 10.574 mmol, 1.5 equiv) in 1,2-dichlorobenzene (5 mL), while the temperature maintained at 0-10° C. The resulting mixture was stirred for an additional 1.5 h and then poured into ice. The precipitate was collected by filtration, washed with water and PE. The collected solid was then dried to give 1.6 g (77.18%) of the title compound.

Step 4: 4-fluoro-7-iodobenzo[b]thiophen-3(2H)-one 1-oxide

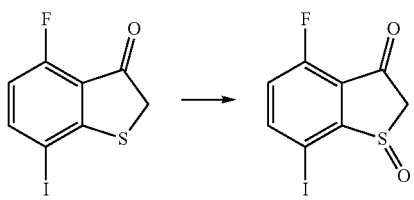 [SMILES: O=C1CSc2c(I)ccc(F)c21 ; O=C1CS(=O)c2c(I)ccc(F)c21]

Into a 50-mL round-bottom flask, was placed 4-fluoro-7-iodo-2,3-dihydro-1-benzothiophen-3-one (1000 mg, 3.400 mmol, 1.0 equiv), DCM (15 mL), acetic acid (5 mL), 30% H$_2$O$_2$(771 mg, 22.667 mmol, 6.67 equiv) and the resulting solution was stirred for 4 h at 50° C. in an oil bath.

After cooling the reaction mixture to rt, the reaction mixture as neutralized to pH=7 by adding Na$_2$CO$_3$. The resulting mixture was diluted with water and extracted with DCM. The organic layer was combined and dried over anhydrous sodium sulfate, concentrated under vacuum. The residue was purified by silica gel column chromatography with ethyl acetate/petroleum ether (1:2) to afford 780 mg (73.9%) of the title compound. MS (ES, m z): [M+1]$^+$=311.0.

Step 5: 2,2,4-trifluoro-7-iodobenzo[b]thiophen-3(2H)-one 1-oxide

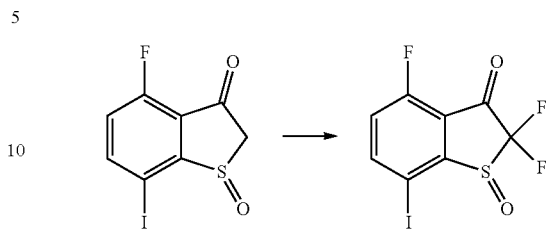

Into a 50-mL round-bottom flask, was placed 4-fluoro-7-iodobenzo[b]thiophen-3(2H)-one 1 oxide (780 mg, 2.515 mmol, 1.0 equiv), acetonitrile (15 mL), sodium carbonate (538 mg, 5.031 mmol, 2.0 equiv), selectfluor (1782 mg, 5.031 mmol, 2.0 equiv) and the resulting mixture was stirred at rt for 2 h. The reaction mixture was then concentrated under vacuum and to the residue was added DCM and water. The phases were separated and the organic layer was dried over anhydrous sodium sulfate and concentrated under vacuum. The residue was purified by silica gel column chromatography by eluting with ethyl acetate/petroleum ether (1:2) to afford 660 mg (75.8%) of the title compound. MS (ES, m z): [M+1]$^+$=346.9.

Step 6: 3-((2,2-difluoro-7-iodo-1-oxido-3-oxo-2,3-dihydrobenzo[b]thiophen-4-yl)oxy)-5-fluorobenzonitrile

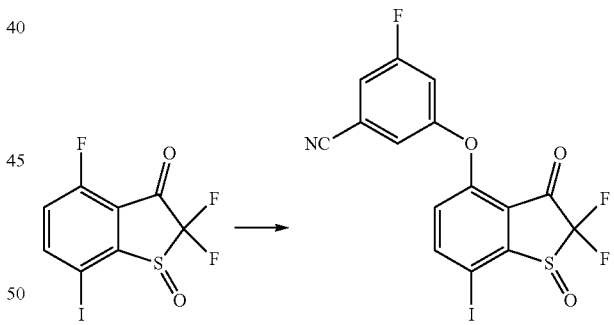

Into a 40-mL vial, was placed 2,2,4-trifluoro-7-iodobenzo[b]thiophen-3(2H)-one 1-oxide (660 mg, 1.907 mmol, 1.0 equiv), DMF (6 mL), 3-fluoro-5-hydroxybenzonitrile (314 mg, 2.289 mmol, 1.2 equiv), Cs$_2$CO$_3$ (1247 mg, 3.814 mmol, 2.0 equiv). After stirring at rt for 1 h, the reaction was quenched by water and extracted with ethyl acetate. The combined organic layer was dried over anhydrous sodium sulfate and concentrated. The residue was purified by silica gel column chromatography by eluting with ethyl acetate/ petroleum ether (1:3) to afford 500 mg (56.6%) of the title compound as a yellow solid. MS (ES, m z): [M+1]$^+$=464.0.

Example 22

Synthesis of 3-((2,2-difluoro-3-hydroxy-7-iodo-1-oxido-2,3-dihydrobenzo[b]thiophen-4-yl)oxy)-5-fluorobenzonitrile

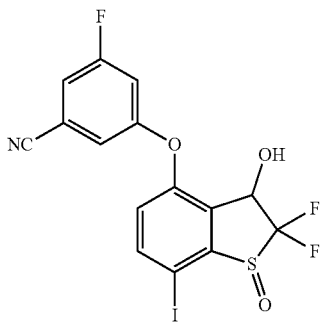 [SMILES: N#Cc1cc(F)cc(Oc2ccc(I)c3c2C(O)C(F)(F)S3=O)c1]

Into an 8-mL vial, was placed 3-((2,2-difluoro-7-iodo-1-oxido-3-oxo-2,3-dihydrobenzo-[b]thiophen-4-yl)oxy)-5-fluorobenzonitrile (230 mg, 0.497 mmol, 1.0 equiv), methanol (2 mL), NaBH$_4$ (38 mg, 0.993 mmol, 2.0 equiv). After stirring at rt for 2 h, the reaction was quenched by HCl aq. solution (1.0 M) and then extracted with ethyl acetate. The combined organic layers were dried over anhydrous sodium sulfate and concentrated under vacuum. The residue was purified b silica gel column chromatography by eluting with ethyl acetate/petroleum ether (1:3) to afford 200 mg (86.58%) of the title compound as yellow oil. MS (ES, m z): [M+1]$^+$=465.9.

Example 23

Synthesis of 3-((2,2-difluoro-3-hydroxy-7-(methylsulfonyl)-1-oxido-2,3-dihydro-benzo[b]-thiophen-4-yl)oxy)-5-fluorobenzonitrile

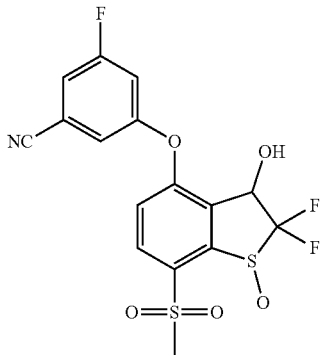

Into an 8-mL vial purged and maintained with an inert atmosphere of nitrogen, was placed 3-((2,2-difluoro-3-hydroxy-7-iodo-1-oxido-2,3-dihydrobenzo[b]thiophen-4-yl)oxy)-5-fluorobenzonitrile (275 mg, 0.591 mmol, 1.0 equiv), sodium methanesulfinate (91 mg, 0.887 mmol, 1.5 equiv), DMSO (3 mL), sodium (2S)-pyrrolidine-2-carboxylate (16 mg, 0.118 mmol, 0.2 equiv), CuI (23 mg, 0.118 mmol, 0.2 equiv). The resulting solution was stirred for 24 h at 65° C. in an oil bath. After cooled at rt, water was added and mixture was extracted with EtOAc. The combined organic layer was dried over anhydrous sodium sulfate and concentrated under vacuum. The residue was purified by silica gel column chromatography by eluting with ethyl acetate/petroleum ether (1:1) to afford 75 mg (30.4%) of the title compound as a yellow solid. MS (ES, m z): [M+1]$^+$=418.0.

Example 24

Synthesis of a mixture of 3-fluoro-5-(((1R,3R)-2,2,3-trifluoro-7-(methylsulfonyl)-1-oxido-2,3-dihydrobenzo[b]thiophen-4-yl)oxy)benzonitrile and 3-fluoro-5-(((1S,3S)-2,2,3-trifluoro-7-(methylsulfonyl)-1-oxido-2,3-dihydrobenzo[b]thiophen-4-yl)oxy)benzonitrile (24a) and a Mixture of 3-fluoro-5-(((1S,3R)-2,2,3-trifluoro-7-(methylsulfonyl)-1-oxido-2,3-dihydrobenzo[b]thiophen-4-yl)oxy)benzonitrile and 3-fluoro-5-(((1S,3S)-2,2,3-trifluoro-7-(methylsulfonyl)-1-oxido-2,3-dihydrobenzo[b]thiophen-4-yl)oxy)benzonitrile (24b)

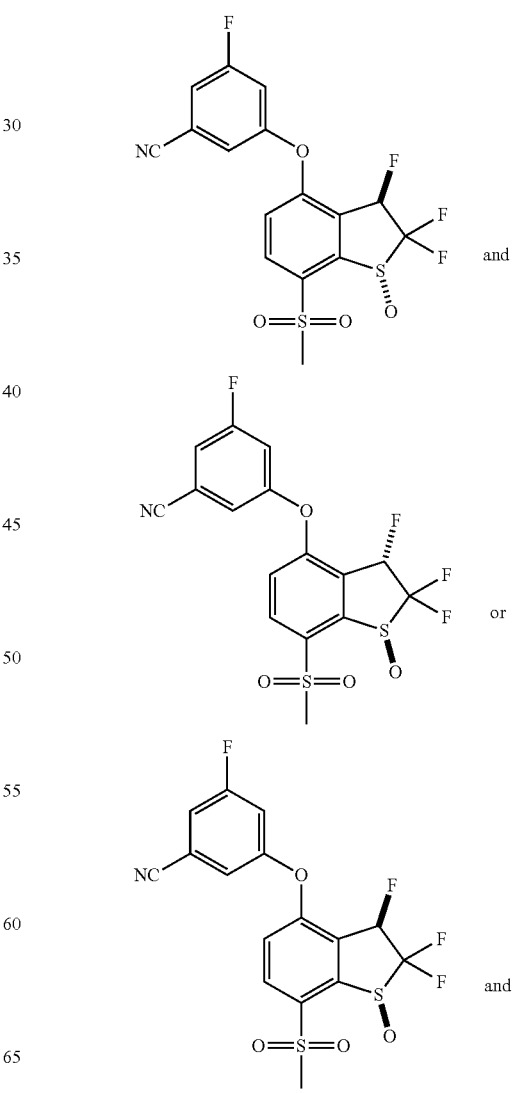

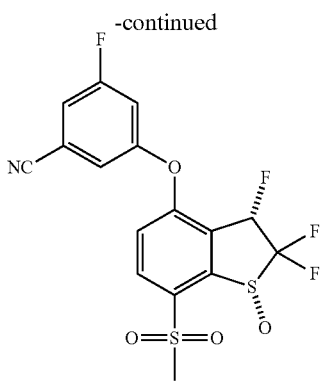

Into a 2-mL vial, was placed 3-((2,2-difluoro-3-hydroxy-7-(methylsulfonyl)-1-oxido-2,3-dihydrobenzo[b]thiophen-4-yl)oxy)-5-fluorobenzonitrile (19 mg, 0.046 mmol, 1.0 equiv), DCM (0.5 mL), DAST (11 mg, 0.068 mmol, 1.5 equiv). After stirring at rt for 2 h, the reaction was diluted with DCM and washed with water. The organic layer was dried over anhydrous sodium sulfate and concentrated under vacuum. The crude product was purified by Prep-TLC to afford 13 mg (68.1%) of the title compound as a white solid. MS (ES, m z): [M+1]$^+$=419.9.

The material was separated by Prep-HPLC to afford two diastereomers 1.5 mg of 24a and 5.7 mg of 24b. Compounds 24a and 24b: MS (ES, m z): [M+1]=420.

Example 25

Synthesis of 3-((2,2-difluoro-1-oxido-3-oxo-7-(trifluoromethyl)-2,3-dihydrobenzo[b]-thiophen-4-yl)oxy)-5-fluorobenzonitrile

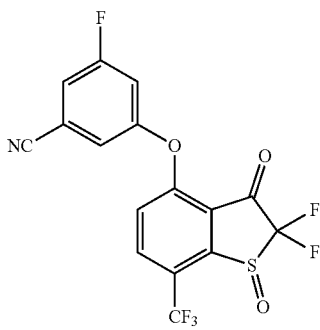 [SMILES: N#Cc1cc(F)cc(Oc2ccc(C(F)(F)F)c3c2C(=O)C(F)(F)S3=O)c1]

Step 1: 2,2,4-trifluoro-7-(trifluoromethyl)benzo[b]thiophen-3(2H)-one 1-oxide

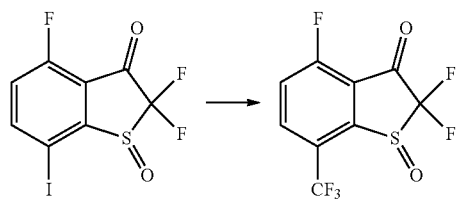 [SMILES: O=C1c2c(F)ccc(I)c2S(=O)C1(F)F ; O=C1c2c(F)ccc(C(F)(F)F)c2S(=O)C1(F)F]

To a stirred mixture of 2,2,4-trifluoro-7-iodobenzo[b]thiophen-3(2H)-one 1-oxide (500 mg, 1.44 mmol, 1.0 equiv) and methyl 2,2-difluoro-2-sulfoacetate (832.70 mg, 4.33 mmol, 3.0 equiv) in DMF (6 mL) was added CuI (27.52 mg, 0.14 mmol, 0.1 equiv). The resulting mixture was stirred for 1 h at 100° C. under nitrogen atmosphere. After cooled at rt, water was added and the mixture was extracted with EtOAc. The combined organic layers were washed with saturated brine, dried over anhydrous Na$_2$SO$_4$ and concentrated under reduced pressure. The residue was purified by silica gel column chromatography by eluting with PE/EtOAc (3:1) to afford the title compound 275 mg (66%) as a yellow solid. MS (ES, m z): [M+1]$^+$=288.9.

Step 2: 3-((2,2-difluoro-1-oxido-3-oxo-7-(trifluoromethyl)-2,3-dihydrobenzo[b]thiophen-4-yl)oxy)-5-fluorobenzonitrile

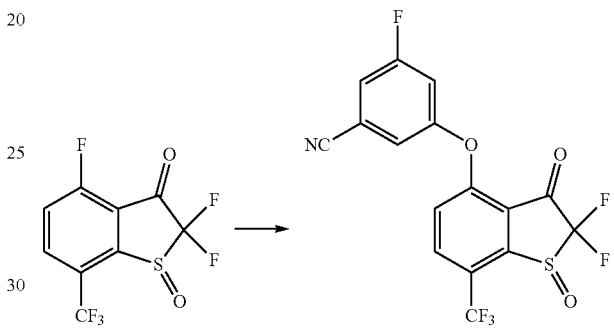

Into an 8 mL vial were added DMF (2 mL), 2,2,4-trifluoro-7-(trifluoromethyl)benzo[b]-thiophen-3(2H)-one 1-oxide (176 mg, 0.61 mmol, 1.0 equiv), 3-fluoro-5-hydroxybenzonitrile (92.12 mg, 0.67 mmol, 1.1 equiv) and Cs$_2$CO$_3$ (398.00 mg, 1.22 mmol, 2.0 equiv) at room temperature. After stirring at rt for 1 h, the reaction mixture was diluted with water and extracted with EtOAc. The organic layers were washed with water, dried over anhydrous Na$_2$SO$_4$ and concentrated. The residue was purified by silica gel column chromatography by eluting with PE/EtOAc (2:1) to afford the title compound 93 mg (37.57%) as a yellow oil. MS (ES, m z): [M+1]$^+$=406.0.

Example 26

Synthesis of 3-((2,2-difluoro-3-hydroxy-1-oxido-7-(trifluoromethyl)-2,3-dihydrobenzo[b]thiophen-4-yl)oxy)-5-fluorobenzonitrile

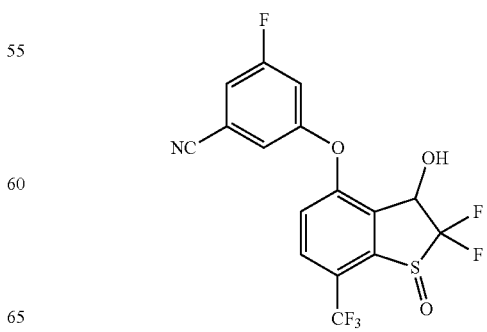

To a stirred solution of 3-((2,2-difluoro-1-oxido-3-oxo-7-(trifluoromethyl)-2,3-dihydrobenzo-[b]thiophen-4-yl)oxy)-5-fluorobenzonitrile (125 mg, 0.31 mmol, 1.0 equiv) in MeOH (3 mL) was added NaBH$_4$ (23.34 mg, 0.62 mmol, 2.0 equiv) at room temperature. After stirring at rt for 2 h, the reaction solution was concentrated under vacuum and the residue was neutralized to pH 7 with aq. HCl solution. The resulting mixture was extracted with EtOAc. The combined organic layer was dried over anhydrous Na$_2$SO$_4$ and concentrated under reduced pressure. The residue was purified by silica gel column chromatography, eluted with PE/EtOAc (2:1) to afford the title compound 105 mg (83.5%) as a yellow oil. MS (ES, m z): [M+1]$^+$=408.0.

Example 27

Synthesis of a mixture of 3-fluoro-5-((((1R,3R)-2,2,3-trifluoro-1-oxido-7-(trifluoromethyl)-2,3-dihydrobenzo[b]thiophen-4-yl)oxy)benzonitrile and 3-fluoro-5-((((1S,3S)-2,2,3-trifluoro-1-oxido-7-(trifluoromethyl)-2,3-dihydrobenzo[b]thiophen-4-yl)oxy)benzonitrile (27a) and a Mixture of 3-fluoro-5-((((1S,3R)-2,2,3-trifluoro-1-oxido-7-(trifluoromethyl)-2,3-dihydrobenzo[b]thiophen-4-yl)oxy)benzonitrile and 3-fluoro-5-((((1R,3S)-2,2,3-trifluoro-1-oxido-7-(trifluoromethyl)-2,3-dihydrobenzo[b]thiophen-4-yl)oxy)benzonitrile (27b)

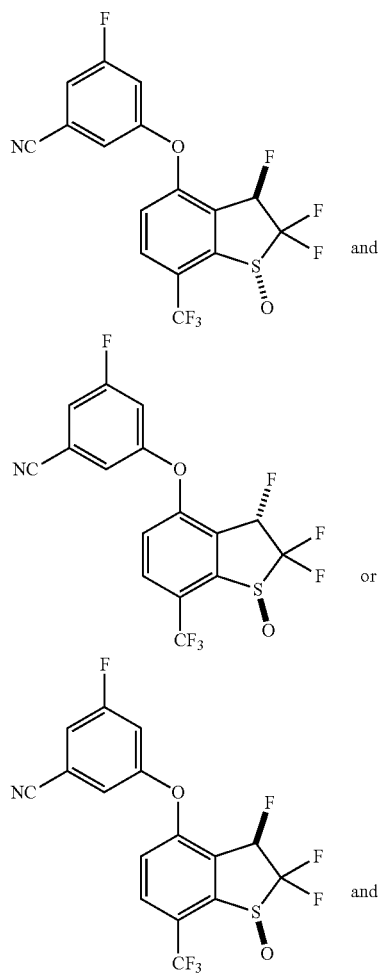

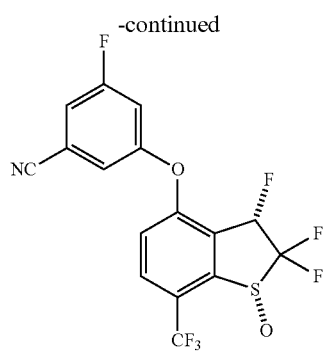

To a stirred solution of 3-((2,2-difluoro-3-hydroxy-1-oxido-7-(trifluoromethyl)-2,3-dihydro-benzo[b]thiophen-4-yl)oxy)-5-fluorobenzonitrile (100 mg, 0.24 mmol, 1.0 equiv) in DCM (2 mL) was added DAST (59.36 mg, 0.37 mmol, 1.5 equiv). The resulting solution was stirred for 3 h at rt. The resulting solution was diluted with DCM and washed with water. The organic layer was dried over anhydrous sodium sulfate and concentrated under vacuum. The crude product was purified by Prep-HPLC to afford two diastereomers 27a and 27b. MS (ES, m z): [M+1]$^+$=410.

Example 28

Synthesis of 3-((7-chloro-2,2,3,3-tetrafluoro-1-oxido-2,3-dihydrobenzo[b]thiophen-6-yl)oxy)-5-fluorobenzonitrile

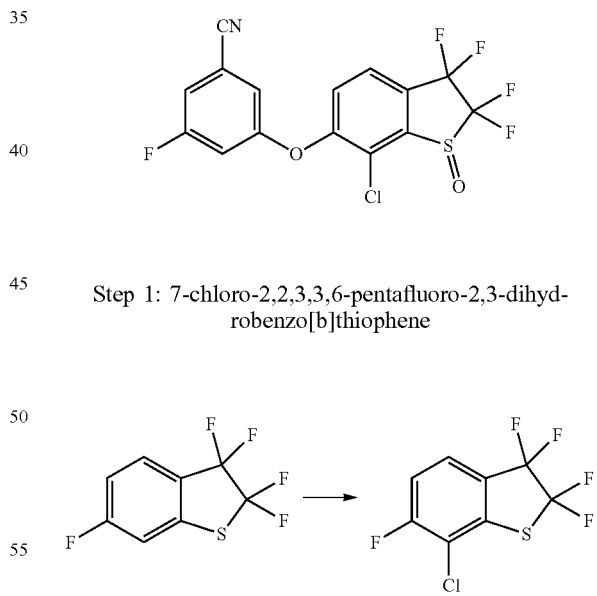

Step 1: 7-chloro-2,2,3,3,6-pentafluoro-2,3-dihydrobenzo[b]thiophene

To a stirred solution of 2,2,3,3,6-pentafluoro-2,3-dihydro-1-benzothiophene (200 mg, 0.88 mmol, 1.00 equiv) in THF (4 mL) was added LDA (0.88 mL, 1.326 mmol, 1.50 equiv) dropwise at −78° C. under nitrogen atmosphere. After stirring at −78° C.~−70° C. for 0.5 hour, to the above mixture was added hexachloroethane (523.3 mg, 2.21 mmol, 2.50 equiv) and the resulting mixture was stirred at −78° C.~−40° C. for additional 1 h. The reaction mixture was used directly in the next step.

Step 2: 3-((7-chloro-2,2,3,3-tetrafluoro-2,3-dihydrobenzo[b]thiophen-6-yl)oxy)-5-fluoro-benzonitrile

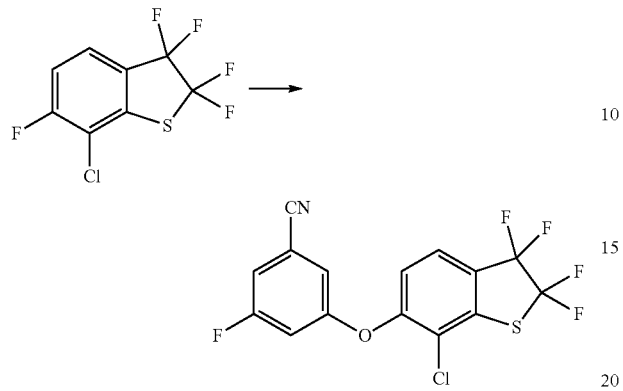

To a stirred solution of 7-chloro-2,2,3,3,6-pentafluoro-2,3-dihydro-1-benzothiophene (above reaction solution) and 3-fluoro-5-hydroxybenzonitrile (78.9 mg, 0.57 mmol, 1.50 equiv) in ACN (2 mL) were added $Cs_2CO_3$ (250.0 mg, 0.77 mmol, 2.00 equiv) in portions at room temperature under air atmosphere. The resulting mixture was stirred at 70° C. for 16 h under air atmosphere. After the reaction mixture was cooled at rt, the resulting mixture was filtered and the filtrate was concentrated under reduced pressure. The residue was purified by silica gel column chromatography by eluting with PE/EtOAc (10:1) to afford the title compound (100 mg, 69.00%) as a white solid.

Step 3. 3-((7-chloro-2,2,3,3-tetrafluoro-1-oxido-2,3-dihydrobenzo[b]thiophen-6-yl)oxy)-5-fluorobenzonitrile

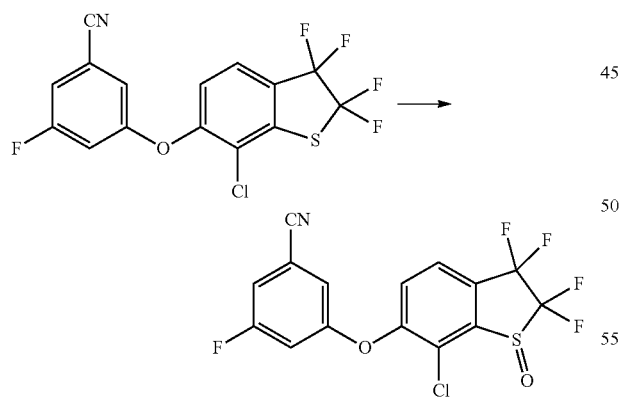

To a stirred solution 3-[(7-chloro-2,2,3,3-tetrafluoro-2,3-dihydro-1-benzothiophen-6-yl)oxy]-5-fluorobenzonitrile (50 mg, 1.00 equiv) in AcOH (0.9 mL) were added 30% $H_2O_2$(0.3 mL) dropwise at room temperature under air atmosphere. The resulting mixture was stirred at 90° C. for 2 h under air atmosphere. The mixture was then purified by Prep-HPL to afford the title compound (5 mg) as a white solid. MS (ES, m z): [M−1]⁻=391.9.

Example 29

Synthesis of 3-((7-chloro-2,2,3,3-tetrafluoro-1,1-dioxido-2,3-dihydrobenzo[b]thiophen-6-yl)oxy)-5-fluorobenzonitrile

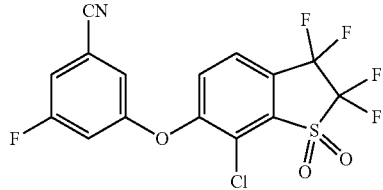 [SMILES: N#Cc1cc(F)cc(Oc2ccc3c(c2Cl)S(=O)(=O)C(F)(F)C3(F)F)c1]

To a stirred solution 3-[(7-chloro-2,2,3,3-tetrafluoro-2,3-dihydro-1-benzothiophen-6-yl)oxy] 5-fluorobenzonitrile (50 mg, 0.13 mmol, 1.00 equiv) in AcOH (1 mL) were added 30% $H_2O_2$(1 mL) dropwise at room temperature under air atmosphere. The resulting mixture was stirred at 105° C. for 16 h under air atmosphere. The mixture was purified by Prep-HPLC to afford the title compound (5 mg, 9.2%) as a white solid. MS (ES, m z): [M−1]⁻=407.8.

Example 30

Synthesis of 3-((7-bromo-2,2,3,3-tetrafluoro-1-oxido-2,3-dihydrobenzo[b]thiophen-6-yl)oxy)-5-fluorobenzonitrile

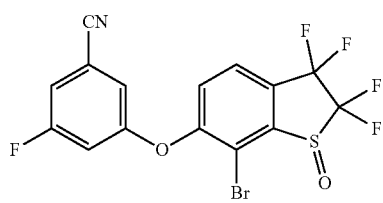 [SMILES: N#Cc1cc(F)cc(Oc2ccc3c(c2Br)S(=O)C(F)(F)C3(F)F)c1]

The title compound was synthesized following the method described in Example 28 using $CBr_4$ in step 1. GCMS (EI, m z): [M]=436.9.

Example 31

Synthesis of 6-(3-cyano-5-fluorophenoxy)-2,2,3,3-tetrafluoro-2,3-dihydrobenzo[b]thiophene-7-carbonitrile 1-oxide

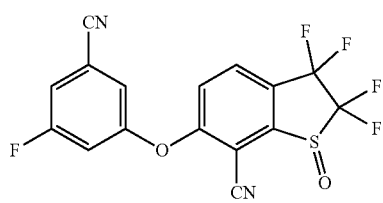 [SMILES: N#Cc1cc(F)cc(Oc2ccc3c(c2C#N)S(=O)C(F)(F)C3(F)F)c1]

Step 1: 2,2,3,3,6-pentafluoro-2,3-dihydrobenzo[b]thiophene-7-carbaldehyde oxime

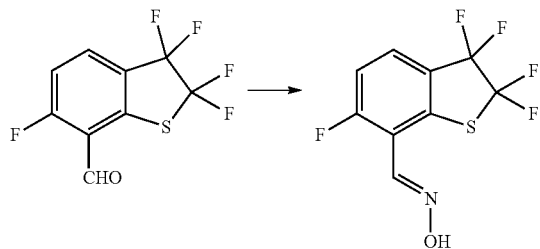 [SMILES: O=Cc1c(F)ccc2c1SC(F)(F)C2(F)F ; O/N=C/c1c(F)ccc2c1SC(F)(F)C2(F)F]

To a stirred solution of 2,2,3,3,6-pentafluoro-2,3-dihydro-1-benzothiophene-7-carbaldehyde (300 mg, 1.18 mmol, 1.0 equiv) and hydroxylamine (97.46 mg, 2.95 mmol, 2.5 equiv) in EtOH (3 mL) was added AcONa (387.30 mg, 4.72 mmol, 4.0 equiv) at rt. The resulting mixture was stirred at 90° C. for 16 h under $N_2$ atmosphere. After cooled at rt, the reaction was quenched with $H_2O$ and then was extracted with EtOAc. The organic layer was dried over anhydrous $Na_2SO_4$ and concentrated to afford the title compound (280 mg) as colorless oil.

Step 2: 2,2,3,3,6-pentafluoro-2,3-dihydrobenzo[b]thiophene-7-carbonitrile

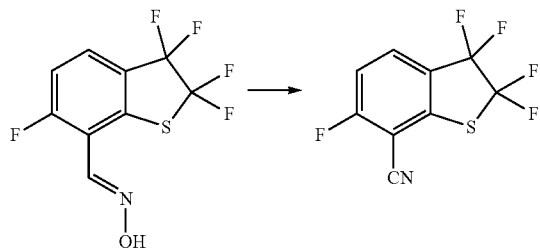 [SMILES: O/N=C/c1c(F)ccc2c1SC(F)(F)C2(F)F ; N#Cc1c(F)ccc2c1SC(F)(F)C2(F)F]

A solution of 2,2,3,3,6-pentafluoro-2,3-dihydrobenzo[b]thiophene-7-carbaldehyde oxime (200 mg, 0.74 mmol, 1.0 equiv) in $Ac_2O$ (2 mL) was heated at 100° C. for 4 h. After cooled at rt, the reaction was quenched by the addition of $H_2O$ (5 mL). The resulting mixture was extracted with EtOAc. The combined organic layers were washed with sat. $Na_2CO_3$ aq. solution, dried over anhydrous $Na_2SO_4$ and concentrated to give the title compound (150 mg) as colorless oil.

Step 3: 6-(3-cyano-5-fluorophenoxy)-2,2,3,3-tetrafluoro-2,3-dihydrobenzo[b]thiophene-7-carbonitrile

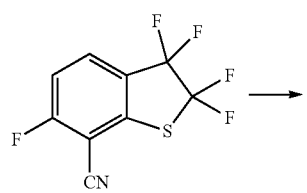

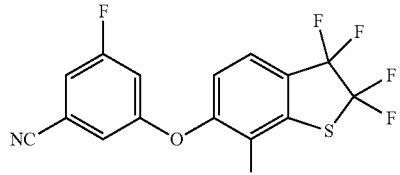

To a stirred solution of 2,2,3,3,6-pentafluoro-2,3-dihydro-1-benzothiophene-7-carbonitrile (70 mg, 0.28 mmol, 1.0 equiv) and 3-fluoro-5-hydroxybenzonitrile (45.86 mg, 0.33 mmol, 1.2 equiv) in DMF (2 mL) was added $Cs_2CO_3$ (181.61 mg, 0.56 mmol, 2.0 equiv) at rt and the resulting mixture was stirred at rt for 16 h. The reaction was quenched with $H_2O$ and extracted with EtOAc. The combined organic layers were washed with brine, dried over anhydrous $Na_2SO_4$ and concentrated. The residue was purified by silica gel column chromatography, eluted with PE/EA (1/1) to afford the title compound (60 mg, 58.4%) as a colorless oil.

Step 3. 6-(3-cyano-5-fluorophenoxy)-2,2,3,3-tetrafluoro-2,3-dihydrobenzo[b]thiophene-7-carbonitrile 1-oxide

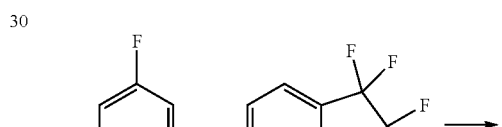

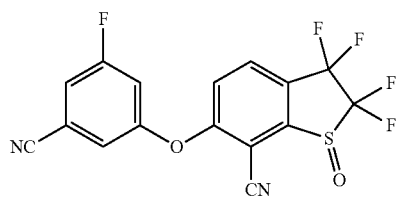

6-(3-cyano-5-fluorophenoxy)-2,2,3,3-tetrafluoro-2,3-dihydro-1-benzothiophene-7-carbonitrile (40 mg, 0.11 mmol, 1.0 equiv) was added into a solution of $H_2O_2$ (1.5 mL) and AcOH (0.5 mL) a rt and the resulting mixture was stirred at 90° C. for 3 h. The mixture was then purified by Prep-HPLC to afford the title compound (10 mg, 23.96%) as a white solid. MS (ES, m z): [M−1]⁻=38:

Example 32 and 33

Synthesis of 3-((7-(difluoromethyl)-2,2,3,3-tetrafluoro-1-oxido-2,3-dihydrothieno[3,2-b]pyridin-6-yl)oxy)-5-fluorobenzonitrile [32] and 3-((7-(difluoromethyl)-2,2,3,3-tetrafluoro-1,1-dioxido-2,3-dihydrothieno[3,2-b]pyridin-6-yl)oxy)-5-fluorobenzonitrile [33]

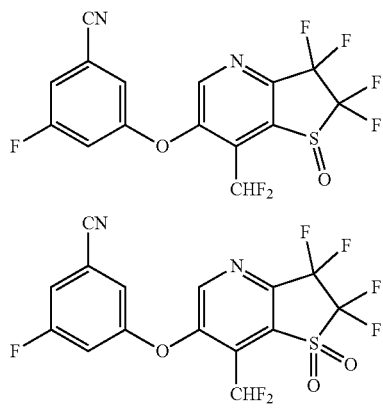

Step 1: 2-ethylhexyl 3-[(2-bromo-5-chloropyridin-3-yl)sulfanyl]propanoate

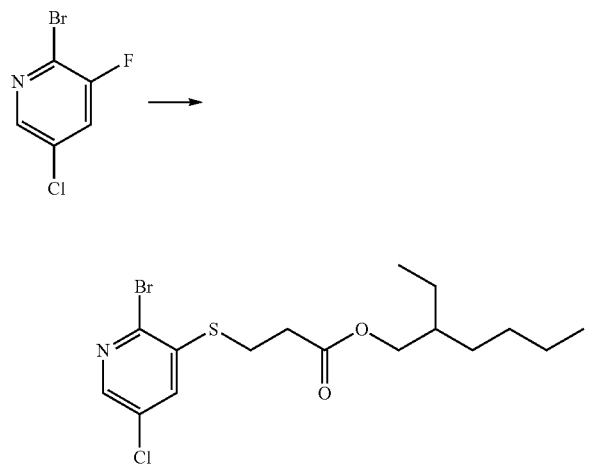

To a stirred mixture of 2-ethylhexyl 3-sulfanylpropanoate (6.74 g, 30.889 mmol, 1.3 equiv) and 2-bromo-5-chloro-3-fluoropyridine (4.96 g, 23.760 mmol, 1.0 equiv) in DMF (50 mL) was added NaH (1.23 g, 30.889 mmol, 1.3 equiv, 60%) in portions at 0° C. under nitrogen atmosphere. The resulting mixture was stirred for 4 h at room temperature and then quenched with ice water and extracted with EtOAc. The organic layer was washed with brine and dried over anhydrous Na₂SO₄. After filtration, the filtrate was concentrated under reduced pressure and purified by silica gel column chromatography by eluting with EtOAc/PE (0-10%) to afford the title compound (8 g, 82%).

Step 2: 2-bromo-5-chloropyridine-3-thiol

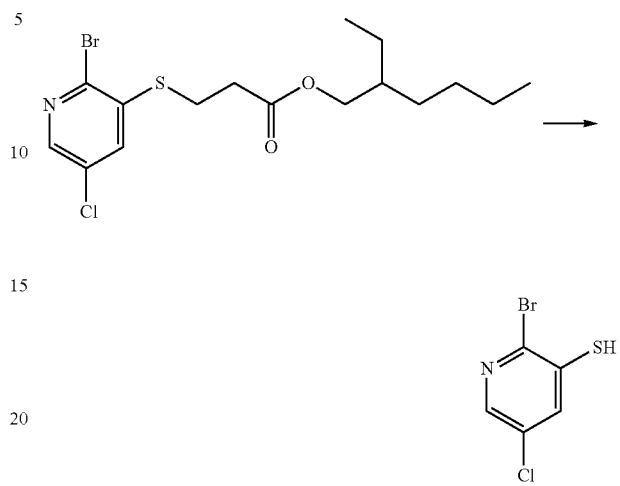

To a stirred mixture of 2-ethylhexyl 3-[(2-bromo-5-chloropyridin-3-yl)sulfanyl]propanoate (11 g, 26.909 mmol, 1.00 equiv) in THF (100 mL) was added t-BuONa (13.45 mL, 26.909 mmol, 1.00 equiv) at 0° C. under nitrogen atmosphere. After stirring for 1 h at room temperature, the mixture was acidified to pH 5 with 1.0 N HCl aq. solution and extracted with EtOAc. The organic layer was washed with brine, dried over anhydrous Na₂SO₄ and concentrated under reduced pressure. The residue was purified by silica gel column chromatography by eluting with PE/EtOAc (10:1) to afford the title compound (7 g, crude) as a light yellow solid.

Step 3: 2-bromo-3-[(2-bromo-1,1,2,2-tetrafluoroethyl)sulfanyl]-5-chloropyridine

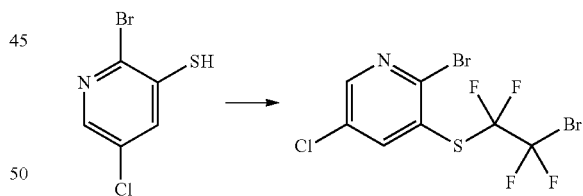

To a stirred solution of 2-bromo-5-chloropyridine-3-thiol (7 g, 31.180 mmol, 1.0 equiv) in DMF (50 mL) was added NaH (1.86 g, 46.77 mmol, 1.5 equiv, 60%) in portions at 0° C. under nitrogen atmosphere and the mixture was stirred for 30 mins at 0° C. At 0° C., 1,2-dibromo-1,1,2,2-tetrafluoroethane (10.53 g, 40.527 mmol, 1.30 equiv) was added and the reaction mixture was stirred for additional 4 hours at 0° C. The resulting mixture was quenched with ice water. The solid was filtered off and the filtrate was extracted with EtOAc. The organic layer was dried over anhydrous Na₂SO₄ and concentrated under reduced pressure. The residue was purified by silica gel column chromatography by eluting with PE to afford the title compound (5.8 g, 46.11%) as a colorless oil.

Step 4: 6-chloro-2,2,3,3-tetrafluoro-2H,3H-thieno[3,2-b]pyridine

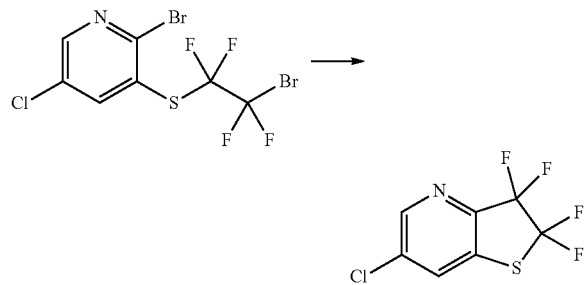

To a stirred mixture of 2-bromo-3-[(2-bromo-1,1,2,2-tetrafluoroethyl)sulfanyl]-5-chloropyridine (3.8 g, 9.420 mmol, 1.00 equiv) and Cu (2.99 g, 47.0 mmol, 5.00 equiv) in DMSO (10 mL) was added 2,2'-bipyridine (0.15 g, 0.942 mmol, 0.1 equiv) at room temperature under nitrogen atmosphere. After stirred for 1 h at 130° C., the reaction mixture was diluted with water and extracted with EtOAc. The organic layer was washed with brine, dried over anhydrous $Na_2SO_4$ and concentrated under reduced pressure. The residue was purified by silica gel column chromatography, eluted with PE to afford the title compound (780 mg, 33.99%) as light yellow oil.

Step 5: 6-chloro-2,2,3,3-tetrafluoro-2H,3H-thieno[3,2-b]pyridine-7-carbaldehyde

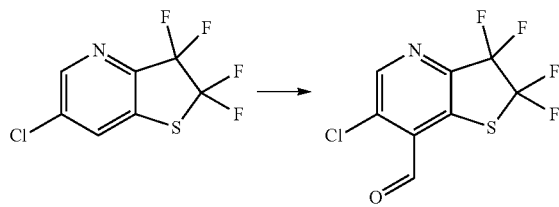 [SMILES: FC1(F)Sc2cc(Cl)cnc2C1(F)F ; O=Cc1c(Cl)cnc2c1SC(F)(F)C2(F)F]

To a stirred solution of 2,2,6,6-tetramethylpiperidine (707.28 mg, 5.007 mmol, 2.5 equiv) in THF (4 mL) was added n-BuLi (2 mL, 5.007 mmol, 2.5 M) dropwise at −30° C. under nitrogen atmosphere. After stirring for 0.5 h at 0° C., the mixture was added to 6-chloro-2,2,3,3-tetrafluoro octahydrothieno[3,2-b]pyridine (500 mg, 2.003 mmol, 1.00 equiv) in toluene (15 mL) at −78° C. The resulting mixture was stirred for 1 h between −78° C. and −70° C. To the above mixture was added ethyl formate (296.73 mg, 4.006 mmol, 2.00 equiv). The resulting mixture was stirred for additional 1 h between −78° C. and −50° C. The reaction mixture was poured into 1 M HCl, stirred for additional 2 min and then extracted with EtOAc. The organic layer was washed with brine, dried over anhydrous $Na_2SO_4$ and concentrated under reduced pressure. The residue was purified by silica gel column chromatography by eluting with PE/EtOAc (5:1) to afford of the title compound (250 mg, 45.96%) as a light yellow solid.

Step 6: 6-chloro-7-(difluoromethyl)-2,2,3,3-tetrafluoro-2H,3H-thieno[3,2-b]pyridine

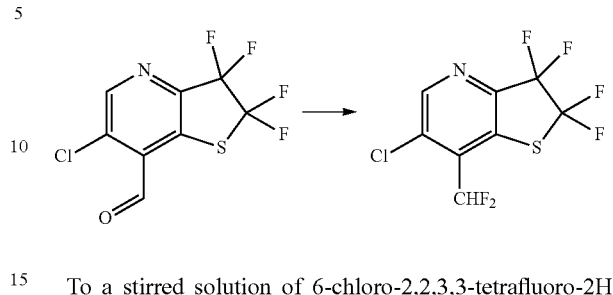

To a stirred solution of 6-chloro-2,2,3,3-tetrafluoro-2H,3H-thieno[3,2-b]pyridine-7-carbaldehyde (250 mg, 0.920 mmol, 1 equiv) in DCM (5 mL) was added DAST (741.82 mg, 4.602 mmol, 5.00 equiv) at room temperature. After stirring at rt for 16 h, the reaction mixture was quenched with saturated $NaHCO_3$ (aq.) at 0° C. and extracted with $Et_2O$. The organic layer was washed with brine, dried over anhydrous $Na_2SO_4$ and concentrated off under reduced pressure to afford of the title compound (220 mg, 81.41%) as a yellow oil.

Step 7: 3-[[7-(difluoromethyl)-2,2,3,3-tetrafluoro-2H,3H-thieno[3,2-b]pyridin-6-yl]oxy]-5-fluorobenzonitrile

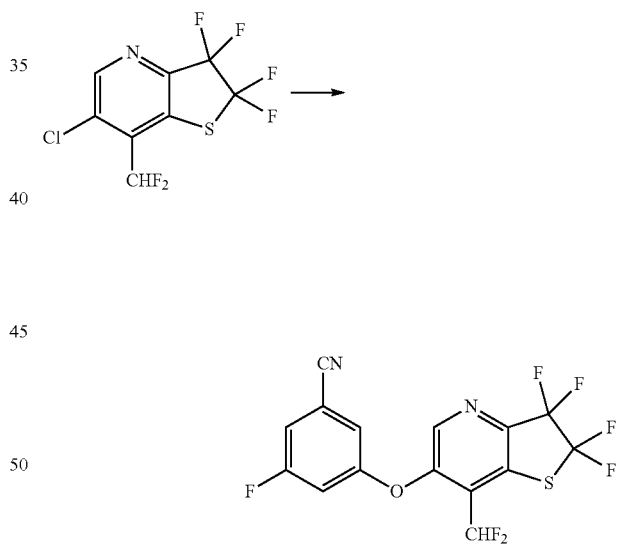

To a stirred solution of 6-chloro-7-(difluoromethyl)-2,2,3,3-tetrafluoro-2H,3H-thieno[3,2-b]-pyridine (110 mg, 0.375 mmol, 1.00 equiv) in DMF (2 mL) were added 3-fluoro-5-hydroxy-benzonitrile (56.51 mg, 0.412 mmol, 1.10 equiv) and $Cs_2CO_3$ (134.27 mg, 0.412 mmol, 1.10 equiv) at room temperature. After stirring at rt for 20 h, the reaction mixture was diluted with water and extracted with EtOAc. The organic layer was washed with brine, dried over anhydrous $Na_2SO_4$ and concentrated under reduced pressure. The residue was purified by silica gel column chromatography by eluting with PE/EtOAc (10:1) to afford the title compound (120 mg, 81.24%) as a white solid.

Step 8: 3-((7-(difluoromethyl)-2,2,3,3-tetrafluoro-1-oxido-2,3-dihydrothieno[3,2-b]pyridin-6-yl)oxy)-5-fluorobenzonitrile [32] and 3-((7-(difluoromethyl)-2,2,3,3-tetrafluoro-1,1-dioxido-2,3-dihydrothieno[3,2-b]pyridin-6-yl)oxy)-5-fluorobenzonitrile [33]

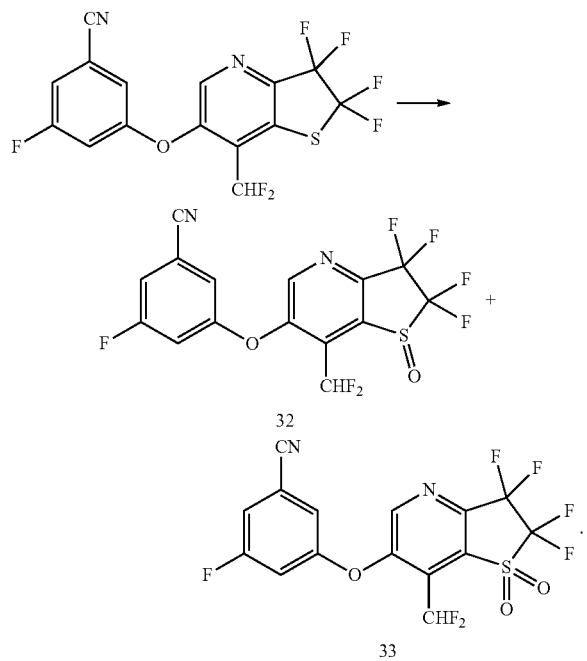

To a stirred solution of 3-[[7-(difluoromethyl)-2,2,3,3-tetrafluoro-2H,3H-thieno[3,2-b]pyridin-6-yl]oxy]-5-fluorobenzonitrile (25.00 mg, 0.063 mmol, 1.00 equiv) in $CH_3COOH$ (0.90 mL) was added $H_2O_2$ (0.30 mL) at room temperature and the resulting mixture was stirred at 90° C. for 16 h. After cooling the reaction mixture to at rt, the mixture was directly purified by Prep-HPLC to afford the title compound 32 (8 mg, 30.75%) and 33 (9 mg, 33.30%). Compound 32: MS (ES, m/z): $[M+1]^+=408.8$; Compound 33: MS (ES, m z): $[M+1]^+=424.8$.

Biological Example

Example 1

VEGF ELISA Assay

The ability of the disclosed compounds to inhibit HIF-2α was measured by determining VEGF expression in 786-0 cells. About 7500 786-0 cells were seeded into each well of a 96-well, white, clear bottom plate (07-200-566, Fisher Scientific) with 200 ul growth medium. Four hours later, compounds were dispensed into wells by Tecan D300e digital dispenser with starting concentration of 10 uM and ½ log of dilution down to 1 nM as final concentration. Each concentration of treatment was performed in duplicate. About 20 hours later, medium was removed and fresh medium was added, followed by compounds treatment as described above. 24 hours later, cell culture medium was collected to determine VEGF concentration using an ELISA kit (R&D systems, cat #DVE00) following the manufacturer's instruction.

The $IC_{50}$ is calculated by GraphPad Prism using the dose-response-inhibition (four parameter) equation. The plate with cells was then subjected to CellTiter-Glo luminescence cell viability assay (Promega) to determine the effect of these compounds on cell numbers after the above treatment.

What is claimed:
1. A compound of Formula (I):

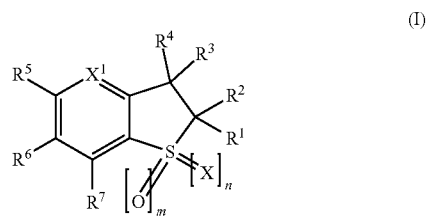

wherein:
m is 0 or 1;
n is 0 or 1, provided that at least one of m and n is 1;
X is O or $NR^8$ where $R^8$ is hydrogen, alkyl, cycloalkyl, cyano, haloalkyl, hydroxyalkyl, alkoxyalkyl, aminoalkyl, alkylcarbonyl, heteroaryl, or heterocyclyl;
$R^1$ is hydrogen, alkyl, or halo;
$R^2$ is hydrogen, alkyl, cycloalkyl, halo, haloalkyl, hydroxyalkyl, alkoxyalkyl, or aminoalkyl; or
$R^1$ and $R^2$ together with the carbon to which they are attached form >C(=O), cycloalkylene, or 4 to 6 membered heterocyclylene;
$R^3$ is hydrogen, alkyl, halo, haloalkyl, hydroxy, amino, monosubstituted amino, disubstituted amino, or alkoxy;
$R^4$ is hydrogen, deuterium, alkyl, or halo; or
$R^3$ and $R^4$ together with the carbon to which they are attached form >C(=O), cycloalkylene, or 4 to 6 membered heterocyclylene;
$R^5$ is hydrogen, alkyl, alkoxy, cyano, halo, haloalkyl, or haloalkoxy;
$R^6$ is -L-$R^{10}$ where L is a bond, S, O or NH, and where $R^{10}$ is cycloalkyl, bicyclic cycloalkyl, cycloalkylalkyl, aryl, aralkyl, heterocyclyl, spirocycloalkyl, spiroheterocyclylalkyl, heterocyclylalkyl, heteroaryl, or heteroaralkyl wherein aryl and heteroaryl, each by itself or as part of aralkyl or heteroaralkyl, and heterocyclyl are substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl;
$X^1$ is N or $CR^{11}$, where $R^{11}$ is hydrogen, alkyl, alkenyl, alkynyl, alkoxy, cyano, halo, haloalkyl, haloalkoxy, hydroxyalkyl, alkoxyalkyl, or aminoalkyl; and
$R^7$ is alkyl, cycloalkyl, alkoxy, cyano, halo, haloalkyl, haloalkoxy, alkylsulfoxide, alkylsulfonyl, —$SO_2NR^{13}R^{14}$ (where $R^{13}$ and $R^{14}$ are independently hydrogen or alkyl), —$S(O)R^{14}$(=$NHR^{15}$) (where $R^{14}$ is alkyl or haloalkyl and $R^{15}$ is hydrogen or cyano), or heteroaryl optionally substituted with $R^g$, $R^h$, and/or $R^i$ independently selected from hydrogen, alkyl, haloalkyl, haloalkoxy, alkoxy, hydroxy, halo, and cyano; or
a pharmaceutically acceptable salt thereof.

2. The compound of claim 1, or a pharmaceutically acceptable salt thereof wherein $X^1$ is $CR^{11}$.

3. The compound of claim 1, or a pharmaceutically acceptable salt thereof wherein $X^1$ is N.

4. The compound of claim 2, or a pharmaceutically acceptable salt thereof, wherein one of $R^3$ and $R^4$ is fluoro and the other of $R^3$ and $R^4$ is hydrogen or both $R^3$ and $R^4$ are fluoro.

5. The compound of claim 3, or a pharmaceutically acceptable salt thereof wherein one of $R^3$ and $R^4$ is fluoro and the other of $R^3$ and $R^4$ is hydrogen or both $R^3$ and $R^4$ are fluoro.

6. The compound of claim 4, or a pharmaceutically acceptable salt thereof wherein $R^1$ and $R^2$ are each fluoro.

7. The compound of claim 5, or a pharmaceutically acceptable salt thereof wherein m is 1 and n is 0.

8. The compound of claim 6, or a pharmaceutically acceptable salt thereof wherein m is 1 and n is 0.

9. The compound of claim 6, or a pharmaceutically acceptable salt thereof wherein m is 1, n is 1, and X is O.

10. The compound of claim 8, or a pharmaceutically acceptable salt thereof wherein L is O, S, or NH.

11. The compound of claim 9 or a pharmaceutically acceptable salt thereof wherein L is O, S, or NH.

12. The compound of claim 10, or a pharmaceutically acceptable salt thereof wherein $R^5$ is hydrogen, methyl, ethyl, methoxy, fluoro, cyano, trifluoromethyl, or trifluoromethoxy and $R^7$ is methyl, ethyl, methoxy, fluoro, bromo, cyano, cyclopropyl, trifluoromethyl, difluoromethyl, difluoromethoxy, trifluoromethoxy, or methylsulfonyl.

13. The compound of claim 11, or a pharmaceutically acceptable salt thereof wherein $R^5$ is hydrogen, methyl, ethyl, methoxy, fluoro, cyano, trifluoromethyl, or trifluoromethoxy and $R^7$ is methyl, ethyl, methoxy, fluoro, bromo, cyano, cyclopropyl, trifluoromethyl, difluoromethyl, difluoromethoxy, trifluoromethoxy, or methylsulfonyl.

14. The compound of claim 12, or a pharmaceutically acceptable salt thereof wherein $R^5$ is hydrogen and $R^7$ is difluoromethyl.

15. The compound of claim 13, or a pharmaceutically acceptable salt thereof wherein $R^5$ is hydrogen and $R^7$ is difluoromethyl.

16. The compound of claim 14, or a pharmaceutically acceptable salt thereof wherein $R^{10}$ is phenyl or heteroaryl, each ring substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl.

17. The compound of claim 15, or a pharmaceutically acceptable salt thereof wherein $R^{10}$ is phenyl or heteroaryl, each ring substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl.

18. The compound of claim 1, selected from the group consisting of:

3-((7-(difluoromethyl)-2,2,3-trifluoro-1-oxido-2,3-dihydrobenzo[b]thiophen-6-yl)oxy)-5-fluorobenzonitrile;
3-chloro-5-((7-(difluoromethyl)-2,2,3-trifluoro-1-oxido-2,3-dihydrobenzo-[b]thiophen-6-yl)oxy)benzonitrile;
7-(difluoromethyl)-6-(3,5-difluorophenoxy)-2,2,3-trifluoro-2,3-dihydrobenzo[b]-thiophene 1-oxide;
6-(3-chloro-5-fluorophenoxy)-7-(difluoromethyl)-2,2,3-trifluoro-2,3-dihydrobenzo[b]-thiophene 1-oxide;
3-((7-(difluoromethyl)-2,2,3,3-tetrafluoro-1-oxido-2,3-dihydrobenzo[b]thiophen-6-yl)-oxy)-5-fluorobenzonitrile;
7-(difluoromethyl)-6-(3,5-difluorophenoxy)-2,2,3,3-tetrafluoro-2,3-dihydrobenzo-[b]-thiophene 1-oxide;
3-((7-chloro-2,2,3,3-tetrafluoro-1-oxido-2,3-dihydrobenzo[b]thiophen-6-yl)oxy)-5-fluorobenzonitrile;
3-((7-bromo-2,2,3,3-tetrafluoro-1-oxido-2,3-dihydrobenzo[b]thiophen-6-yl)oxy)-5-fluorobenzonitrile;
6-(3-cyano-5-fluorophenoxy)-2,2,3,3-tetrafluoro-2,3-dihydrobenzo[b]thiophene-7-carbonitrile 1-oxide;
3-((7-(difluoromethyl)-2,2,3,3-tetrafluoro-1,1-dioxido-2,3-dihydrobenzo[b]-thiophen-6-yl)oxy)-5-fluorobenzonitrile; and
3-((7-chloro-2,2,3,3-tetrafluoro-1,1-dioxido-2,3-dihydrobenzo[b]thiophen-6-yl)-oxy)-5-fluorobenzonitrile; or pharmaceutically acceptable salt thereof.

19. A pharmaceutical composition comprising a compound of claim 1, or a pharmaceutically acceptable salt thereof, and a pharmaceutically acceptable excipient.

20. A pharmaceutical composition comprising a compound of claim 18, or a pharmaceutically acceptable salt thereof, and a pharmaceutically acceptable excipient.

21. A method of treating cancer or iron overload, in a patient which method comprises administering to the patient in recognized need thereof, a therapeutically effective amount of a compound of claim 1, or a pharmaceutically acceptable salt thereof; wherein the cancer is selected from renal cancer, glioblastoma, neuroblastoma, parananglioma, pheochromocytoma, pancreatic neuroendocrine tumors, liver cancer, colorectal cancer, hemangioblastomas, retinal cancers, von Hippel-Lindau disease, astrocytoma, lung cancer, non-small cell lung cancer, melanoma, breast cancer, cervical cancer, head and neck cancer, ovarian cancer, prostate cancer, and esophageal squamous cell carcinoma.

22. The method of claim 21, wherein the disease is cancer selected from renal cancer, glioblastoma, neuroblastoma, parananglioma, pheochromocytoma, pancreatic neuroendocrine tumors, liver cancer, colorectal cancer, hemangioblastomas, retinal cancers, von Hippel-Lindau disease, astrocytoma, lung cancer, non-small cell lung cancer, melanoma, breast cancer, cervical cancer, head and neck cancer, ovarian cancer, prostate cancer, and esophageal squamous cell carcinoma and the compound of claim 1, or a pharmaceutically acceptable salt thereof is optionally administered in combination with at least one other anticancer agent.

23. The method of claim 22, wherein the cancer is renal cancer.

* * * * *